(12) United States Patent
Ceulemans et al.

(10) Patent No.: US 11,615,288 B2
(45) Date of Patent: Mar. 28, 2023

(54) SECURE BROKER-MEDIATED DATA ANALYSIS AND PREDICTION

(71) Applicants: IMEC VZW, Leuven (BE); JANSSEN PHARMACEUTICA NV, Beerse (BE); KATHOLIEKE UNIVERSITEIT LEUVEN, Leuven (BE)

(72) Inventors: Hugo Ceulemans, Leuven (BE); Roel Wuyts, Leuven (BE); Wilfried Verachtert, Leuven (BE); Jaak Simm, Leuven (BE); Adam Arany, Leuven (BE); Yves Moreau, Leuven (BE); Charlotte Herzeel, Leuven (BE)

(73) Assignees: IMEC VZW, Leuven (BE); JANSSEN PHARMACEUTICA NV, Beerse (BE); KATHOLIEKE UNIVERSITEIT LEUVEN, Leuven (BE)

( * ) Notice: Subject to any disclaimer, the term of this patent is extended or adjusted under 35 U.S.C. 154(b) by 323 days.

(21) Appl. No.: 16/652,985

(22) PCT Filed: Oct. 1, 2018

(86) PCT No.: PCT/EP2018/076598
§ 371 (c)(1),
(2) Date: Apr. 1, 2020

(87) PCT Pub. No.: WO2019/068616
PCT Pub. Date: Apr. 11, 2019

(65) Prior Publication Data
US 2020/0265293 A1    Aug. 20, 2020

Related U.S. Application Data

(63) Continuation of application No. 15/722,742, filed on Oct. 2, 2017, now abandoned.

(51) Int. Cl.
    *G06N 3/04*    (2006.01)
    *G06N 3/08*    (2006.01)
    (Continued)

(52) U.S. Cl.
    CPC ....... *G06N 3/0427* (2013.01); *G06F 21/6218* (2013.01); *G06N 3/04* (2013.01);
    (Continued)

(58) Field of Classification Search
    CPC ........ G06N 3/0427; G06N 3/04; G06N 3/084; G06F 21/6218; G06F 21/6245; G16H 10/60; G16C 20/30; G16C 20/70
    See application file for complete search history.

(56) References Cited

U.S. PATENT DOCUMENTS 10,579,938 B2 *  3/2020  Zoldi ................... G06F 3/0485
10,645,548 B2 *  5/2020  Reynolds ............. H04L 63/104
(Continued)

FOREIGN PATENT DOCUMENTS

JP    2013117921 A    6/2013
JP    2014095931 A    5/2014

OTHER PUBLICATIONS

Li et al., "Parameter Server for Distributed Machine Learning", Proceedings of the 2014 International Conference on Big Data Science and Computing, Big Data Science, Jan. 1, 2014.
(Continued)

*Primary Examiner* — Hosuk Song
(74) *Attorney, Agent, or Firm* — Moser Taboada

(57) ABSTRACT

The present disclosure relates to secure broker-mediated data analysis and prediction. One example embodiment includes a method. The method includes receiving, by a managing computing device, a plurality of datasets from client computing devices. The method also includes computing, by the managing computing device, a shared repre-
(Continued)

sentation based on a shared function having one or more shared parameters. Further, the method includes transmitting, by the managing computing device, the shared representation and other data to the client computing devices. In addition, the method includes, based on the shared representation and the other data, the client computing devices update partial representations and individual functions with one or more individual parameters. Still further, the method includes determining, by the client computing devices, feedback values to provide to the managing computing device. Additionally, the method includes updating, by the managing computing device, the one or more shared parameters based on the feedback values.

27 Claims, 41 Drawing Sheets

(51) Int. Cl.
    *G06F 21/62*     (2013.01)
    *G06N 3/084*     (2023.01)
    *G16C 20/30*     (2019.01)
    *G16H 10/60*     (2018.01)
    *G16C 20/70*     (2019.01)

(52) U.S. Cl.
    CPC ......... *G06N 3/084* (2013.01); *G06F 21/6245* (2013.01); *G16C 20/30* (2019.02); *G16C 20/70* (2019.02); *G16H 10/60* (2018.01)

(56) References Cited

U.S. PATENT DOCUMENTS

| | | | | |
|---|---|---|---|---|
| 10,776,760 | B2 * | 9/2020 | Ethington | G06N 20/00 |
| 10,984,008 | B2 * | 4/2021 | Jacob | G06N 5/04 |
| 10,990,593 | B2 * | 4/2021 | Schneider | G06F 16/258 |
| 11,036,716 | B2 * | 6/2021 | Griffith | G06F 16/2365 |
| 11,210,307 | B2 * | 12/2021 | Jacob | G06F 16/2471 |
| 11,277,720 | B2 * | 3/2022 | Reynolds | H04W 4/38 |
| 11,341,367 | B1 * | 5/2022 | Barbosa | G06K 9/6279 |
| 2015/0278451 | A1 | 10/2015 | Kitano et al. | |
| 2017/0091651 | A1 | 3/2017 | Miao et al. | |
| 2017/0220949 | A1 | 8/2017 | Feng et al. | |

OTHER PUBLICATIONS

Shokri et al., "Privacy-Preserving Deep Learning", Proceedings of the 22nd ACM SIGSAC Conference on Computer and Communications Security, pp. 1310-1321, https://doi.org/10.1145/2810103.2813687, Jan. 1, 2015.

Harnie et al., "Scaling Machine Learning for Target Prediction in Drug Discovery using Apache Spark", 15$^{th}$ IEEE/ACM International Symposium on Cluster, Cloud and Grid Computing, May 4, 2015.

McMahan et al., "Federated Learning of Deep Networks using Model Averaging", arxiv.org, Cornell University Library, 201 Olin Library Cornell University Ithaca, NY14853, Feb. 18, 2016.

Konečný et al., "Federated Learning: Strategies for Improving Communication Efficiency", 29th Conference on Neural Information Processing Systems, Barcelona, Spain, Oct. 18, 2016.

International Search Report on Application No. PCT/EP2018/076598, dated Jan. 25, 2019.

Nikolaenko, Valeria et al., "Privacy-Preserving Matrix Factorization", Proceedings of the ACM Conference on Computer and Communications Security, Nov. 4-8, 2013.

Xu, Lei et al., "Information Security in Big Data: Privacy and Data Mining", IEEE Access, vol. 2, Oct. 20, 2014.

Simm, Jaak et al., "Macau: Scalable Bayesian Multi-Relational Factorization with Side Information Using MCMC", Machine Learning, arXiv: 1509.04610v2, Dec. 17, 2015.

Wikipedia, "Machine Learning", https://en.wikipedia.org/wiki/Machine_learning#Approaches, Sep. 13, 2017.

Wikipedia, "Proportional Hazards Model", https://en.wikipedia.org/wiki/Proportional_hazards_model#The_Cox_model, Sep. 13, 2017.

Simm, J. et al., "Macau: Scalable Bayesian Factorization with High-Dimensional Side Information using MCMC", 2017 IEEE International Workshop on Machine Learning for Signal Processing, Tokyo, Japan, Sep. 25-28, 2017.

* cited by examiner $X_A$

| | Book Title 1 | Book Title 2 | Book Title 3 | Book Title 4 | Book Title 5 | Book Title 6 | Book Title 7 |
|---|---|---|---|---|---|---|---|
| Timmy | 50 | 77 | 86 | 94 | 84 | 42 | |
| Johnny | | | | 88 | | | |
| Sally | 78 | | 55 | 17 | | 64 | |
| Sue | 22 | 27 | 98 | 67 | 10 | 84 | 31 |

$Y_A$

| | Movie Title 1 | Movie Title 2 | Movie Title 3 | Movie Title 4 | Movie Title 5 |
|---|---|---|---|---|---|
| Timmy | 91 | | | | |
| Johnny | 97 | 18 | 65 | 44 | 81 |
| Sally | 88 | | 22 | 27 | 50 |
| Sue | 61 | 87 | | | 70 |

|  | Book Title 1 | Book Title 2 | Book Title 3 | Book Title 4 | Book Title 5 | Book Title 6 | Book Title 7 |
|---|---|---|---|---|---|---|---|
| Timmy | 50 | 77 | 86 | 94 | 84 | 42 |  |
| Johnny |  |  |  | 88 |  |  |  |
| Margarette | 99 | 15 | 25 | 72 | 66 | 64 | 97 |

$Y_B$

|  | Movie Title 1 | Movie Title 3 | Movie Title 4 | Movie Title 5 | Movie Title 6 | Movie Title 7 | Movie Title 8 | Movie Title 9 | Movie Title 10 |
|---|---|---|---|---|---|---|---|---|---|
| Timmy | 91 | 97 |  | 45 |  |  |  |  |  |
| Johnny | 97 | 65 | 44 | 81 |  | 49 |  |  | 27 |
| Margarette |  | 88 |  |  | 90 |  | 61 |  |  |

| $X_A$ | | $M_A$ |
|---|---|---|
| Timmy | | User00 |
| Johnny | → | User01 |
| Sally | | User02 |
| Sue | | User03 |

| $X_B$ | | $M_B$ |
|---|---|---|
| Timmy | | User00 |
| Johnny | → | User01 |
| Margarette | | User04 |

FIG. 6B

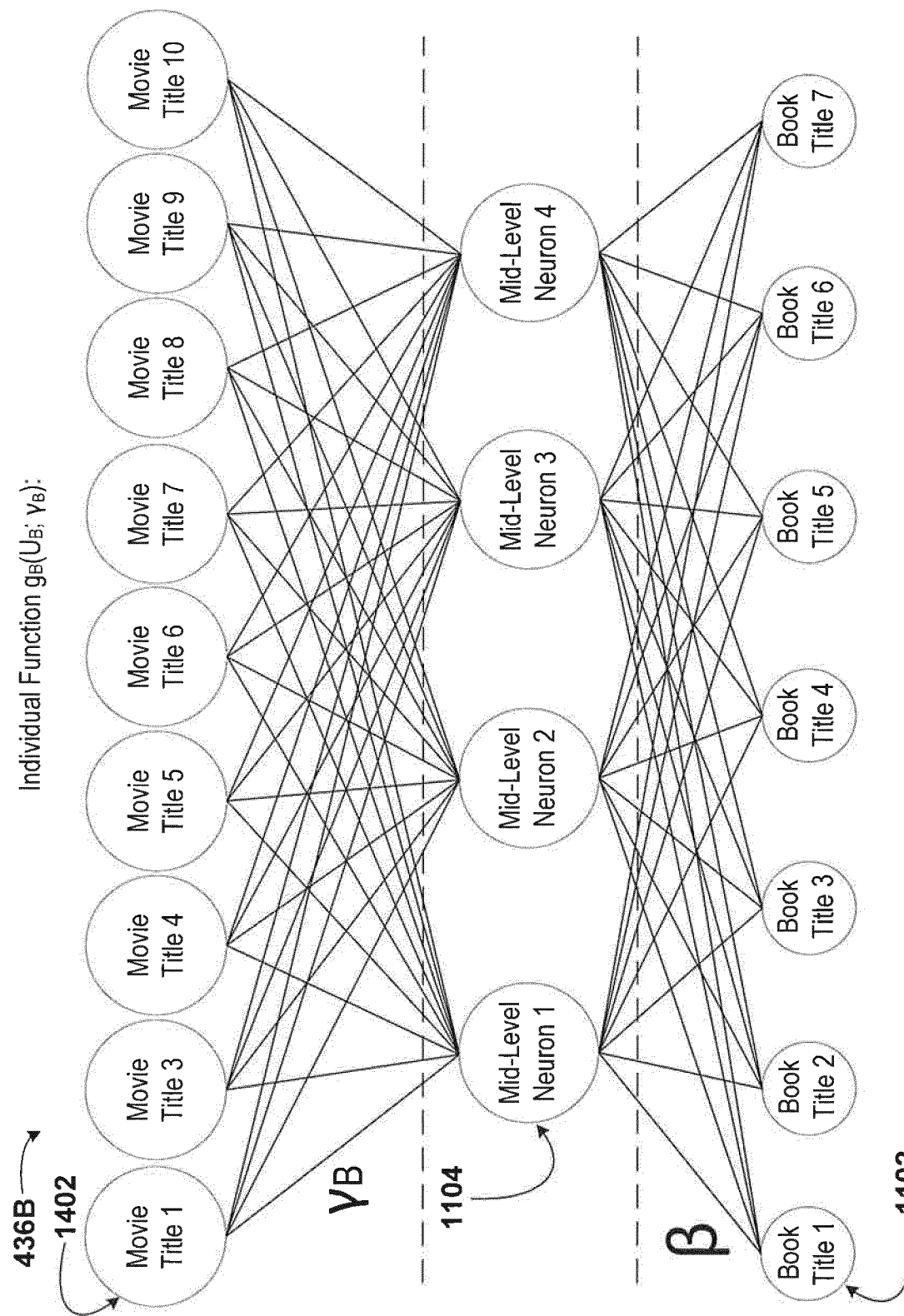

1602 → X<sub>Binary</sub>

| | Fewer than 3 Accidents | Greater than 3 Accidents | Accident Over $100k? | Restricted License? | Suspended License? | Insured for Accidents? |
|---|---|---|---|---|---|---|
| Jordan | ■ | | | ■ | | ■ |
| Jason | | | ■ | ■ | | |
| Alex | | ■ | ■ | | ■ | |
| Katie | ■ | | ■ | | | ■ |

1604 → Y<sub>Binary</sub>

| | Age | Gender | State of Residence | Income (in Thousands) | Number of Children | Married? |
|---|---|---|---|---|---|---|
| Jordan | 17 | M | NY | 0 | 0 | |
| Jason | 22 | M | KY | 42 | 2 | ■ |
| Alex | 32 | M | TX | 55 | 1 | |
| Katie | 24 | F | NY | 78 | 0 | ■ |

FIG. 16A

1612 → X<sub>Drug Discovery</sub>

| | Chemistry Fingerprint 1? | Chemistry Fingerprint 2? | Chemistry Fingerprint 3? | Additional Descriptor 1? | Additional Descriptor 2? | Additional Descriptor 3? |
|---|---|---|---|---|---|---|
| Compound A | ■ | ■ | ■ | ■ | ■ | |
| Compound B | | ■ | | | | ■ |
| Compound C | | ■ | | | ■ | |

1614 → Y<sub>Drug Discovery</sub>

| | Active in Assay 1? | Active in Assay 2? | Active in Assay 3? | Active in Assay 4? | Concentration for Half-Max Assay 5? | Active in Assay 6 | Active in Assay 7? | Active in Assay 8? | Concentration for Half-Max Assay 9? |
|---|---|---|---|---|---|---|---|---|---|
| Compound A | ■ | ■ | | ■ | 1.2 | ■ | | ■ | 5.1 |
| Compound B | | ■ | ■ | ■ | 1.8 | | | ■ | 0.3 |
| Compound C | ■ | | | | 0.2 | ■ | | | 0.8 |

FIG. 16B

1622 → $X_{Treatment}$

| | Age | Genetic Marker 1? | Gender | Weight | Family History of Disease 1? | Family History of Disease 2? |
|---|---|---|---|---|---|---|
| Patient A | 22 | ■ | F | 107 | | ■ |
| Patient B | 41 | | F | 145 | ■ | ■ |
| Patient C | 39 | ■ | M | 185 | ■ | |

1624 → $Y_{Treatment}$

| | Clinical Diagnosis 1? | Clinical Diagnosis 2? | Clinical Diagnosis 3? | Clinical Diagnosis 4? | Clinical Diagnosis 5? | Clinical Diagnosis 6? | Clinical Diagnosis 7? |
|---|---|---|---|---|---|---|---|
| Patient A | ■ | | | | | ■ | |
| Patient B | | ■ | ■ | ■ | | | ■ |
| Patient C | | | ■ | ■ | | ■ | |

FIG. 16C

$\bar{X} \times \bar{\beta} = \bar{U}$ $\bar{\beta} \quad \bar{U}$ $\bar{X}$ $\bar{U} \times \bar{V} = \bar{Y}$ $\bar{V}$ $\bar{Y}$ $\bar{U}$

| | Genre | Author | ISBN | Language | Publication Year |
|---|---|---|---|---|---|
| Book Title 1 | Horror | Wells | 56415 | English | 2007 |
| Book Title 2 | Mystery | Smith | 19745 | English | 2001 |
| Book Title 3 | History | Jordan | 68841 | Italian | 1954 |
| Book Title 4 | Sci-Fi | James | 84120 | French | 1984 |

$Y_A$

| | Timmy | Johnny | Sally | Sue | Mark |
|---|---|---|---|---|---|
| Book Title 1 | 91 | | | | |
| Book Title 2 | 97 | 18 | 65 | 44 | 81 |
| Book Title 3 | 88 | | 22 | 27 | 50 |
| Book Title 4 | 61 | 87 | | | 70 |

| | Genre | Author | ISBN | Language | Publication Year |
|---|---|---|---|---|---|
| Book Title 2 | Mystery | Smith | 19745 | English | 2001 |
| Book Title 5 | Mystery | Barnes | 94710 | English | 1999 |
| Book Title 6 | Political | Abrams | 51078 | French | 1977 |

$Y_B$

| | Bob | Margarette | Bram |
|---|---|---|---|
| Book Title 2 | 13 | | |
| Book Title 5 | | 73 | 58 |
| Book Title 6 | 28 | 56 | 74 |

| $X_A$ |
|---|
| Book Title 1 |
| Book Title 2 |
| Book Title 3 |
| Book Title 4 |

→

| $M_A$ |
|---|
| ISBN00 |
| ISBN01 |
| ISBN02 |
| ISBN03 |

| $X_B$ |
|---|
| Book Title 2 |
| Book Title 5 |
| Book Title 6 |

→

| $M_B$ |
|---|
| ISBN01 |
| ISBN04 |
| ISBN05 |

FIG. 19B

SECURE BROKER-MEDIATED DATA ANALYSIS AND PREDICTION

BACKGROUND

Unless otherwise indicated herein, the materials described in this section are not prior art to the claims in this application and are not admitted to be prior art by inclusion in this section.

Machine learning is a branch of computer science that seeks to automate the building of an analytical model. In machine learning, algorithms are used to create models that "learn" using datasets. Once "taught", the machine-learned models may be used to make predictions about other datasets, including future datasets. Machine learning has proven useful for developing models in a variety of fields. For example, machine learning has been applied to computer vision, statistics, data analytics, bioinformatics, deoxyribose nucleic acid (DNA) sequence identification, marketing, linguistics, economics, advertising, speech recognition, gaming, etc.

Machine learning involves training the model on a set of data, usually called "training data." Training the model may include two main subclasses: supervised learning and unsupervised learning.

In supervised learning, training data may include a plurality of datasets for which the outcome is known. For example, training data in the area of image recognition may correspond to images depicting certain objects which have been labeled (e.g., by a human) as containing a specific type of object (e.g., a dog, a pencil, a car, etc.). Such training data may be referred to as "labeled training data."

In unsupervised learning, the training data may not necessarily correspond to a known value or outcome. As such, the training data may be "unlabeled." Because the outcome for each piece of training data is unknown, the machine learning algorithm may infer a function from the training data. As an example, the function may be weighted based on one or more dimensions within the training data. Further, the function may be used to make predictions about new data to which the model is applied.

Upon training a model using training data, predictions may be made using the model. The more training data that is used to train a given model, the more the model may be refined and the more accurate the model may become. A common optimization in machine learning includes obtaining the most robust and reliable model while having access to the least amount of training data.

In some cases, additional sources of training data may provide a better-trained machine-learned model. However, in some scenarios, attaining more training data may not be possible. For example, two corporations may possess respective sets of training data that could be collectively used to train a machine-learned model that is superior to a model trained on either set of training data utilized individually. However, each corporation may desire that their data remains private (e.g., each corporation does not want to reveal the private data to the other corporation).

SUMMARY

The specification and drawings disclose embodiments that relate to secure broker-mediated data analysis and prediction.

The disclosure describes a method for performing joint machine learning using multiple datasets from multiple parties without revealing private information between the multiple parties. Such a method may include multiple client computing devices that transmit respective datasets to a managing computing device. The managing computing device may then combine the datasets, perform a portion of a machine learning algorithm on the combined datasets, and then transmit a portion of the results of the machine learning algorithm back to each of the client computing devices. Each client computing device may then perform another portion of the machine learning algorithm and send its portion of the results back to the managing computing device. Based on the results received from each client computing device, the managing computing device may then perform an additional portion of the machine learning algorithm to update a corresponding machine-learned model. In some cases, the method may be carried out multiple times in an optimization-type or recursive-type manner and/or may be carried out on an on-going basis.

In a first aspect, the disclosure describes a method. The method includes receiving, by a managing computing device, a plurality of datasets. Each dataset of the plurality of datasets is received from a respective client computing device of a plurality of client computing devices. Each dataset corresponds to a set of recorded values. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. The method additionally includes determining, by the managing computing device, a subset of the list of unique objects corresponding to each identifier in the subset of identifiers. Still further, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. In addition, the one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Even further, the one or more feedback values are also determined by the client computing devices by updating, by the respective client computing device, the one or more individual parameters for the respective dataset. Still further, the one or more feedback values are also determined by the client computing devices by determining, by the respective client computing device, the one or more feedback values, wherein the one or more feedback values are used to determine a change in the partial representation that corresponds to an improvement in the set of predicted values. The method also includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values.

In a second aspect, the disclosure describes a method. The method includes receiving, by a managing computing device, a plurality of datasets. Each dataset of the plurality of datasets is received from a respective client computing device of a plurality of client computing devices. Each dataset corresponds to a set of recorded values, wherein each dataset relates a plurality of chemical compounds to a plurality of descriptors of the chemical compounds. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. Still further, the method includes determining, by the managing computing device, a subset of the list of unique objects corresponding to each identifier in the subset of identifiers. Additionally, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. Even further, the one or more feedback values are determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. The set of recorded values corresponding to the respective dataset relates the plurality of chemical compounds to activities of the chemical compounds in a plurality of biological assays. In addition, the one or more feedback values are determined by the client computing devices by updating, by the respective client computing device, the one or more individual parameters for the respective dataset. Still further, the one or more feedback values are determined by the client computing devices by determining, by the respective client computing device, the one or more feedback values. The one or more feedback values are used to determine a change in the partial representation that corresponds to an improvement in the set of predicted values. The method additionally includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values. The shared representation, the shared function, or the one or more shared parameters are usable by at least one of the plurality of client computing devices to identify one or more effective treatment compounds among the plurality of chemical compounds.

In a third aspect, the disclosure describes a method. The method includes receiving, by a managing computing device, a plurality of datasets. Each dataset of the plurality of datasets is received from a respective client computing device of a plurality of client computing devices. Each dataset corresponds to a set of recorded values, wherein each dataset relates a plurality of patients to a plurality of descriptors of the patients. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. Still further, the method includes determining, by the managing computing device, a subset of the list of unique objects corresponding to each identifier in the subset of identifiers. Additionally, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. Even further, the one or more feedback values are determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. The set of recorded values corresponding to the respective dataset relates the plurality of patients to clinical diagnoses of patients. In addition, the one or more feedback values are determined by the client computing devices by updating, by the respective client computing device, the one or more individual parameters for the respective dataset. Still further, the one or more feedback values are determined by the client computing devices by determining, by the respective client computing device, the one or more feedback values. The one or more feedback values are used to determine a change in the partial representation that corresponds to an improvement in the set of predicted values. The method additionally includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values. The shared representation, the shared function, or the one or more shared parameters are usable by at least one of the plurality of client computing devices to diagnose one or more of the plurality of patients.

In a fourth aspect, the disclosure describes a method. The method includes receiving, by a managing computing device, a plurality of datasets. Each dataset of the plurality of datasets is received from a respective client computing device of a plurality of client computing devices. Each dataset corresponds to a set of recorded values, wherein each dataset provides a set of book ratings for a plurality of book titles by a plurality of users. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. Still further, the method includes determining, by the managing computing device, a subset of the list of unique objects corresponding to each identifier in the subset of identifiers. Additionally, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. Even further, the one or more feedback values are determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. The set of recorded values corresponding to the respective dataset provides a set of movie ratings for a plurality of movie titles by the plurality of users. In addition, the one or more feedback values are determined by the client computing devices by updating, by the respective client computing device, the one or more individual parameters for the respective dataset. Still further, the one or more feedback values are determined by the client computing devices by determining, by the respective client computing device, the one or more feedback values. The one or more feedback values are used to determine a change in the partial representation that corresponds to an improvement in the set of predicted values. The method additionally includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values. The shared representation, the shared function, or the one or more shared parameters are usable by at least one of the plurality of client computing devices to recommend a movie to one or more of the plurality of users.

In a fifth aspect, the disclosure describes a method. The method includes transmitting, by a first client computing device to a managing computing device, a first dataset corresponding to the first client computing device. The first dataset is one of a plurality of datasets transmitted to the managing computing device by a plurality of client computing devices. Each dataset corresponds to a set of recorded values. Each dataset includes objects. The method also includes receiving, by the first client computing device, a first sublist of objects for the first dataset and a first partial representation for the first dataset. The first sublist of objects for the first dataset and the first partial representation for the first dataset are determined by determining, by the managing computing device, a respective list of identifiers for each dataset and a composite list of identifiers that includes a combination of the lists of identifiers of each dataset of the plurality of datasets. The first sublist of objects for the first dataset and the first partial representation for the first dataset are also determined by determining, by the managing computing device, a list of unique objects from among the plurality of datasets. Further, the first sublist of objects for the first dataset and the first partial representation for the first dataset are determined by selecting, by the managing computing device, the subset of identifiers from the composite list of identifiers. Even further, the first sublist of objects for the first dataset and the first partial representation for the first dataset are determined by determining, by the managing computing device, a subset of the list of unique objects corresponding to each identifier in the subset of identifiers. Still further, the first sublist of objects for the first dataset and the first partial representation for the first dataset are determined by computing, by the managing computing device, the shared representation of the plurality of datasets based on the subset of the list of unique objects and a shared function having one or more shared parameters. Even further, the first sublist of objects for the first dataset and the first partial representation for the first dataset are determined by determining, by the managing computing device, the first sublist of objects for the first dataset based on an intersection of the subset of identifiers with the list of identifiers for the first dataset. Yet further, the first sublist of objects for the first dataset and the first partial representation for the first dataset are determined by determining, by the managing computing device, the first partial representation for the first dataset based on the first sublist of objects and the shared representation. Even further, the method includes determining, by the first client computing device, a first set of predicted values corresponding to the first dataset. The first set of predicted values is based on the first partial representation and a first individual function with one or more first individual parameters corresponding to the first dataset. In addition, the method includes determining, by the first client computing device, a first error for the first dataset based on a first individual loss function for the first dataset, the first set of predicted values corresponding to the first dataset, the first sublist of objects, and non-empty entries in the set of recorded values corresponding to the first dataset. Still further, the method includes updating, by the first client computing device, the one or more first individual parameters for the first dataset. Yet further, the method includes determining, by the first client computing device, one or more feedback values. The one or more feedback values are used to determine a change in the first partial representation that corresponds to an improvement in the first set of predicted values. Yet still further, the method includes transmitting, by the first client computing device to the managing computing device, the one or more feedback values. The one or more feedback values are usable by the managing computing device along with sublists of objects from the plurality of client computing devices to determine one or more aggregated feedback values. The one or more aggregated feedback values are usable by the managing computing device to update the one or more shared parameters.

In a sixth aspect, the disclosure describes a non-transitory, computer-readable medium with instructions stored thereon. The instructions are executable by a processor to perform a method. The method includes receiving, by a managing computing device, a plurality of datasets. Each dataset of the plurality of datasets is received from a respective client computing device of a plurality of client computing devices. Each dataset corresponds to a set of recorded values. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. The method additionally includes determining, by the managing computing device, a subset of the list of unique objects corresponding to each identifier in the subset of identifiers. Still further, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. In addition, the one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Even further, the one or more feedback values are also determined by the client computing devices by updating, by the respective client computing device, the one or more individual parameters for the respective dataset. Still further, the one or more feedback values are also determined by the client computing devices by determining, by the respective client computing device, the one or more feedback values, wherein the one or more feedback values are used to determine a change in the partial representation that corresponds to an improvement in the set of predicted values. The method also includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values.

In a seventh aspect, the disclosure describes a memory with a model stored thereon. The model is generated according to a method. The method includes receiving, by a managing computing device, a plurality of datasets. Each dataset of the plurality of datasets is received from a respective client computing device of a plurality of client computing devices. Each dataset corresponds to a set of recorded values. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. The method additionally includes determining, by the managing computing device, a subset of the list of unique objects corresponding to each identifier in the subset of identifiers. Still further, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. In addition, the one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Even further, the one or more feedback values are also determined by the client computing devices by updating, by the respective client computing device, the one or more individual parameters for the respective dataset. Still further, the one or more feedback values are also determined by the client computing devices by determining, by the respective client computing device, the one or more feedback values, wherein the one or more feedback values are used to determine a change in the partial representation that corresponds to an improvement in the set of predicted values. The method also includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values. Yet even further, the method includes storing, by the managing computing device, the shared representation, the shared function, and the one or more shared parameters on the memory.

In an eighth aspect, the disclosure describes a method. The method includes receiving, by a managing computing device, a plurality of datasets. Each dataset of the plurality of datasets is received from a respective client computing device of a plurality of client computing devices. Each dataset corresponds to a set of recorded values. Each dataset includes objects. The method also includes determining, by the managing computing device, a respective list of identifiers for each dataset and a composite list of identifiers including a combination of the lists of identifiers of each dataset of the plurality of datasets. Further, the method includes determining, by the managing computing device, a list of unique objects from among the plurality of datasets. In addition, the method includes selecting, by the managing computing device, a subset of identifiers from the composite list of identifiers. The method additionally includes determining, by the managing computing device, a subset of the list of unique objects corresponding to each identifier in the subset of identifiers. Still further, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Still even further, the method includes determining, by the managing computing device, a partial representation for the respective dataset of each client computing device based on the sublist of objects for the respective dataset and the shared representation. Even yet further, the method includes transmitting, by the managing computing device, to each of the client computing devices the sublist of objects for the respective dataset and the partial representation for the respective dataset. Yet further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. In addition, the one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Even further, the one or more feedback values are also determined by the client computing devices by updating, by the respective client computing device, the one or more individual parameters for the respective dataset. Still further, the one or more feedback values are also determined by the client computing devices by determining, by the respective client computing device, the one or more feedback values, wherein the one or more feedback values are used to determine a change in the partial representation that corresponds to an improvement in the set of predicted values. The method also includes determining, by the managing computing device, based on the sublists of objects and the one or more feedback values from the client computing devices, one or more aggregated feedback values. Yet still further, the method includes updating, by the managing computing device, the one or more shared parameters based on the one or more aggregated feedback values. Yet even further, the method includes using, by a computing device, the shared representation, the shared function, or the one or more shared parameters to determine an additional set of predicted values corresponding to a dataset.

In a ninth aspect, the disclosure describes a server device. The server device has instructions stored thereon that, when executed by a processor, perform a method. The method includes receiving a plurality of datasets. Each dataset of the plurality of datasets is received from a respective client computing device of a plurality of client computing devices. Each dataset corresponds to a set of recorded values. Each dataset includes objects. The method also includes determining a respective list of identifiers for each dataset and a composite list of identifiers that includes a combination of the lists of identifiers of each dataset of the plurality of datasets. Further, the method includes determining a list of unique objects from among the plurality of datasets. In addition, the method includes selecting a subset of identifiers from the composite list of identifiers. Still further, the method includes determining a subset of the list of unique objects corresponding to each identifier in the subset of identifiers. The method additionally includes computing a shared representation of the datasets based on the subset of the list of unique objects and a shared function having one or more shared parameters. Even further, the method includes determining a sublist of objects for the respective dataset of each client computing device based on an intersection of the subset of identifiers with the list of identifiers for the respective dataset. Yet further, the method includes determining a partial representation for the respective dataset of each client computing device based on the sublist of objects for the respective dataset and the shared representation. Even still further, the method includes transmitting to each of the client computing devices: the sublist of objects for the respective dataset and the partial representation for the respective dataset. Yet still further, the method includes receiving one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. The one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Further, the one or more feedback values are determined by the client computing devices by updating, by the respective client computing device, the one or more individual parameters for the respective dataset. In addition, the one or more feedback values are determined by the client computing devices by determining, by the respective client computing device, the one or more feedback values. The one or more feedback values are used to determine a change in the partial representation that corresponds to an improvement in the set of predicted values. Even yet further, the method includes determining based on the sublists of objects and the one or more feedback values from the client computing devices, one or more aggregated feedback values. Still yet further, the method includes updating the one or more shared parameters based on the one or more aggregated feedback values.

In a tenth aspect, the disclosure describes a server device. The server device has instructions stored thereon that, when executed by a processor, perform a method. The method includes transmitting, to a managing computing device, a first dataset corresponding to the server device. The first dataset is one of a plurality of datasets transmitted to the managing computing device by a plurality of server devices. Each dataset corresponds to a set of recorded values. Each dataset includes objects. The method also includes receiving a first sublist of objects for the first dataset and a first partial representation for the first dataset. The first sublist of objects for the first dataset and the first partial representation for the first dataset are determined by the managing computing device by determining, by the managing computing device, a respective list of identifiers for each dataset and a composite list of identifiers that includes a combination of the lists of identifiers of each dataset of the plurality of datasets. The first sublist of objects for the first dataset and the first partial representation for the first dataset are also determined by the managing computing device by determining, by the managing computing device, a list of unique objects from among the plurality of datasets. Further, the first sublist of objects for the first dataset and the first partial representation for the first dataset are determined by the managing computing device by selecting, by the managing computing device, a subset of identifiers from the composite list of identifiers. In addition, the first sublist of objects for the first dataset and the first partial representation for the first dataset are determined by the managing computing device by determining, by the managing computing device, a subset of the list of unique objects corresponding to each identifier in the subset of identifiers. Still further, the first sublist of objects for the first dataset and the first partial representation for the first dataset are determined by the managing computing device by computing, by the managing computing device, a shared representation of the plurality of datasets based on the subset of the list of unique objects and a shared function having one or more shared parameters. The first sublist of objects for the first dataset and the first partial representation for the first dataset are additionally determined by the managing computing device by determining, by the managing computing device, the first sublist of objects for the first dataset based on an intersection of the subset of identifiers with the list of identifiers for the first dataset. Yet further, the first sublist of objects for the first dataset and the first partial representation for the first dataset are determined by the managing computing device by determining, by the managing computing device, the first partial representation for the first dataset based on the first sublist of objects and the shared representation. Further, the method includes determining a first set of predicted values corresponding to the first dataset. The first set of predicted values is based on the first partial representation and a first individual function with one or more first individual parameters corresponding to the first dataset. Additionally, the method includes determining a first error for the first dataset based on a first individual loss function for the first dataset, the first set of predicted values corresponding to the first dataset, the first sublist of objects, and non-empty entries in the set of recorded values corresponding to the first dataset. Even further, the method includes updating the one or more first individual parameters for the first dataset. The method additionally includes determining one or more feedback values. The one or more feedback values are used to determine a change in the first partial representation that corresponds to an improvement in the first set of predicted values. Yet further, the method includes transmitting, to the managing computing device, the one or more feedback values. The one or more feedback values are usable by the managing computing device along with sublists of objects from the plurality of server devices to determine one or more aggregated feedback values. The one or more aggregated feedback values are usable by the managing computing device to update the one or more shared parameters.

In an eleventh aspect, the disclosure describes a system. The system includes a server device. The system also includes a plurality of client devices each communicatively coupled to the server device. The server device has instructions stored thereon that, when executed by a processor, perform a first method. The first method includes receiving a plurality of datasets. Each dataset of the plurality of datasets is received from a respective client device of the plurality of client devices. Each dataset corresponds to a set of recorded values. Each dataset includes objects. The first method also includes determining a respective list of identifiers for each dataset and a composite list of identifiers that includes a combination of the lists of identifiers of each dataset of the plurality of datasets. Additionally, the first method includes determining a list of unique objects from among the plurality of datasets. Further, the first method includes selecting a subset of identifiers from the composite list of identifiers. The first method additionally includes determining a subset of the list of unique objects corresponding to each identifier in the subset of identifiers. The first method further includes computing a shared representation of the datasets based on the subset of the list of unique objects and a shared function having one or more shared parameters. Still further, the first method includes determining a sublist of objects for the respective dataset of each client device based on an intersection of the subset of identifiers with the list of identifiers for the respective dataset. Yet further, the first method includes determining a partial representation for the respective dataset of each client device based on the sublist of objects for the respective dataset and the shared representation. Even further, the first method includes transmitting to each of the client devices: the sublist of objects for the respective dataset and the partial representation for the respective dataset. Each client device has instructions stored thereon that, when executed by a processor, perform a second method. The second method includes determining a set of predicted values corresponding to the respective dataset. The set of predicted values is based on the partial representation and an individual function with one or more individual parameters corresponding to the respective dataset. The second method also includes determining an error for the respective dataset based on an individual loss function for the respective dataset, the set of predicted values corresponding to the respective dataset, the sublist of objects, and non-empty entries in the set of recorded values corresponding to the respective dataset. Further, the second method includes updating the one or more individual parameters for the respective dataset. The second method additionally includes determining one or more feedback values. The one or more feedback values are used to determine a change in the partial representation that corresponds to an improvement in the set of predicted values. The second method further includes transmitting, to the server device, the one or more feedback values. Yet even further, the first method includes determining based on the sublists of objects and the one or more feedback values from the client devices, one or more aggregated feedback values. Still yet further, the first method includes updating the one or more shared parameters based on the one or more aggregated feedback values.

In a twelfth aspect, the disclosure describes an optimized model. The model is optimized according to a method. The method includes receiving, by a managing computing device, a plurality of datasets. Each dataset of the plurality of datasets is received from a respective client computing device of a plurality of client computing devices. Each dataset corresponds to a set of recorded values. Each dataset includes objects. The method also includes determining, by the managing computing device, a respective list of identifiers for each dataset and a composite list of identifiers that includes a combination of the lists of identifiers of each dataset of the plurality of datasets. Further, the method includes determining, by the managing computing device, a list of unique objects from among the plurality of datasets. The method additionally includes selecting, by the managing computing device, a subset of identifiers from the composite list of identifiers. The method further includes determining, by the managing computing device, a subset of the list of unique objects corresponding to each identifier in the subset of identifiers. Additionally, the method includes computing, by the managing computing device, a shared representation of the datasets based on the subset of the list of unique objects and a shared function having one or more shared parameters. Even further, the method includes determining, by the managing computing device, a sublist of objects for the respective dataset of each client computing device based on an intersection of the subset of identifiers with the list of identifiers for the respective dataset. Yet further, the method includes determining, by the managing computing device, a partial representation for the respective dataset of each client computing device based on the sublist of objects for the respective dataset and the shared representation. Still further, the method includes transmitting, by the managing computing device, to each of the client computing devices: the sublist of objects for the respective dataset and the partial representation for the respective dataset. Even still further, the method includes receiving, by the managing computing device, one or more feedback values from at least one of the client computing devices. The one or more feedback values are determined by the client computing devices by determining, by the respective client computing device, a set of predicted values corresponding to the respective dataset. The set of predicted values is based on the partial representation and an individual function with one or more individual parameters corresponding to the respective dataset. The one or more feedback values are also determined by the client computing devices by determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset. Further, the one or more feedback values are determined by the client computing devices by updating, by the respective client computing device, the one or more individual parameters for the respective dataset. The one or more feedback values are additionally determined by the client computing devices by determining, by the respective client computing device, the one or more feedback values. The one or more feedback values are used to determine a change in the partial representation that corresponds to an improvement in the set of predicted values. Even yet further, the method includes determining, by the managing computing device, based on the sublists of objects and the one or more feedback values from the client computing devices one or more aggregated feedback values. Still even further, the method includes updating, by the managing computing device, the one or more shared parameters based on the one or more aggregated feedback values. Still yet even further, the method includes computing, by the managing computing device, an updated shared representation of the datasets based on the shared function and the one or more updated shared parameters. The updated shared representation corresponds to the optimized model.

In a thirteenth aspect, the disclosure describes a method for machine learning, comprising: receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects; determining, by the managing computing device, a respective list of identifiers for each dataset and a composite list of identifiers comprising a combination of the lists of identifiers of each dataset of the plurality of datasets; determining, by the managing computing device, a set of unique objects from among the plurality of datasets; selecting, by the managing computing device, a subset of identifiers from the composite list of identifiers; determining, by the managing computing device, a subset of the set of unique objects corresponding to each identifier in the subset of identifiers; computing, by the managing computing device, a shared representation of the datasets based on the subset of the set of unique objects and a shared function having one or more shared parameters; determining, by the managing computing device, a subset of objects for the respective dataset of each client computing device based on an intersection of the subset of identifiers with the list of identifiers for the respective dataset; determining, by the managing computing device, a partial representation for the respective dataset of each client computing device based on the subset of objects for the respective dataset and the shared representation; acquiring, by the managing computing device, one or more feedback values, wherein each of the one or more feedback values is determined as a change in the partial representation that corresponds to an improvement in a set predicted values as compared to the set of recorded values for the respective dataset; determining, by the managing computing device, based on the subsets of objects and the one or more feedback values from the client computing devices, one or more aggregated feedback values; and updating, by the managing computing device, the one or more shared parameters based on the one or more aggregated feedback values.

In a fourteenth aspect, the disclosure describes a method for machine learning, comprising: transmitting, by a first client computing device to a managing computing device, a first dataset corresponding to the first client computing device, wherein the first dataset is one of a plurality of datasets transmitted to the managing computing device by a plurality of client computing devices, wherein each dataset corresponds to a set of recorded values, and wherein each dataset comprises objects; receiving, by the first client computing device, a first subset of objects for the first dataset and a first partial representation for the first dataset, wherein the first subset of objects is a subset of the objects of the first dataset being part of forming a shared representation of the plurality of datasets, the shared representation being defined by a shared function having one or more shared parameters, and the partial representation for the first dataset is based on the first subset of objects and the shared representation; determining, by the first client computing device, a first set of predicted values corresponding to the first dataset, wherein the first set of predicted values is based on the first partial representation and a first individual function with one or more first individual parameters corresponding to the first dataset; determining, by the first client computing device, a first error for the first dataset based on a first individual loss function for the first dataset, the first set of predicted values corresponding to the first dataset, the first subset of objects, and non-empty entries in the set of recorded values corresponding to the first dataset; updating, by the first client computing device, the one or more first individual parameters for the first dataset; determining, by the first client computing device, one or more feedback values, wherein the one or more feedback values are used to determine a change in the first partial representation that corresponds to an improvement in the first set of predicted values; and transmitting, by the first client computing device to the managing computing device, the one or more feedback values, wherein the one or more feedback values are usable by the managing computing device along with subsets of objects from the plurality of client computing devices to determine one or more aggregated feedback values, and wherein the one or more aggregated feedback values are usable by the managing computing device to update the one or more shared parameters.

According to one or more of the above aspects, machine learning based on a plurality of datasets is provided. This implies that a plurality of sources may be used for obtaining training data, such that a robust and reliable machine-learned model may be formed. The machine learning according to at least some of the aspects enables datasets to be provided from a plurality of sources without data dissipating from one source to another. Thus, even though a client computing device may provide a dataset relating to private data in order to train the model, the machine learning may be set up such that the private data will not be shared to unauthorized parties, such as competitors that are also providing datasets to the machine learning.

The shared representation is determined based on the plurality of datasets from respective client computing devices. Thus, a shared representation for the datasets may be formed, which shared representation may contribute to forming a model for each of the plurality of datasets. The shared representation may be based on a shared function being shared for the plurality of datasets for representing relations between objects and features in the datasets. Thus, the shared function may be determined based on a plurality of datasets, enabling the shared function to be determined in a robust and reliable manner. Further, thanks to the partial representations being determined, the contribution of each dataset to forming of the shared representation may be extracted. Thus, the client computing devices may receive back only the partial representation relating to the dataset provided by the respective client computing device. This implies that the client computing device may benefit from the use of the plurality of datasets in forming of a robust model of the shared function, while the client computing device does not receive information of the full shared representation, so that the client computing device does not receive any information of relations between objects and features which are not deducible from the dataset provided by the client computing device (e.g. relating to features not present in the dataset of the client computing device).

Hence, a client computing device providing datasets to the managing computing device will not share sensitive data with other client computing devices. In fact, the client computing devices may even strip the datasets from sensitive information, so that the datasets may be provided in an encoded format. The datasets may provide information of relations between objects and features, but the managing computing device may not know what physical properties the objects and features represent. Corporations desiring to benefit from the secure machine learning method may have a (secret) agreement on a format in which the datasets are provided, such that the datasets have a common format enabling the managing computing device to determine the shared representation without knowing what physical properties the objects and features represent.

Hence, as set out above, the use of a managing computing device for determining the shared representation enables client computing devices to provide datasets without compromising sensitive data. Thus, although implementation of a machine learning method may very well be within competence of a host for the client computing device, the datasets may be provided from the client computing devices to the managing computing device for computing the shared representation so as to benefit from a large set of training data.

However, it should also be realized that, in some embodiments, the host of the client computing device may not have competence or resources to implement a machine learning method. Thus, the managing computing device may be used for providing a possibility to create a machine-learned model to predict relations between objects and features, where a client computing device would otherwise not be able to make such predictions. In such case, sensitivity of data may not be as important, and the managing computing device may be configured to generate an individual function with one or more individual parameters corresponding to the respective dataset. Thus, the managing computing device may not only develop the one or more shared parameters of the shared function, but may also develop the individual function corresponding to the respective dataset.

For example, the client computing devices may relate to online stores, wherein the store wants to provide suggestions on merchandise to a user based on a machine learning method. The managing computing device may thus use datasets of a plurality of client computing devices in order to provide a robust determination of the shared function. However, the client computing devices may not want to completely share the information of their datasets. Thus, the managing computing device may develop the individual function for the respective dataset, such that each client computing device benefits from the plurality of datasets in forming of the shared function, while even though the managing computing device has access to data of all the datasets there is still an individual function formed for the respective client computing devices based on the contribution of the dataset of the respective client computing device.

Thus, as set out above, the acquiring, by the managing computing device, of one or more feedback values may be achieved by the managing computing device transmitting information to the client computing devices and the client computing devices determining the one or more feedback values. However, as an alternative, the one or more feedback values may be acquired by the managing computing device applying an individual function for the respective dataset to the partial representation of the respective dataset.

According to an embodiment, each dataset comprises objects in a plurality of dimensions, and the objects in at least one of the plurality of dimensions for each of the datasets is of a same type. This implies that the datasets comprise corresponding information such that the managing computing device may easily determine shared relations between the objects so as to form the shared representation. However, it should be realized that different object types may still be used by the managing computing device to develop a shared representation. In some embodiments, using different object types may include normalizing values corresponding to different object types.

According to an embodiment, the respective list of identifiers for each dataset corresponds to a set of objects for each dataset, wherein the identifiers for the plurality of datasets are defined according to a common syntax. This may imply that identifiers for the respective datasets are determined in the same way so that the managing computing device may determine identical identifiers for identical objects. This may ensure that the managing computing device may easily form identical identifiers for identical objects so that a combined list of identifiers may be formed wherein unique objects may be easily identified. The managing computing device may provide information on the common syntax to the client computing devices in order to ensure that the client computing devices provide the datasets in a desired format. However, according to an alternative, the client computing devices may agree on a common syntax without the managing computing device. This implies that the client computing devices may provide the datasets in a format, which does not provide information of what physical properties the objects and features represent, but the client computing devices may ensure that the datasets are provided in a common manner allowing the managing computing device to still determine the shared representation.

A client computing device may be set up to determine feedback values for improving the shared parameters. Since the shared representation is based on a plurality of datasets, the partial representation for a client computing device may predict values for objects, where no recorded value exists. Thus, the client computing device may be configured to only take into account non-empty entries in the set of recorded values for determining the error for the dataset, even though predicted values may be available for further entries.

The managing computing device may be configured to transmit the partial representation to the client computing device in order to ensure that the client computing device only receives model information applying to the data provided by the client computing device. However, it should be realized that in some embodiments, secrecy of data in the datasets may not be of high importance and the client computing devices may be willing to share data. In such case, the managing computing device may be configured to transmit the shared representation to each of the client computing devices, such that the partial representation may be determined in the client computing device and that processing of data for determining of the partial representation may be distributed to the client computing devices. This may ensure that a speed of processing may be increased, especially if a large number of client computing devices are providing datasets for the shared representation, as the determining of the partial representations may be distributed to a plurality of client computing devices, which may in parallel determine the partial representations. The managing computing device may be configured to transmit the shared representation, the subset of identifiers and the list of identifiers for the respective dataset to the respective client computing devices in order to enable the client computing devices to determine the respective partial representations.

Thus, in a fifteenth aspect, the disclosure describes a method for machine learning, comprising: receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects; determining, by the managing computing device, a respective list of identifiers for each dataset and a composite list of identifiers comprising a combination of the lists of identifiers of each dataset of the plurality of datasets; determining, by the managing computing device, a set of unique objects from among the plurality of datasets; selecting, by the managing computing device, a subset of identifiers from the composite list of identifiers; determining, by the managing computing device, a subset of the set of unique objects corresponding to each identifier in the subset of identifiers; computing, by the managing computing device, a shared representation of the datasets based on the subset of the set of unique objects and a shared function having one or more shared parameters; transmitting, by the managing computing device, to each of the client computing devices: the shared representation, the subset of identifiers and the list of identifiers for the respective dataset; receiving, by the managing computing device, one or more feedback values, from at least one of the client computing devices, wherein each of the one or more feedback values is determined as a change in the partial representation that corresponds to an improvement in a set predicted values as compared to the set of recorded values for the respective dataset; determining, by the managing computing device, based on the subsets of objects and the one or more feedback values from the client computing devices, one or more aggregated feedback values; and updating, by the managing computing device, the one or more shared parameters based on the one or more aggregated feedback values.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 5A illustrates a dataset and a set of predicted values, according to example embodiments.

FIG. 5B illustrates a dataset and a set of predicted values, according to example embodiments.

FIG. 6A illustrates a list of identifiers for a dataset, according to example embodiments.

FIG. 6B illustrates a list of identifiers for a dataset, according to example embodiments.

FIG. 14B illustrates an individual function, according to example embodiments.

FIG. 16A illustrates a dataset and a set of recorded values, according to example embodiments.

FIG. 16B illustrates a dataset and a set of recorded values, according to example embodiments.

FIG. 16C illustrates a dataset and a set of recorded values, according to example embodiments.

FIG. 17A illustrates a matrix factorization algorithm, according to example embodiments.

FIG. 18A illustrates a dataset and a set of predicted values, according to example embodiments.

FIG. 18B illustrates a dataset and a set of predicted values, according to example embodiments.

FIG. 19A illustrates a list of identifiers for a dataset, according to example embodiments.

FIG. 19B illustrates a list of identifiers for a dataset, according to example embodiments.

DETAILED DESCRIPTION

Figure 1:
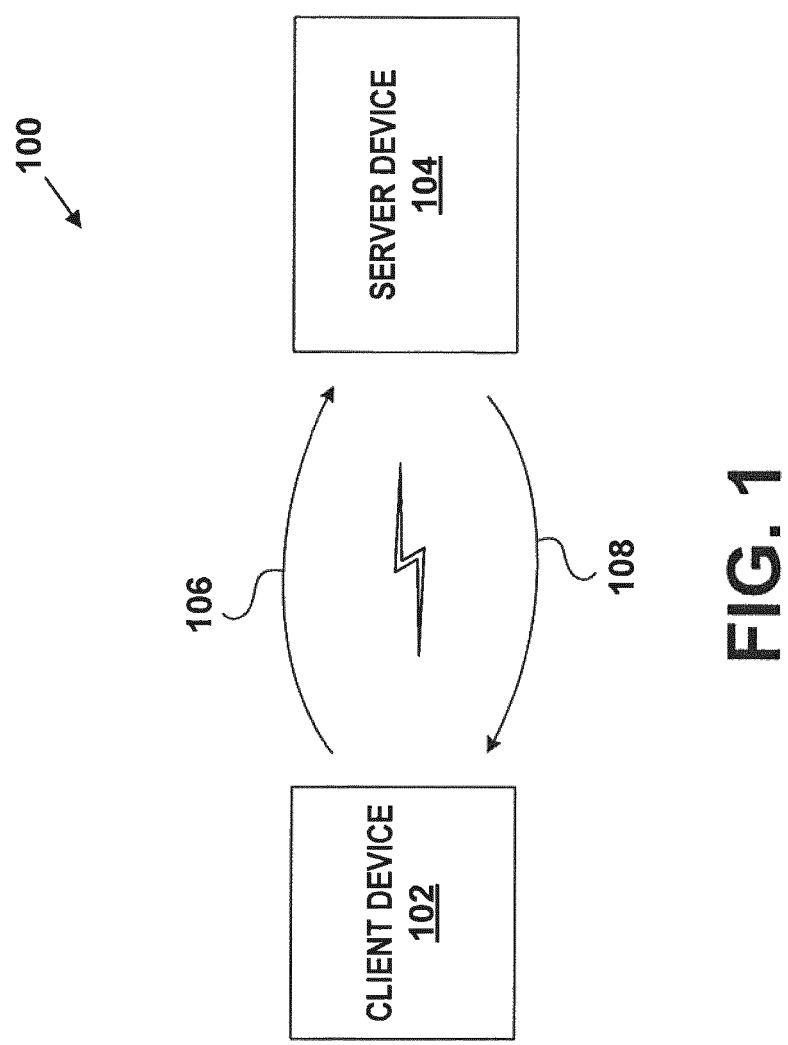
FIG. 1 is a high-level illustration of a client-server computing system, according to example embodiments.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. In addition, some of the illustrated elements may be combined or omitted. Similarly, an example embodiment may include elements that are not illustrated in the figures.

I. OVERVIEW

Example embodiments relate to secure broker-mediated data analysis and prediction. The secure broker-mediated data analysis and prediction may be used to develop a machine learning model (e.g., an artificial neural network) using private data from multiple parties without revealing the private data of one party to another party. One example embodiment described herein relates to a method.

The method may include a managing computing device (e.g., a server) transmitting data to and receiving data from a plurality of client computing devices. The data may be transmitted to and received from the plurality of client computing devices to develop a machine learning model. For example, the managing computing device may receive multiple datasets from multiple client computing devices. Subsequently, the managing computing device may use these datasets to establish an initial version of the machine learning model (e.g., based on a function with initial parameters).

Then, the managing computing device may transmit different portions of the initial version of the machine learning model to different client computing devices. In some embodiments, the managing computing device may send the entire model to the client computing devices, as well as indications of which portion corresponds to a respective client computing device's dataset. Subsequently, the respective client computing device may extract the appropriate portion of the model from the entire model. Upon receiving/extracting a portion of the machine learning model that corresponds to the respective client computing device, each client computing device may update a local machine learning model that is stored within the respective client computing device. Then, each client computing device may use the updated local machine learning model to make a prediction (e.g., compute a set of predicted or expected values).

Upon making the prediction, the respective client computing device may compare the prediction to a set of recorded values stored within the client computing device. Based on the comparison, the client computing device may determine one or more errors with the prediction (and therefore one or more errors with the updated local machine learning model on which the prediction was based). In some embodiments, such errors may be calculated using a loss function. Based on the errors and the portion of the entire machine learning model that corresponds to the respective client computing device, the client computing device may transmit one or more feedback values to the managing computing device indicating that there is an error in a respective portion of the entire machine learning model. Similar feedback may be provided to the managing computing device by one, multiple, or all client computing devices.

Upon receiving the feedback from the client computing devices, the managing computing device may then update the entire machine learning model (e.g., including the function and the parameters) based on the feedback. In such a scenario, the entire machine learning model may be improved and/or refined. The steps outlined above of transmitting portions of the model to the client computing devices, having the client computing devices make and evaluate predictions based on the portions of the model, and then receiving feedback from the client computing devices may be repeated for multiple iterations until the entire machine learning model can no longer be improved (e.g., the predictions made by each client computing device have no error) or until the improvement between each iteration is below a threshold value of improvement (e.g., the errors in the predictions made by each client computing device do not substantially change from one iteration to the next).

Once the training of the entire machine learning model is complete (e.g., the improvement between subsequent iterations is below a threshold value), the machine learning model can be used to make predictions or recommendations. For example, the managing computing device could utilize the machine learning model to make predictions based on future events. Additionally or alternatively, once the model is trained, the entire machine learning model (or a portion thereof) may be transmitted to one or more of the client computing devices by the managing computing device. At this point, at least one of the one or more client computing devices may utilize the model to make predictions or recommendations (e.g., recommend a book to one of its users based on the machine learning model). Still further, the model could also be transmitted to one or more third parties who did not provide data used in the training of the machine learning model. Such third parties may be required to pay a fee, join a subscription service, view an advertisement, or log in with validation credentials before being able to view and/or utilize the machine learning model. Additionally, the third parties may utilize the machine learning model make predictions or recommendations based on their own data (e.g., data other than the data provided to the managing computing device in the training of the machine learning model).

II. EXAMPLE SYSTEMS

The following description and accompanying drawings will elucidate features of various example embodiments. The embodiments provided are by way of example, and are not intended to be limiting. As such, the dimensions of the drawings are not necessarily to scale.

FIG. 1 illustrates an example communication system 100 for carrying out one or more of the embodiments described herein. Communication system 100 may include computing devices. As described herein, a "computing device" may refer to either a client device, a server device (e.g., a stand-alone server computer or networked cluster of server equipment), or some other type of computational platform.

Client device 102 may be any type of device including a personal computer, laptop computer, a wearable computing device, a wireless computing device, a head-mountable computing device, a mobile telephone, or tablet computing device, etc., that is configured to transmit data 106 to and/or receive data 108 from a server device 104 in accordance with the embodiments described herein. For example, in FIG. 1, client device 102 may communicate with server device 104 via one or more wireline or wireless interfaces. In some cases, client device 102 and server device 104 may communicate with one another via a local-area network. Alternatively, client device 102 and server device 104 may each reside within a different network, and may communicate via a wide-area network, such as the Internet. In some embodiments, the client device 102 may correspond to a "client computing device." Further, in some embodiments, the communication system 100 may include multiple client devices 102. Additionally or alternatively, one or more "client computing devices" may include computing components more similar to the server device 104 than the client device 102. In other words, in some embodiments, multiple server devices 104 may communicate with one another, rather than a single server device 104 communicating with a single client device 102.

Client device 102 may include a user interface, a communication interface, a main processor, and data storage (e.g., memory). The data storage may contain instructions executable by the main processor for carrying out one or more operations relating to the data sent to, or received from, server device 104. The user interface of client device 102 may include buttons, a touchscreen, a microphone, and/or any other elements for receiving inputs, as well as a speaker, one or more displays, and/or any other elements for communicating outputs.

Server device 104 may be any entity or computing device arranged to carry out the server operations described herein. Further, server device 104 may be configured to send data 108 to and/or receive data 106 from the client device 102. In some embodiments, the server device 104 may correspond to a "managing computing device" (e.g., a "broker"). Additionally or alternatively, in some embodiments, the server device 104 may correspond to one or more "client computing devices" (e.g., a "data-supplying party").

Data 106 and data 108 may take various forms. For example, data 106 and 108 may represent packets transmitted by client device 102 or server device 104, respectively, as part of one or more communication sessions. Such a communication session may include packets transmitted on a signaling plane (e.g., session setup, management, and teardown messages), and/or packets transmitted on a media plane (e.g., text, graphics, audio, and/or video data).

Regardless of the exact architecture, the operations of client device 102, server device 104, as well as any other operation associated with the architecture of FIG. 1, can be carried out by one or more computing devices. These computing devices may be organized in a standalone fashion, in cloud-based (networked) computing environments, or in other arrangements.

Figure 2:
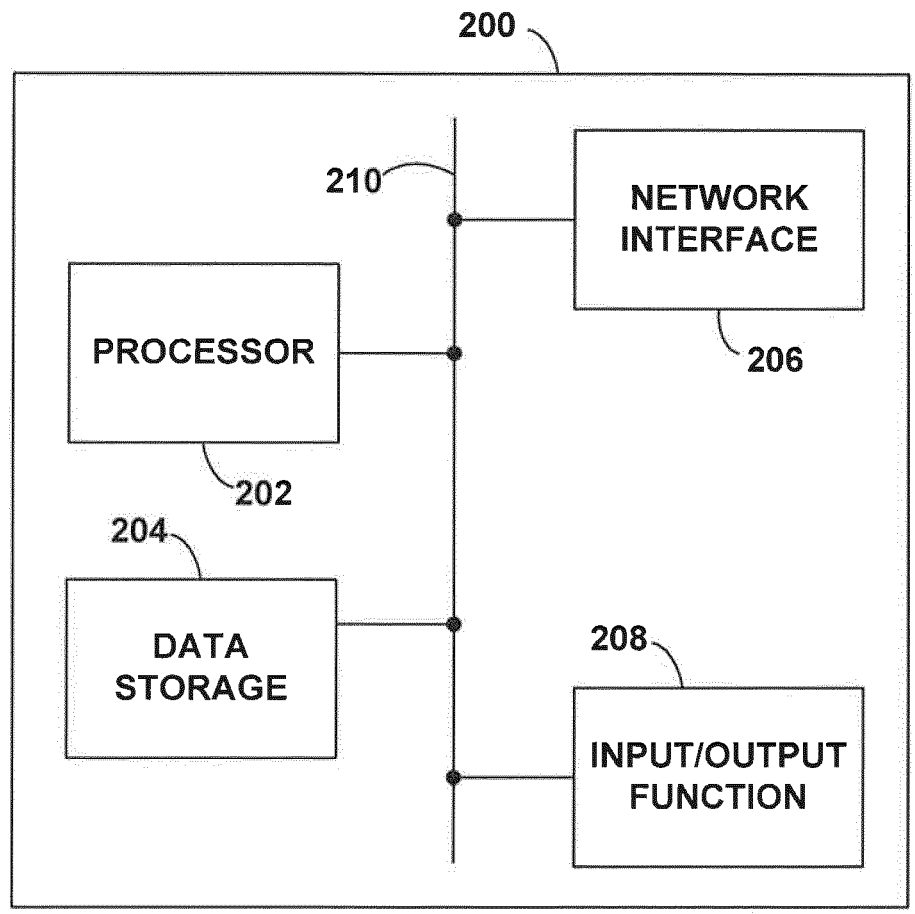
FIG. 2 is a schematic illustration of a computing device, according to example embodiments.

FIG. 2 is a simplified block diagram exemplifying a computing device 200, illustrating some of the functional components that could be included in a computing device arranged to operate in accordance with the embodiments herein. Example computing device 200 could be a client device, a server device, or some other type of computational platform. For illustrative purposes, this specification may equate computing device 200 to a server device 104 and/or a client device 102 from time to time. Nonetheless, the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more CPUs, such as one or more general purpose processors and/or one or more dedicated processors (e.g., application specific integrated circuits (ASICs), digital signal processors (DSPs), network processors, etc.).

Data storage 204, in turn, may include volatile and/or non-volatile data storage devices and can be integrated in whole or in part with processor 202. Data storage 204 can hold program instructions, executable by processor 202, and data that may be manipulated by such program instructions to carry out the various methods, processes, or operations described herein. Alternatively, these methods, processes, or operations can be defined by hardware, firmware, and/or any combination of hardware, firmware, and software. By way of example, the data in data storage 204 may contain program instructions, perhaps stored on a non-transitory, computer-readable medium, executable by processor 202 to carry out any of the methods, processes, or operations disclosed in this specification or the accompanying drawings. The data storage 204 may include non-volatile memory (e.g., a read-only memory, ROM) and/or volatile memory (e.g., random-access memory, RAM), in various embodiments. For example, the data storage 204 may include a hard drive (e.g., hard disk), flash memory, a solid-state drive (SSD), electrically erasable programmable read-only memory (EEPROM), dynamic random-access memory (DRAM), and/or static random-access memory (SRAM). It will be understood that other types of transitory or non-transitory data storage devices are possible and contemplated within the scope of the present disclosure.

Network interface 206 may take the form of a wireline connection, such as an Ethernet, Token Ring, or T-carrier connection. Network interface 206 may also take the form of a wireless connection, such as IEEE 802.11 (WiFi), BLUETOOTH®, BLUETOOTH LOW ENERGY (BLE)®, or a wide-area wireless connection. However, other forms of physical layer connections and other types of standard or proprietary communication protocols may be used over network interface 206. Furthermore, network interface 206 may include multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 3:
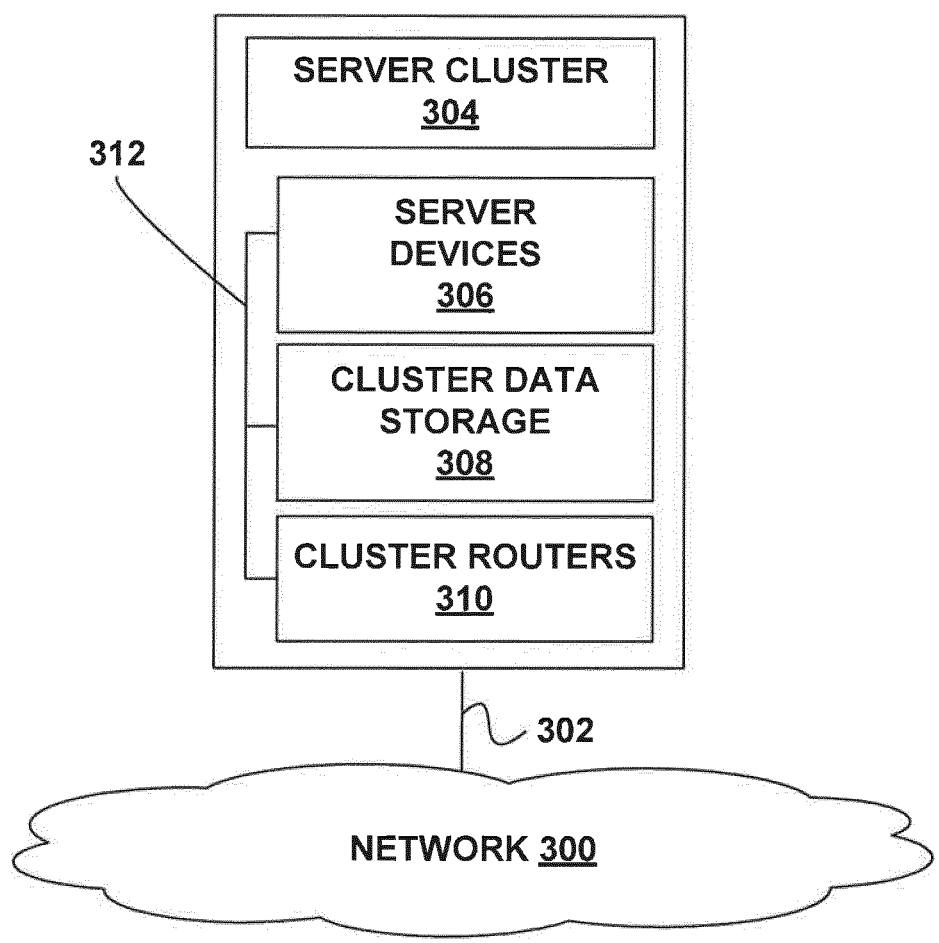
FIG. 3 is a schematic illustration of a networked server cluster, according to example embodiments.

FIG. 3 depicts a cloud-based server cluster 304 in accordance with an example embodiment. In FIG. 3, functions of a server device, such as server device 104 (as exemplified by computing device 200) may be distributed between server devices 306, cluster data storage 308, and cluster routers 310, all of which may be connected by local cluster network 312. The number of server devices, cluster data storages, and cluster routers in server cluster 304 may depend on the computing task(s) and/or applications assigned to server cluster 304.

For example, server devices 306 can be configured to perform various computing tasks of computing device 200. Thus, computing tasks can be distributed among one or more of server devices 306. To the extent that these computing tasks can be performed in parallel, such a distribution of tasks may reduce the total time to complete these tasks and return a result. For purpose of simplicity, both server cluster 304 and individual server devices 306 may be referred to as "a server device." This nomenclature should be understood to imply that one or more distinct server devices, data storage devices, and cluster routers may be involved in server device operations.

Cluster data storage 308 may be data storage arrays that include disk array controllers configured to manage read and write access to groups of hard disk drives. The disk array controllers, alone or in conjunction with server devices 306, may also be configured to manage backup or redundant copies of the data stored in cluster data storage 308 to protect against disk drive failures or other types of failures that prevent one or more of server devices 306 from accessing units of cluster data storage 308.

Cluster routers 310 may include networking equipment configured to provide internal and external communications for the server clusters. For example, cluster routers 310 may include one or more packet-switching and/or routing devices configured to provide (i) network communications between server devices 306 and cluster data storage 308 via cluster network 312, and/or (ii) network communications between the server cluster 304 and other devices via communication link 302 to network 300.

Additionally, the configuration of cluster routers 310 can be based at least in part on the data communication requirements of server devices 306 and cluster data storage 308, the latency and throughput of the local cluster networks 312, the latency, throughput, and cost of communication link 302, and/or other factors that may contribute to the cost, speed, fault-tolerance, resiliency, efficiency and/or other design goals of the system architecture.

As a possible example, cluster data storage 308 may include any form of database, such as a structured query language (SQL) database. Various types of data structures may store the information in such a database, including but not limited to tables, arrays, lists, trees, and tuples. Furthermore, any databases in cluster data storage 308 may be monolithic or distributed across multiple physical devices.

Server devices 306 may be configured to transmit data to and receive data from cluster data storage 308. This transmission and retrieval may take the form of SQL queries or other types of database queries, and the output of such queries, respectively. Additional text, images, video, and/or audio may be included as well. Furthermore, server devices 306 may organize the received data into web page representations. Such a representation may take the form of a markup language, such as the hypertext markup language (HTML), the extensible markup language (XML), or some other standardized or proprietary format. Moreover, server devices 306 may have the capability of executing various types of computerized scripting languages, such as but not limited to Perl, Python, PHP Hypertext Preprocessor (PHP), Active Server Pages (ASP), JavaScript, and so on. Computer program code written in these languages may facilitate the provision of web pages to client devices, as well as client device interaction with the web pages.

Figure 4A:
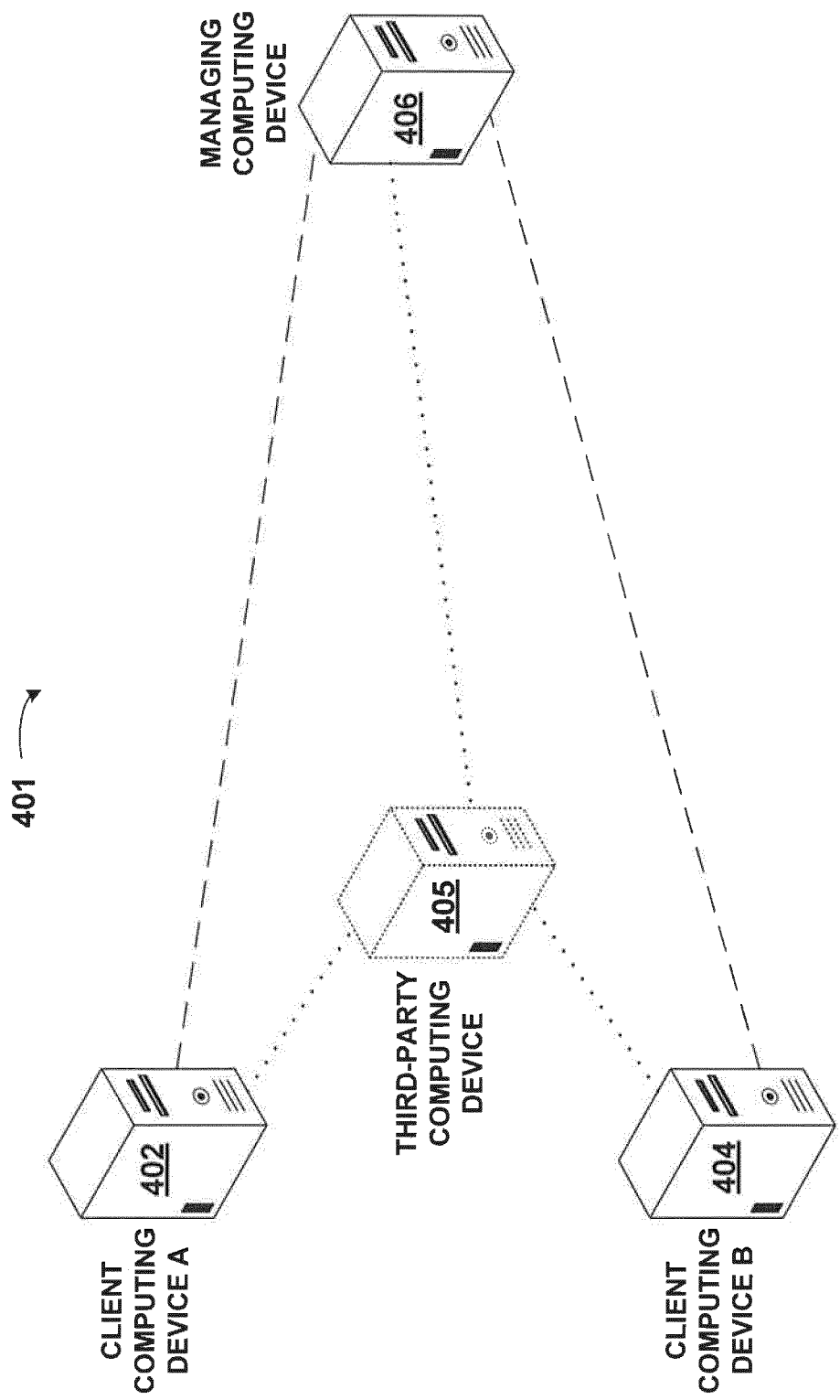
FIG. 4A illustrates a schematic drawing of a network including client computing devices and a managing computing device, according to example embodiments.

FIG. 4A is an illustration of a computing network 401. The computing network 401 may include client computing device A 402, client computing device B 404, and a managing computing device 406 (in some embodiments, the managing computing device 406 may be additionally or alternatively referred to as a "broker"). Optionally, in some embodiments the computing network 401 may also include a third-party computing device 405. As described above, each of client computing device A 402, client computing device B 404, the third-party computing device 405 and the managing computing device 406 may be a server device (e.g., the server device 104 of FIG. 1) or a client device (e.g., the client device 102 of FIG. 1). For example, in some embodiments, all components in FIG. 4A may be server devices communicating with one another. In other embodiments, all components in FIG. 4A may be client devices communicating with one another. In still other embodiments, some component(s) may be client devices, while other component(s) are server devices (e.g., the managing computing device 406 is a server device, while client computing device A 402, client computing device B 404, and the third-party computing device 405 are client devices).

The dashed lines in FIG. 4A illustrate communicative couplings between computing components. As illustrated, client computing device A 402 may be communicatively coupled to the managing computing device 406. Similarly, client computing device B 402 may also be communicatively coupled to the managing computing device 406. Further, in embodiments including a third-party computing device 405, the dotted lines indicate potential communicative couplings between computing components (e.g., the third-party computing device 405 may be communicatively coupled to any subset of client computing A 402, client computing device B 404, and the managing computing device 406). Such communicative couplings may occur using a variety of technologies (e.g., over WiFi, over BLUETOOTH®, over the public Internet, etc.).

Also as illustrated, client computing device A 402 and client computing device B 404 may be communicatively uncoupled from one another. In this way, privacy of communications between a respective client computing device and the managing computing device 406 may be preserved. In some embodiments, additional technologies to preserve privacy may be implemented (e.g., a private key/public key encryption mechanism for communications between a client computing device and the managing computing device 406).

In alternate embodiments, client computing device A 402 and client computing device B 404 may be communicatively coupled to one another. This may allow a sharing of some or all of a client computing device's data with another client computing device. In still other embodiments, there may be any number of client computing devices communicating with the managing computing device 406 (e.g., more than two client computing devices). For example, three or more client computing devices may provide data to and receive data from the managing computing device 406.

In an example embodiment, the third-party computing device 405 need not be directly involved in the determination of a machine learning model (e.g., shared representation U) as described with regard to method 400 herein. In such scenarios, third-party computing device 405 need not carry out all of the operations of method 400, as described herein. Rather, the third-party computing device 405 could be a recipient of information based on the machine learning model determined using other operations of method 400.

III. EXAMPLE PROCESSES

In various embodiments described herein, some operations are described as being performed by managing computing device(s) and/or client computing device(s). It is understood that operations performed by a single managing computing device could be spread over multiple managing computing devices (e.g., to decrease computational time). Similarly, operations performed by a single client computing device could instead be performed by a collection of computing devices that are each part of the single client computing device. Even further, multiple operations are described herein as being performed by a client computing device (e.g., client computing device A 402). It is also understood that any operation performed on a single client computing device could, but need not, be mirrored and performed on one or more other client computing devices (e.g., for respective datasets/sets of recorded values). Similarly, some operations are described herein as being performed by multiple client computing devices, but it is understood that in alternate embodiments, only one client computing device may perform the operation (e.g., transmitting one or more feedback values to the managing computing device may only be performed by one client computing device, in some embodiments). Even further, some client computing devices may store multiple datasets and/or multiple sets of recorded values, and therefore may perform actions corresponding to multiple computing devices disclosed herein. Still further, in some embodiments, the managing computing device may be integrated with one or more of the client computing devices (e.g., depending on the level of privacy required by the interacting parties/client computing devices).

The methods and systems described herein may be described using mathematical syntax (e.g., to represent variables in order to succinctly describe processes). It is understood that a variety of mathematical syntax, including mathematical syntax different than used herein, supplemental to used herein, or no mathematical syntax at all, may be employed when describing the methods and systems disclosed herein. Further, it is understood that the mathematical syntax employed may be based on the given machine-learning model used (e.g., syntax used to represent an artificial neural network model may be different than syntax used to represent a support vector machine model). By way of example, the following table summarizes the mathematical syntax used herein to illustrate the methods and systems of the disclosure (e.g., the mathematical syntax used in reference to FIGS. 4B-15B):

| Variable | Description of Variable |
| --- | --- |
| U | Shared Representation |
| f | Shared Function |
| β | One or More Shared Parameters |
| $\bar{\beta}$ | Weight Tensor Representing the One or More Shared Parameters |
| $X_A$ | Dataset A |
| $X_B$ | Dataset B |
| d | Number of Dimensions in a Dataset |
| $Y_A$ | Set of Recorded Values Corresponding to Dataset A |
| $Y_B$ | Set of Recorded Values Corresponding to Dataset B |
| $M_A$ | List of Identifiers for Dataset A |
| $M_B$ | List of Identifiers for Dataset B |
| $M_{Comb}$ | Composite List of Identifiers |
| $X_{Comb}$ | List of Unique Objects |
| S | Subset of Identifiers |
| Z | Subset of the List of Unique Objects |
| $S_A$ | Sublist of Objects for Dataset A |
| $S_B$ | Sublist of Objects for Dataset B |
| $U_A$ | Partial Representation for Dataset A |
| $U_B$ | Partial Representation for Dataset B |
| $\hat{Y}_A$ | Set of Predicted Values Corresponding to Dataset A |
| $\hat{Y}_B$ | Set of Predicted Values Corresponding to Dataset B |
| $g_A$ | Individual Function Corresponding to Dataset A |
| $g_B$ | Individual Function Corresponding to Dataset B |
| $\gamma_A$ | One or More Individual Parameters Corresponding to Dataset A |
| $\gamma_B$ | One or More Individual Parameters Corresponding to Dataset B |
| $\bar{\gamma}_i$ | Weight Tensor Representing the One or More Individual Parameters |
| $E_A$ | Error for Dataset A |
| $E_B$ | Error for Dataset B |
| $L_A$ | Individual Loss Function for Dataset A |
| $L_B$ | Individual Loss Function for Dataset B |
| $W_A$ | Non-Empty Entries in the Set of Recorded Values for Dataset A |
| $W_B$ | Non-Empty Entries in the Set of Recorded Values for Dataset B |
| $C_A$ | One or More Feedback Values Corresponding to Dataset A |
| $C_B$ | One or More Feedback Values Corresponding to Dataset B |
| $C_{Comb}$ | One or More Aggregated Feedback Values |
| $U_{Final}$ | Final Shared Representation |
| $\hat{Y}_{A_{Final}}$ | Final Set of Predicted Values Corresponding to Dataset A |
| $\hat{Y}_{B_{Final}}$ | Final Set of Predicted Values Corresponding to Dataset B |
| $U_{Final\_A}$ | Final Partial Representation for Dataset A |
| $U_{Final\_B}$ | Final Partial Representation for Dataset B |
| $\overline{FLN}$ | Tensor Representing Values for First-Level Neurons |
| $\overline{MLN}$ | Tensor Representing the Values for Mid-Level Neurons |
| $\overline{ULN}$ | Tensor Representing Values for Upper-Level Neurons |
| $I_A$ | Individual Representation for Dataset A |
| $I_B$ | Individual Representation for Dataset B |
| $R_A$ | Individual Learning Rate Corresponding to Dataset A |
| $R_B$ | Individual Learning Rate Corresponding to Dataset B |
| η | Shared Learning Rate |
| $\overline{C}_A$ | Feedback Tensor Corresponding to Dataset A |
| $\overline{C}_B$ | Feedback Tensor Corresponding to Dataset B |
| $\overline{C}_{Comb}$ | Tensor Representing the One or More Aggregated Feedback Values |

Figure 4B:
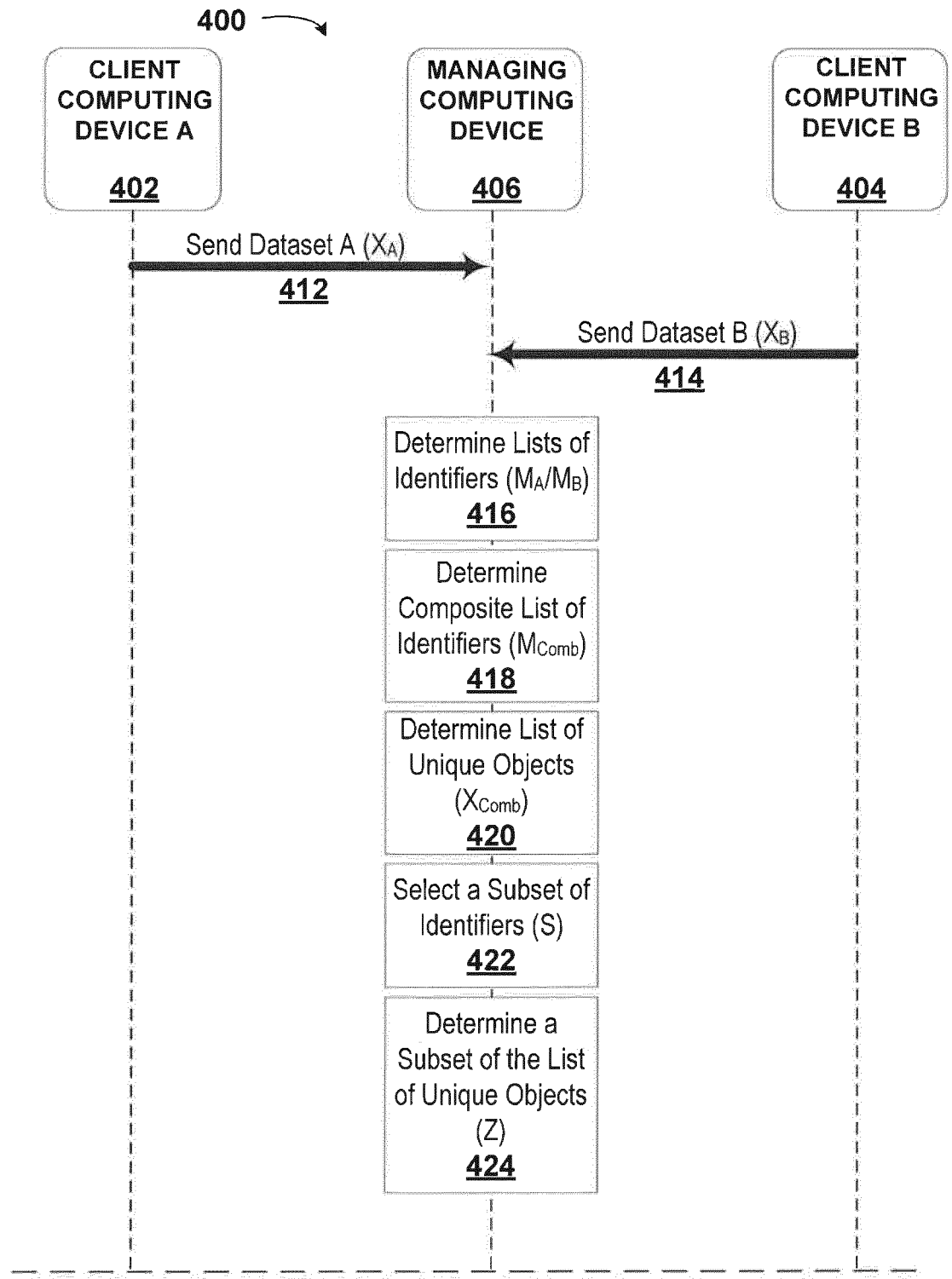
FIG. 4B is a data flow diagram of a portion of a method, according to example embodiments.
Figure 4C:
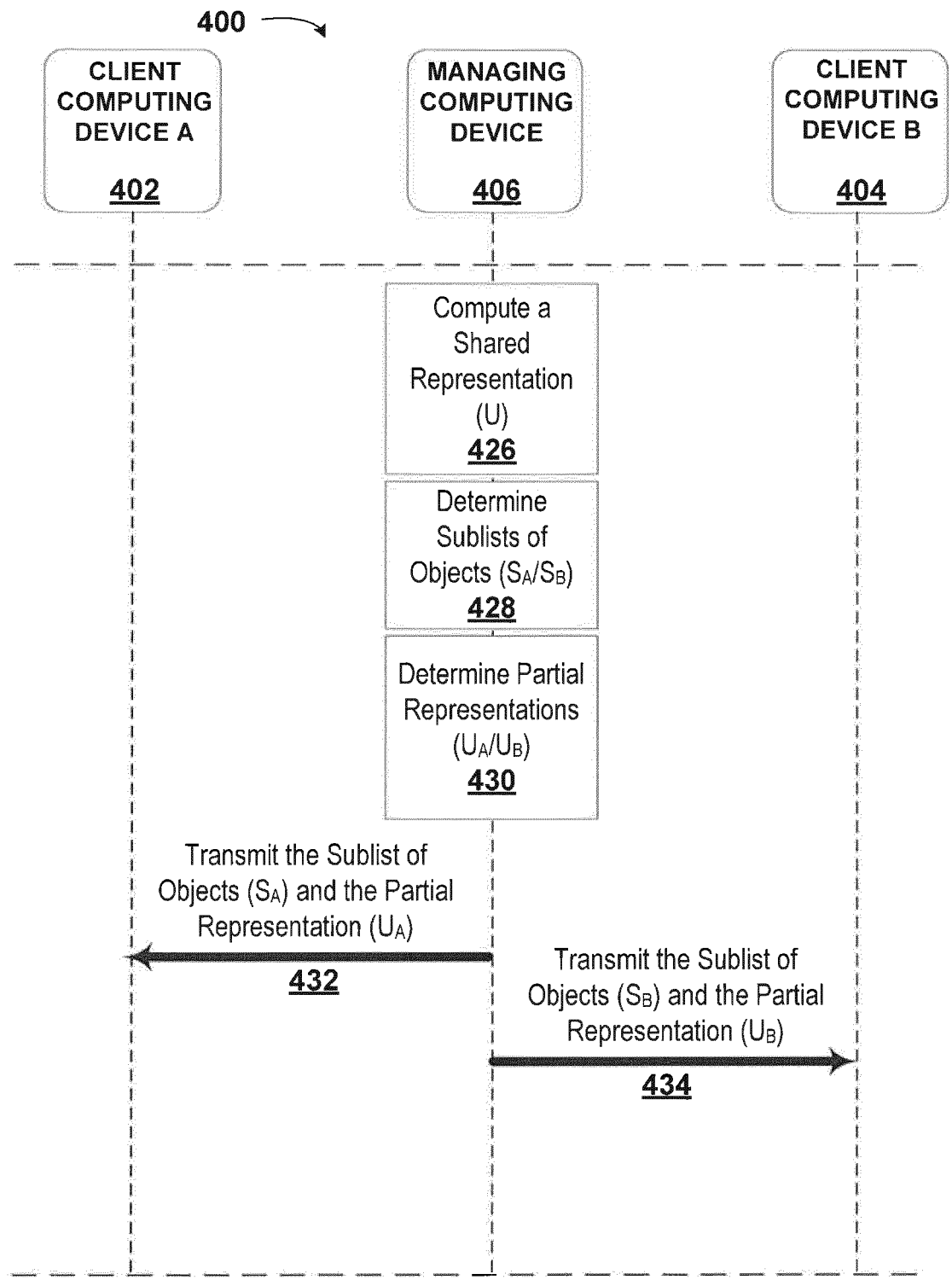
FIG. 4C is a data flow diagram of a portion of a method, according to example embodiments.
Figure 4D:
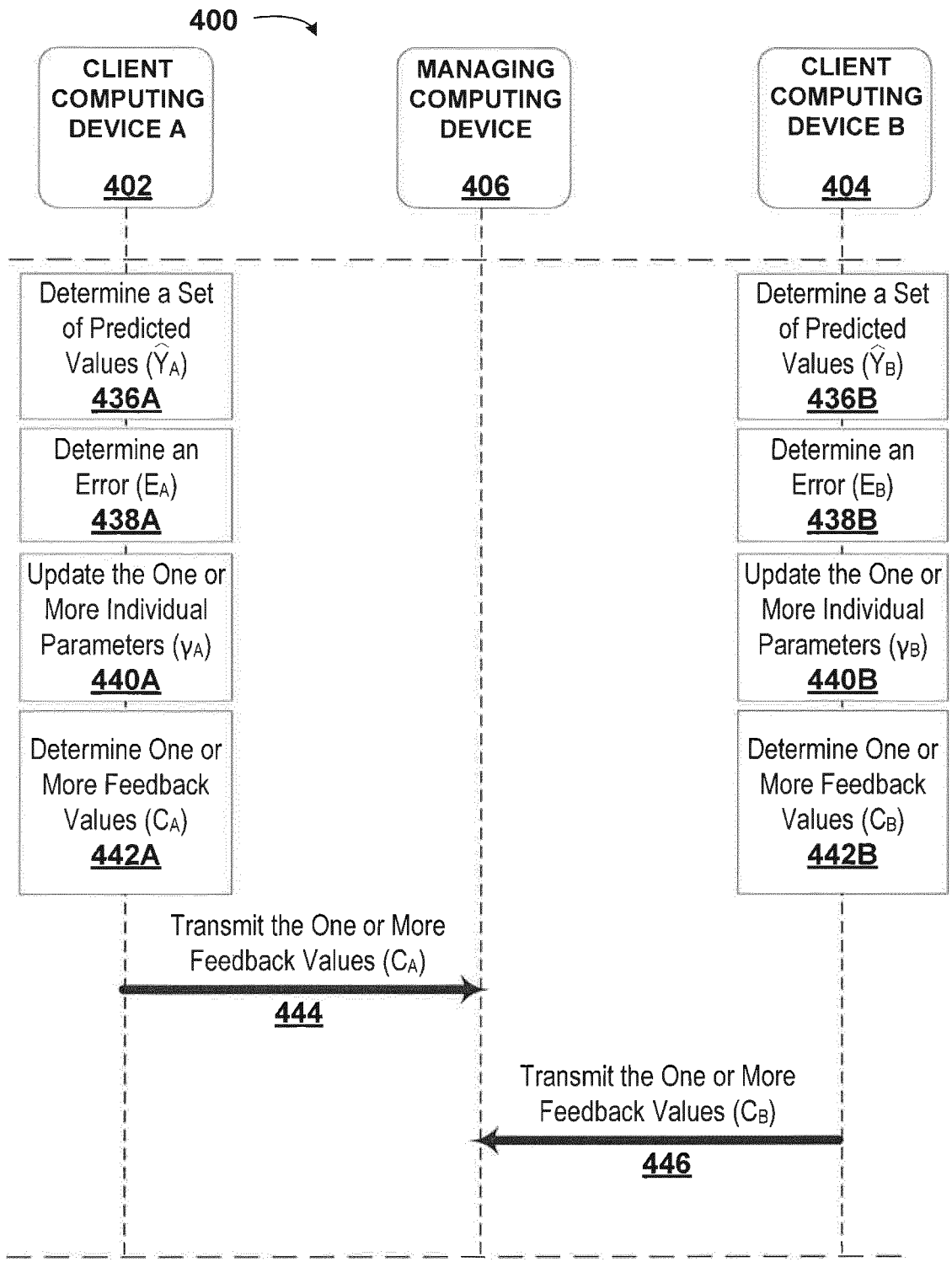
FIG. 4D is a data flow diagram of a portion of a method, according to example embodiments.
Figure 4E:
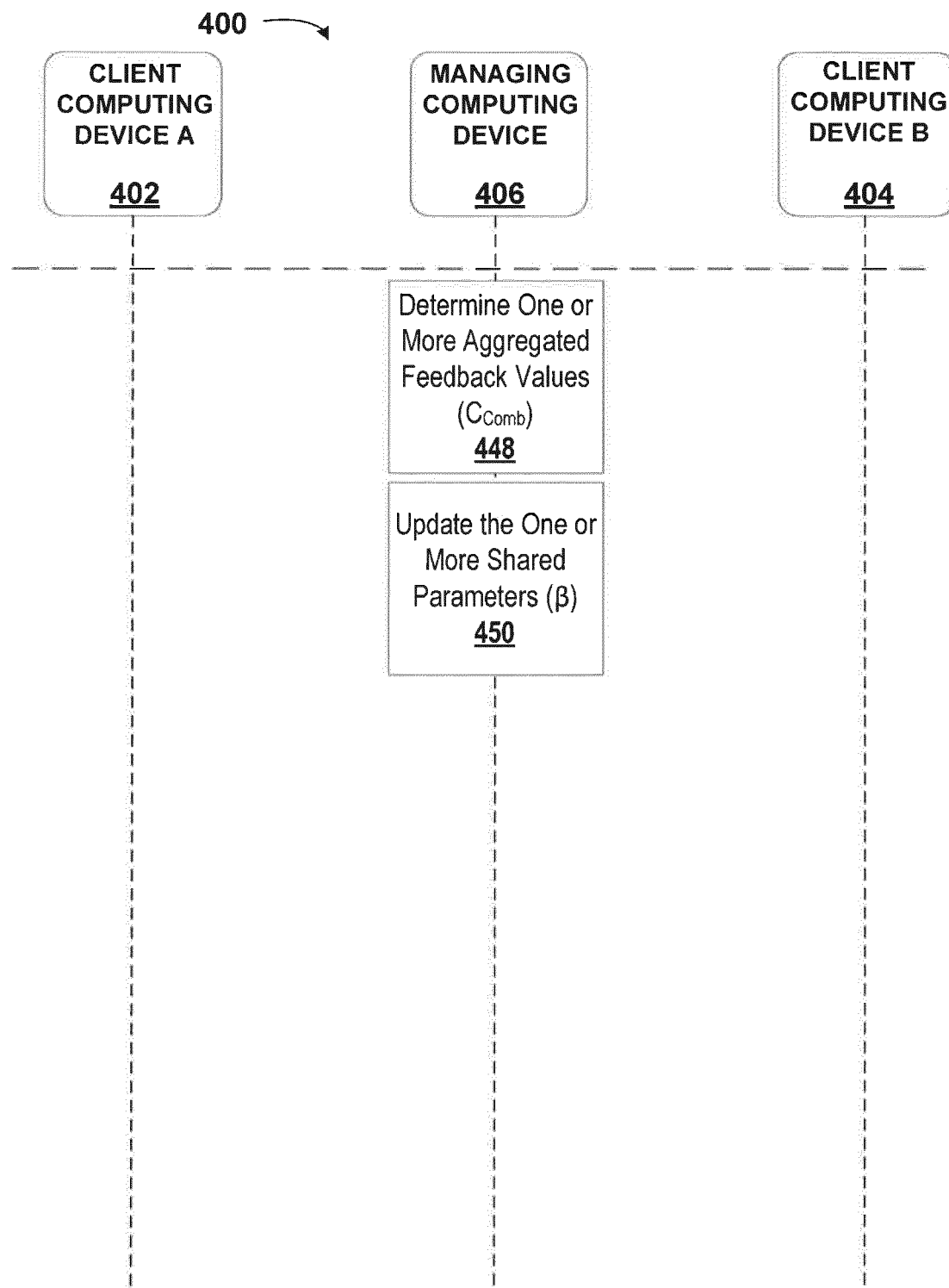
FIG. 4E is a data flow diagram of a portion of a method, according to example embodiments.

FIG. 4B is a data flow diagram illustrating a portion of a method 400. Additional portions of the method 400 are illustrated in FIGS. 4C-4E. The method 400 may be used to develop a shared representation (U) based on a shared function (f) and one or more shared parameters (β). The method 400 may be carried out by client computing device A 402, client computing device B 404, and the managing computing device 406 of the computing network 401 (e.g., as illustrated in FIG. 4A). As indicated with respected to FIG. 4A, in alternate embodiments, there may be any number of client computing devices communicating with the managing computing device. Additional client computing devices may serve to provide additional data with which to refine the shared representation (U).

In some embodiments, the method 400 illustrated in FIGS. 4B-4E may correspond to instructions stored on a non-transitory, computer-readable medium (e.g., similar to the data storage 204 illustrated in FIG. 2). The instructions may be executable by a processor to perform the operations of the method 400. Additionally or alternatively, the method 400 may be used to produce a model. The model may be stored on a memory (e.g., similar to the data storage 204 illustrated in FIG. 2). Such a memory with a model stored thereon may be sold or licensed to a party (e.g., an individual or a corporation) corresponding to client computing device A 402, a party (e.g., an individual or a corporation) corresponding to client computing device B 404, or a third party (e.g., an individual or a corporation) that is unrelated to either of the client computing devices or the managing computing device 406. Similarly, the model itself (e.g., the arrangement of data corresponding to the model) may be distributed to one or more third parties without an associated memory.

According to an example embodiment, the operations of the method 400 will be enumerated with reference to FIGS. 4B-4E. However, additional details for the operations of the example embodiment shown and described in FIGS. 4B-4E are provided below with reference to FIGS. 5A-15B. The dashed horizontal lines in FIGS. 4B-4E illustrate a continuation of the method 400 onto the next figure or from the previous figure.

At operation 412, the method 400 may include client computing device A 402 transmitting dataset A ($X_A$) to the managing computing device 406. Dataset A ($X_A$) may correspond to a set of recorded values ($Y_A$). Further, dataset A ($X_A$) may include objects. In alternate embodiments, client computing device A 402 may also transmit the corresponding set of recorded values ($Y_A$) to the managing computing device 406 (e.g., in addition to dataset A ($X_A$)).

At operation 414, the method 400 may include client computing device B 404 transmitting dataset B ($X_B$) to the managing computing device 406. Dataset B ($X_B$) may correspond to a set of recorded values ($Y_B$). Further, dataset B ($X_B$) may include objects. In alternate embodiments, client computing device B 404 may also transmit the corresponding set of recorded values ($Y_B$) to the managing computing device 406 (e.g., in addition to dataset B ($X_B$)).

At operation 416, the method 400 may include the managing computing device 406 determining a list of identifiers for dataset A ($M_A$) and a list of identifiers for dataset B ($M_B$).

At operation 418, the method 400 may include the managing computing device 406 determining a composite list of identifiers ($M_{Comb}$, e.g., representing the "combined" list of identifiers). The composite list of identifiers may include a combination of the lists of identifiers for dataset A ($M_A$) and dataset B ($M_B$).

At operation 420, the method 400 may include the managing computing device 406 determining a list of unique objects ($X_{Comb}$, e.g., representing the "combined" list of objects from the datasets) from dataset A ($X_A$) and dataset B ($X_B$).

At operation 422, the method 400 may include the managing computing device 406 selecting a subset of identifiers (S) from the composite list of identifiers ($M_{Comb}$).

At operation 424, the method 400 may include the managing computing device 406 determining a subset of the list of unique objects (Z) corresponding to each identifier in the subset of identifiers (S).

FIG. 4C is a data flow diagram illustrating a portion of a method 400. Additional operations of the method 400 are illustrated in FIG. 4C.

At operation 426, the method 400 may include the managing computing device 406 computing a shared representation (U) of the datasets ($X_A/X_B$) based on the subset (Z) of the list of unique objects ($X_{Comb}$) and a shared function (f) having one or more shared parameters (13).

At operation 428, the method 400 may include the managing computing device 406 determining a sublist of objects ($S_A/S_B$) for the respective dataset ($X_A/X_B$) of each client computing device. The sublist of objects ($S_A/S_B$) may be based on an intersection of the subset of identifiers (S) with the list of identifiers ($M_A/M_B$) for the respective dataset ($X_A/X_B$).

At operation 430, the method 400 may include the managing computing device 406 determining a partial representation ($U_A/U_B$) for the respective dataset ($X_A/X_B$) of each client computing device based on the sublist of objects ($S_A/S_B$) for the respective dataset ($X_A/X_B$) and the shared representation (U).

At operation 432, the method 400 may include the managing computing device 406 transmitting the sublist of objects ($S_A$) for dataset A ($X_A$) and the partial representation ($U_A$) for dataset A ($X_A$) to client computing device A 402.

At operation 434, the method 400 may include the managing computing device 406 transmitting the sublist of objects ($S_B$) for dataset B ($X_B$) and the partial representation ($U_B$) for dataset B ($X_B$) to client computing device B 404. It is understood that, in some embodiments, operation 434 may also happen before or substantially simultaneous with operation 432.

In alternate embodiments, instead of operations 428, 430, 432, and 434, the managing computing device 406 may transmit: the shared representation (U), the subset of identifiers (S), and the list of identifiers ($M_A$) for dataset A ($X_A$) to client computing device A 402; and the shared representation (U), the subset of identifiers (S), and the list of identifiers ($M_B$) for dataset B ($X_B$) to client computing device B 404. Then, each respective client computing device may determine, for itself, the corresponding sublist of objects ($S_A/S_B$) for its respective dataset ($X_A/X_B$). The sublist of objects ($S_A$) for dataset A ($X_A$) may be based on an intersection of the subset of identifiers (S) with the list of identifiers ($M_A$) for dataset A ($X_A$). The sublist of objects ($S_B$) for dataset B ($X_B$) may be based on an intersection of the subset of identifiers ($S_B$) with the list of identifiers ($M_B$) for dataset B ($X_B$). Further, each respective client computing device may determine, for itself, the partial representation ($U_A/U_B$) for its respective dataset ($X_A/X_B$). The partial representation ($U_A$) for dataset A ($X_A$) may be based on the sublist of objects ($S_A$) and the shared representation (U). The partial representation ($U_B$) for dataset B ($X_B$) may be based on the sublist of objects ($S_B$) and the shared representation (U).

FIG. 4D is a data flow diagram illustrating a portion of a method 400. Additional operations of the method 400 are illustrated in FIG. 4D.

At operation 436A, the method 400 may include client computing device A 402 determining a set of predicted values ($\hat{Y}_A$) that corresponds to dataset A ($X_A$). The set of predicted values may be based on the partial representation ($U_A$) and an individual function ($g_A$) with one or more individual parameters ($\gamma_A$) corresponding to dataset A ($X_A$).

At operation 436B, the method 400 may include client computing device B 404 determining a set of predicted values ($\hat{Y}_B$) that corresponds to dataset B ($X_B$). The set of predicted values may be based on the partial representation ($U_B$) and an individual function ($g_B$) with one or more individual parameters ($\gamma_B$) corresponding to dataset B ($X_B$).

At operation 438A, the method 400 may include client computing device A 402 determining an error ($E_A$) for dataset A ($X_A$). The error ($E_A$) may be based on an individual loss function ($L_A$) for dataset A ($X_A$), the set of predicted values ($\hat{Y}_A$) that corresponds to dataset A ($X_A$), the sublist of objects ($S_A$), and non-empty entries ($W_A$) in the set of recorded values ($Y_A$) corresponding to dataset A ($X_A$).

At operation 438B, the method 400 may include client computing device B 404 determining an error ($E_B$) for dataset B ($X_B$). The error ($E_B$) may be based on an individual loss function ($L_B$) for dataset B ($X_B$), the set of predicted values ($\hat{Y}_B$) that corresponds to dataset B ($X_B$), the sublist of objects ($S_B$), and non-empty entries ($W_B$) in the set of recorded values ($Y_B$) corresponding to dataset B ($X_B$).

At operation 440A, the method 400 may include client computing device A 402 updating the one or more individual parameters ($\gamma_A$) for dataset A ($X_A$).

At operation 440B, the method 400 may include client computing device B 404 updating the one or more individual parameters ($\gamma_B$) for dataset B ($X_B$).

At operation 442A, the method 400 may include client computing device A 402 determining one or more feedback values ($C_A$). The one or more feedback values ($C_A$) may be used to determine a change in the partial representation ($U_A$) that corresponds to an improvement in the set of predicted values ($\hat{Y}_A$).

At operation 442B, the method 400 may include client computing device B 404 determining one or more feedback values ($C_B$). The one or more feedback values ($C_B$) may be used to determine a change in the partial representation ($U_B$) that corresponds to an improvement in the set of predicted values ($\hat{Y}_B$).

At operation 444, the method 400 may include client computing device A 402 transmitting the one or more feedback values ($C_A$) to the managing computing device 406.

At operation 446, the method 400 may include client computing device B 404 transmitting the one or more feedback values ($C_B$) to the managing computing device 406. In some embodiments, operation 444 may occur after or substantially simultaneous with operation 446.

In some embodiments (e.g., embodiments including more than two datasets and/or more than two client computing devices), only a subset of the client computing devices may transmit one or more feedback values (e.g., $C_A/C_B$) to the managing computing device 406. In such embodiments, the managing computing device 406 may update the one or more shared parameters ($\beta$) based only on the one or more feedback values provided, rather than all possible sets of one or more feedback values from all client computing devices. Alternatively, in embodiments where only a subset of the client computing devices transmit one or more feedback values to the managing computing device 406, the managing computing device 406 may transmit a request to those client computing devices that did not provide one or more feedback values for one or more feedback values from the respective client computing device.

FIG. 4E is a data flow diagram illustrating a portion of a method 400. Additional operations of the method 400 are illustrated in FIG. 4E.

At operation 448, the method 400 may include the managing computing device 406 determining one or more aggregated feedback values ($C_{Comb}$). The one or more aggregated feedback values ($C_{Comb}$) may be based on the sublists of objects ($S_A/S_B$) corresponding to dataset A ($X_A$) and dataset B ($X_B$), respectively, and the one or more feedback values ($C_A/C_B$) from client computing device A 402 and client computing device B 404, respectively.

At operation 450, the method 500 may include the managing computing device 406 updating the one or more shared parameters ($\beta$) based on the one or more aggregated feedback values ($C_{Comb}$). In some embodiments (e.g., embodiments where the one or more aggregated feedback values ($C_{Comb}$) correspond to back-propagated errors), the one or more shared parameters ($\beta$) may be updated according to a gradient descent method.

In some embodiments, the method illustrated in FIGS. 4B-4E may include additional operations. Such additional operations may occur before, after, or concurrently with operations illustrated in FIGS. 4B-4E. Further, the following additional operations may occur in various orders and combinations in various embodiments.

Figure 4F:
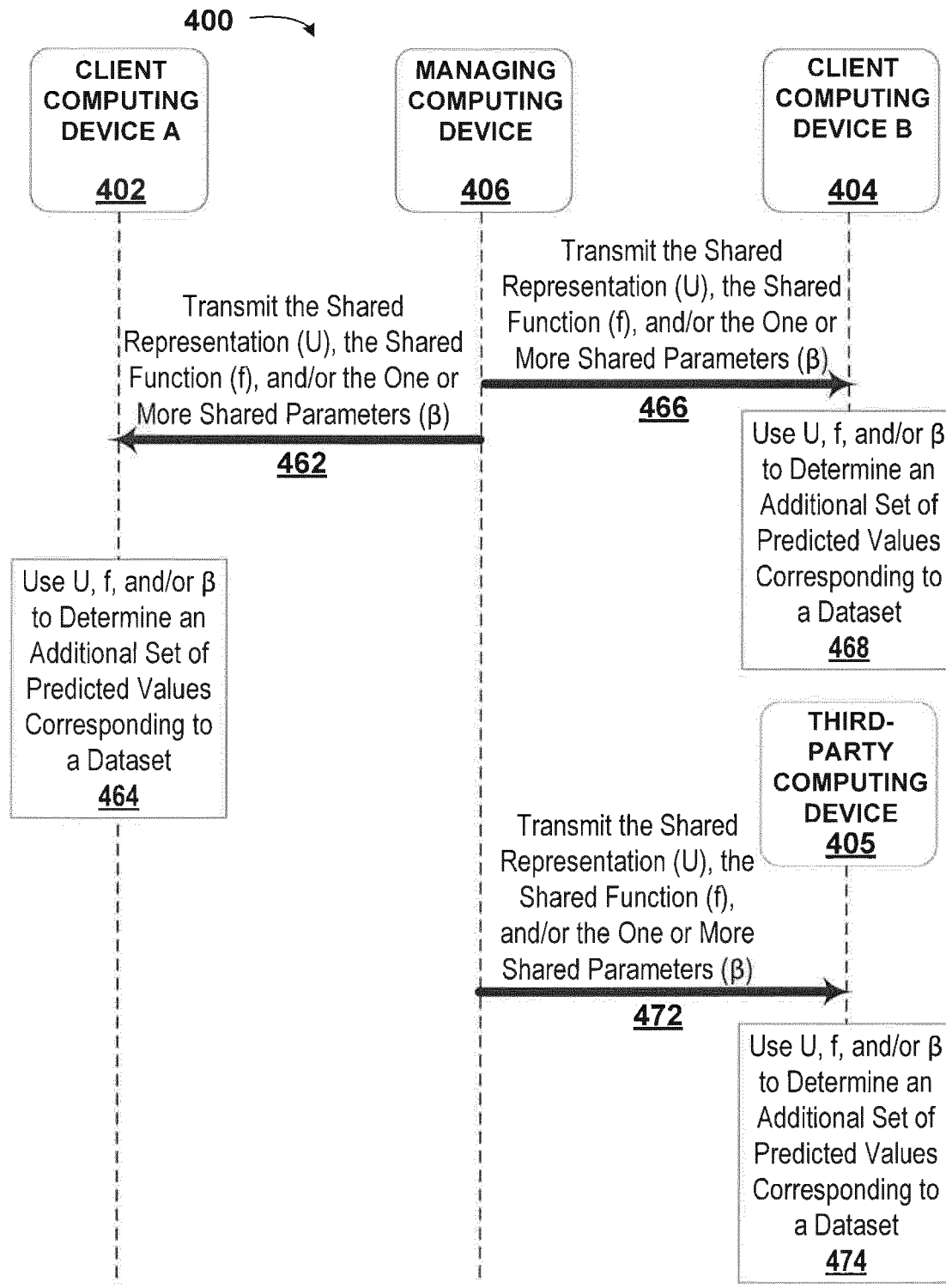
FIG. 4F is a data flow diagram of a portion of a method, according to example embodiments.

For example, as illustrated in FIG. 4F, in some alternate embodiments, at operation 462 and operation 466, the method 400 may optionally include the managing computing device 406 transmitting the shared representation (U), the shared function (f) and/or the one or more shared parameters ($\beta$) to each of the client computing devices. Alternatively, in some embodiments, the method may include the managing computing device 406 transmitting the shared function (f) and/or the one or more shared parameters ($\beta$) to a subset of the client computing devices. Such a subset may be chosen by the managing computing device 406 based on whether the respective client computing device paid a fee (e.g., for a machine-learned model subscription service), entered access credentials (e.g., a username and password), or is a member of a given group (e.g., a group with administrative privileges). Also as illustrated in FIG. 4F, at operation 464, the method 400 may optionally include client computing device A 402 using the shared representation (U), the shared function (f), and/or the one or more shared parameters ($\beta$) to determine an additional set of predicted values corresponding to a dataset (e.g., dataset A ($X_A$) or an alternate dataset). Similarly, at operation 468, the method 400 may optionally include client computing device B 404 using the shared representation (U), the shared function (f), and/or the one or more shared parameters ($\beta$) to determine an additional set of predicted values corresponding to a dataset (e.g., dataset B ($X_B$) or an alternate dataset).

Optionally (e.g., in embodiments that include the third-party computing device 405), as illustrated in FIG. 4F, at operation 472, the method 400 may also include the managing computing device 406 transmitting the shared representation (U), the shared function (f), and/or the one or more shared parameters ($\beta$) to the third-party computing device 405. Similarly, at operation 474 the method 400 may further include the third-party computing device 405 using the shared representation (U), the shared function (f), and/or the one or more shared parameters ($\beta$) to determine an additional set of predicted values corresponding to a dataset. In still other embodiments, the third-party computing device 405 may receive the shared representation (U), the shared function (f), and/or the one or more shared parameters ($\beta$) from one or more of the client computing devices (e.g., client computing device A 402 and/or client computing device B 404), rather than from the managing computing device 406.

In yet other embodiments, the method may include the managing computing device 406 transmitting only a portion of the shared function (f) and/or only a portion of the one or more shared parameters ($\beta$) to the client computing devices 402/404 and/or the third-party computing device 405. The portions received by the client computing devices 402/404 or the third-party computing device 405 may be different. For example, each client computing device may only receive the portion of the one or more shared parameters ($\beta$) that correspond to the portion of the shared representation (U) that was developed according to the dataset ($X_A/X_B$) supplied by the client computing device.

Additionally or alternatively, the method may include the managing computing device 406 computing a final shared representation ($U_{Final}$) of the datasets ($X_A/X_B$). Such a final shared representation ($U_{Final}$) may be based on the list of unique objects ($X_{Comb}$), the shared function (f), and the one or more shared parameters (β). Further, the method may include the managing computing device 406 transmitting the final shared representation ($U_{Final}$) of the datasets ($X_A/X_B$) to client computing device A 402 and/or client computing device B 404. The shared representation ($U_{Final}$) may be usable by each client computing device (or a subset of the client computing devices) to determine a final set of predicted values ($\hat{Y}_{A_{Final}}/\hat{Y}_{B_{Final}}$) corresponding to the respective dataset ($X_A/X_B$) of the client computing device. Determining the final set of predicted values ($\hat{Y}_{A_{Final}}/\hat{Y}_{B_{Final}}$) may include the respective client computing device determining a final partial representation ($U_{Final\_A}/U_{Final\_B}$) for the respective dataset ($X_A/X_B$) based on the list of identifiers ($M_A/M_B$) for the respective dataset ($X_A/X_B$). Determining the final set of predicted values ($\hat{Y}_{A_{Final}}/\hat{Y}_{B_{Final}}$) may also include the respective client computing device determining the final set of predicted values ($\hat{Y}_{A_{Final}}/\hat{Y}_{B_{Final}}$) corresponding to the respective dataset ($X_A/X_B$) based on the final partial representation ($U_{Final\_A}/U_{Final\_B}$), the individual function ($g_A/g_B$), and the one or more individual parameters ($\gamma_A/\gamma_B$) corresponding to the respective dataset ($X_A/X_B$). In some embodiments, the final set of predicted values ($\hat{Y}_{A_{Final}}/\hat{Y}_{B_{Final}}$) may be displayed by at least one of the client computing devices. In some embodiments, the final set of predicted values ($\hat{Y}_{A_{Final}}/\hat{Y}_{B_{Final}}$) may be used by at least one of the client computing devices to provide one or more predictions about objects in the dataset ($X_A/X_B$) corresponding to the respective client computing device.

In some embodiments, multiple operations may be repeated one or more times to further refine the machine-learned model. For example, operations 422, 424, 426, 428, 430, 432, 434, 436A, 436B, 438A, 438B, 440A, 440B, 442A, 442B, 444, 446, 448, and 450 may be repeated one or more times to refine the machine-learned model. When these operations are repeated, they may be repeated such that each determining/selecting operation includes determining/selecting additional subsets of data (e.g., possibly different from the selections in the previous iteration).

In some embodiments, the method may also include the managing computing device 406 removing ("purging") the list of unique objects ($X_{Comb}$), the shared representation (U), the lists of identifiers ($M_A/M_B$) for each dataset ($X_A/X_B$), and the composite list of identifiers ($M_{Comb}$) from a memory (e.g., a data storage 204 as illustrated in FIG. 2) of the managing computing device 406. In some embodiments, removing the above data from the managing computing device 406 may include removing the data from a corresponding cloud storage device and/or from multiple servers used to store the data of the managing computing device. The removal of such data may prevent the managing computing device from having access to the data for an unspecified amount of time after the machine-learned model has been developed.

FIG. 5A is an illustration of dataset A ($X_A$) and a corresponding set of recorded values ($Y_A$) (e.g., as described with respect to FIGS. 4B-4E). Dataset A ($X_A$) and the corresponding set of recorded values ($Y_A$) may correspond to client computing device A 402. In some embodiments, dataset A ($X_A$) may be stored in a primary memory storage (e.g., an internal hard drive) of client computing device A 402 and the corresponding set of recorded values ($Y_A$) may be stored in a secondary memory storage (e.g., an external hard drive) of client computing device A 402.

As illustrated, dataset A ($X_A$) includes four objects in a first dimension (e.g., "Timmy," "Johnny," "Sally," and "Sue"). These objects may correspond to user profiles of an online book-rating and movie-rating platform (e.g., including a database) run by client computing device A 402 or associated with client computing device A 402, for example. Such user profiles may be identified by their profile name, their user identification (ID) number, a hash code, a social security number, or an internet protocol (IP) address associated with a user profile. Other methods of identifying user profiles are also possible.

In a second dimension of dataset A ($X_A$), there may be seven features corresponding to each of the four objects (e.g., "Book Title 1," "Book Title 2," "Book Title 3," "Book Title 4," "Book Title 5," "Book Title 6," and "Book Title 7"). Such features may alternatively be identified by their 10-digit or 13-digit international standard book number (ISBN), for example, or by a corresponding unified resource locator (URL) from the book-rating and movie-rating platform.

The entries corresponding to each pair of (object, feature) may correspond to a rating value (e.g., ranging from 0-100). For example, user "Sally" may have rated "Book Title 4" with a rating of "17." These entries may be scaled such that they all have the same range (e.g., some of the ratings may have originally be issued between 0-10 and then scaled to ensure they ranged from 0-100 and were normalized to the other rating values).

In alternate embodiments, other types of objects and/or features may be used within dataset A ($X_A$). Further, in other embodiments, other numbers of objects and/or features may be used. In addition, in some embodiments, other types of data entries may be used. Additionally or alternatively, in some embodiments, there may be greater than two dimensions (d) for dataset A ($X_A$).

As illustrated, the corresponding set of recorded values ($Y_A$) includes the same four objects in a first dimension (e.g., "Timmy," "Johnny," "Sally," and "Sue") as the four objects in dataset A ($X_A$). As with above, these objects may correspond to user profiles of an online book-rating and movie-rating platform run by client computing device A 402 or associated with client computing device A 402, for example. Again, such user profiles may be identified by their profile name, their user ID number, a hash code, a social security number, or an IP address associated with a user profile. Other methods of identifying user profiles are also possible.

In a second dimension of the corresponding set of recorded values ($Y_A$), there may be five features corresponding to each of the four objects (e.g., "Movie Title 1," "Movie Title 2," "Movie Title 3," "Movie Title 4," and "Movie Title 5"). Such features may alternatively be identified by their barcode or a corresponding URL from the book-rating and movie-rating platform.

The entries corresponding to each pair of (object, feature) in the corresponding set of recorded values ($Y_A$) may correspond to a rating value (e.g., ranging from 0-100). For example, object "Johnny" may have rated feature "Movie Title 2" with a value of "18." These entries may be scaled such that they all have the same range (e.g., some of the ratings may have originally been issued between 0-10 and then scaled to ensure they ranged from 0-100 and were normalized to the other rating values).

In alternate embodiments, other types of objects and/or features may be used within the corresponding set of recorded values ($Y_A$). Further, in other embodiments, other numbers of objects and/or features may be used. In addition, in some embodiments, other types of data entries may be used. Additionally or alternatively, in some embodiments, there may be greater than two dimensions (d) for the corresponding set of recorded values ($Y_A$). The number of dimensions (d) in the corresponding set of recorded values ($Y_A$) may be the same as the number of dimensions (d) in dataset A ($X_A$). Alternate embodiments of datasets and corresponding sets of recorded values are illustrated and described further with reference to FIGS. 16A-16C.

FIG. 5B is an illustration of dataset B ($X_B$) and a corresponding set of recorded values ($Y_B$) (e.g., as described with respect to FIGS. 4B-4E). Dataset B ($X_B$) and the corresponding set of recorded values ($Y_B$) may correspond to client computing device B 404. Dataset B ($X_B$) and the corresponding set of recorded values ($Y_B$) may correspond to a separate book-rating and movie-rating platform (e.g., including a database) from the book-rating and movie-rating platform of dataset A ($X_A$) and its corresponding set of recorded values ($Y_A$). As illustrated in FIG. 5B, the objects in dataset B ($X_B$) might not be the same as the objects in dataset A ($X_A$). In some embodiments, as illustrated, there may be some overlap in objects between dataset B ($X_B$) and dataset A ($X_A$). In still other embodiments, the objects in the datasets ($X_A/X_B$) may be entirely the same. In even further embodiments, the objects in the datasets ($X_A/X_B$) may be entirely disjoint. Also as illustrated, the number of objects in dataset B ($X_B$) might not be the same as the number of objects in dataset A ($X_A$).

As illustrated, the number of features in additional dimensions of dataset B ($X_B$) and the corresponding set of recorded values ($Y_B$) may be the same as the number of features in additional dimensions of dataset A ($X_A$) and its corresponding set of recorded values ($Y_A$). As illustrated, there are seven features in the additional dimension of dataset B ($X_B$) (e.g., "Book Title 1," "Book Title 2," "Book Title 3," "Book Title 4," "Book Title 5," "Book Title 6," and "Book Title 7"). As shown, these features are the same as the features of dataset A ($X_A$) illustrated in FIG. 5A.

Still further, the number of features the corresponding set of recorded values ($Y_B$) may be different than the number of features in the corresponding set of recorded values ($Y_A$). As illustrated, there are nine features in the additional dimension of the corresponding set of recorded values ($Y_B$) (e.g., "Movie Title 1," "Movie Title 3," "Movie Title 4," "Movie Title 5," "Movie Title 6," "Movie Title 7," "Movie Title 8," "Movie Title 9," and "Movie Title 10"). As shown, some of these features are the same as the features of the corresponding set of recorded values ($Y_A$) illustrated in FIG. 5A. In alternate embodiments, all or none of the features will overlap with features of corresponding sets of recorded values.

Additionally, in some embodiments, the numbers of dimensions (d) in dataset B ($X_B$) and corresponding set of recorded values ($Y_B$) of FIG. 5B, might not be same as the number of dimensions (d) in dataset A ($X_A$) and corresponding set of recorded values ($Y_A$) of FIG. 5A. In some embodiments, each of the plurality of datasets (e.g., $X_A/X_B$) may include an equal number of dimensions (d). In various embodiments, the number of dimensions (d) may be two, three, four, five, six, seven, eight, nine, ten, sixteen, thirty-two, sixty-four, one-hundred and twenty-eight, two-hundred and fifty-six, five-hundred and twelve, or one-thousand and twenty-four. Other numbers of dimensions (d) are also possible. In some embodiments, each of the plurality of datasets may be represented by a tensor. Further, in some embodiments, at least one of the plurality of datasets may be represented by a sparse tensor. In various embodiments, a tensor may be a "sparse" tensor if the tensor's sparsity is greater than 50%, greater than 60%, greater than 70%, greater than 75%, greater than 80%, greater than 90%, greater than 95%, greater than 98%, greater than 99%, greater than 99.9%, greater than 99.99%, greater than 99.999%, or greater than 99.9999%. In the embodiment illustrated in FIGS. 5A/5B, both of the datasets ($X_A/X_B$) are represented by tensors (e.g., two-dimensional tensors, i.e., "matrices").

Additionally or alternatively, in some embodiments, at least one of the corresponding sets of recorded values may be represented by a tensor. In addition, in some embodiments, at least one of the corresponding sets of recorded values may be represented by a sparse tensor. In the embodiment illustrated in FIGS. 5A/5B, both of the corresponding sets of recorded values ($Y_A/Y_B$) are represented by tensors (e.g., two-dimensional tensors, i.e., "matrices").

In some embodiments, there may be more than two pairs of datasets and corresponding sets of recorded values. Additional pairs of datasets and sets of recorded values may be transmitted by and/or stored within client computing device A 402 or client computing device B 404. Additionally or alternatively, additional pairs of datasets and sets of recorded values may be transmitted by and/or stored within additional client computing devices (e.g., client computing devices not illustrated in FIG. 4A). Additionally or alternatively, in some embodiments, some or all of the datasets (e.g., $X_A/X_B$) may be stored and/or transmitted on separate client computing devices from their corresponding sets of recorded values (e.g., $Y_A/Y_B$). If two separate client computing devices store and/or transmit a dataset (e.g., $X_A$) and the corresponding set of recorded values ($Y_A$), the separate client computing devices may be controlled and/or owned by a single client (e.g., a corporation). Alternatively, the separate client computing devices may be controlled and/or owned by separate clients. Still further, in embodiments where the separate client computing devices are controlled and/or owned by separate clients, the separate clients may not communicate with one another (e.g., for privacy reasons), leaving the managing computing device 406 to ultimately associate dataset A ($X_A$) with the corresponding set of recorded values ($Y_A$) upon receiving both individually. This may be done using metadata (e.g., tags) attached to dataset A ($X_A$) and the corresponding set of recorded values ($Y_A$) by each of the separate client computing devices such that the managing computing device 406 can identify that dataset A ($X_A$) corresponds to the set of recorded values ($Y_A$).

In various embodiments, the data represented by the datasets and the corresponding sets of recorded values may vary. For example, the method 400 may be used in a variety of applications, each application potentially corresponding to a different set of data stored within the datasets and different corresponding sets of recorded values. This is described and illustrated further with reference to FIGS. 16A-16C.

FIGS. 6A and 6B illustrate operation 416 of the method 400 illustrated in FIGS. 4B-4E. As described with reference to FIG. 4B, at operation 416, the method 400 may include the managing computing device determining a list of identifiers ($M_A$) for dataset A ($X_A$) and a list of identifiers ($M_B$) for dataset B ($X_B$). As illustrated in FIG. 6A, the objects of the dataset ($X_A$) are being converted to a list of identifiers ($M_A$) for dataset ($X_A$). The list of identifiers ($M_A$) may correspond to unique IDs (e.g., strings, hash codes, or integers) assigned by the managing computing device 406 to each object in the dataset ($X_A$). The unique IDs in the list of identifiers ($M_A$) may be generated such that the objects in dataset A ($X_A$) may be meaningfully compared to the objects in dataset B ($X_B$). Hence, as illustrated in FIG. 6B, the objects of dataset B ($X_B$) are being converted to a list of identifiers ($M_B$) for dataset B ($X_B$). The list of identifiers ($M_B$) may also correspond to unique IDs (e.g., strings, hash codes, or integers) assigned by the managing computing device 406 to each object in dataset B ($X_B$). As illustrated, in some embodiments, those objects that are the same in both dataset A ($X_A$) and dataset B ($X_B$) may be assigned the same identifier (e.g., "Timmy" is assigned "User00" and "Johnny" is assigned "User01" in both lists of identifiers $M_A/M_B$).

Determining, by the managing computing device 406, a respective list of identifiers for each dataset ($X_A/X_B$) may include various operations in various embodiments. In some embodiments, the lists of identifiers ($M_A/M_B$) may be provided to the managing computing device 406 by the respective client computing devices (computing device A 402/ computing device B 404). In other embodiments, the managing computing device 406 may define the unique IDs based on an algorithm of the managing computing device 406. In still other embodiments, determining, by the managing computing device, the lists of identifiers ($M_A/M_B$) may include receiving commercially available identifiers for the objects (e.g., ISBNs for books or social security numbers for patients). Such commercially available identifiers for the objects may be provided to the managing computing device 406 by a third party (e.g., a domain name registrar may provide corresponding IP addresses for objects corresponding to domain names). Regardless of the technique used to define the unique IDs in the lists of identifiers ($M_A/M_B$), the unique IDs may be defined such that each unique ID is defined according to a common syntax, thereby enabling a creation of a composite list of identifiers ($M_{Comb}$).

Figure 7:
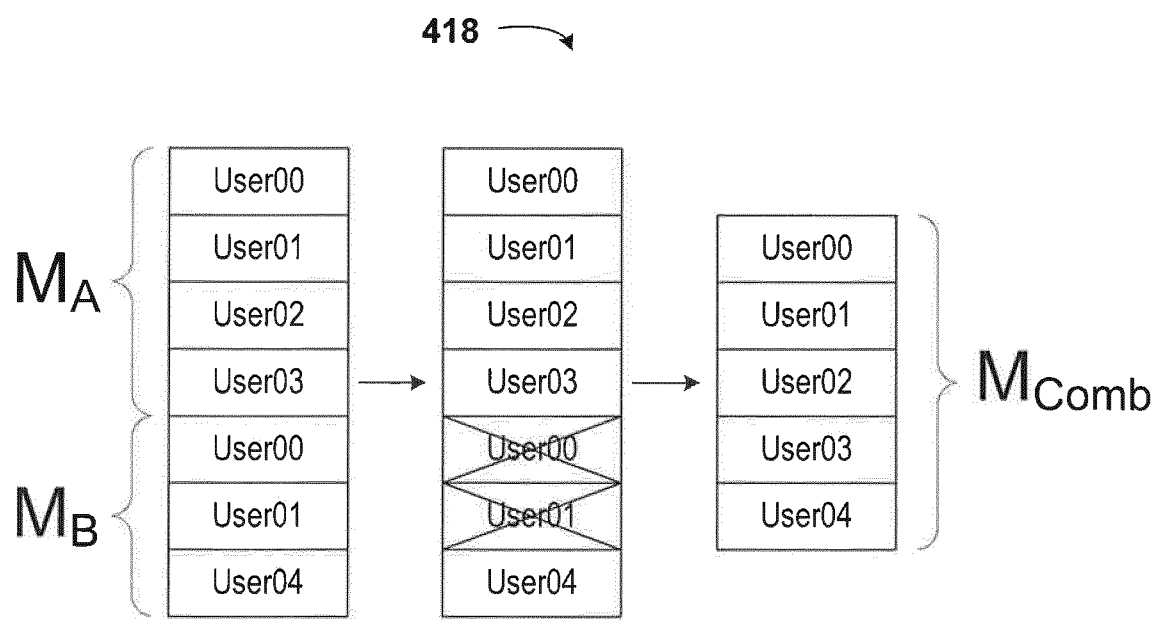
FIG. 7 illustrates a composite list of identifiers, according to example embodiments.

FIG. 7 illustrates operation 418 of the method 400 illustrated in FIGS. 4B-4E. As described with reference to FIG. 4B, at operation 418, the method 400 may include the managing computing device 406 determining a composite list of identifiers ($M_{Comb}$). As illustrated in FIG. 7, the list of identifiers ($M_A$) for dataset A ($X_A$) and the list of identifiers ($M_B$) for dataset B ($M_B$) may be combined (e.g., concatenated) to form a list of all identifiers. This list of all identifiers may have repeated (i.e., "redundant") identifiers (e.g., "User00" and "User01" in the example embodiment of FIG. 7) removed. Upon removing the redundant identifiers, a composite list of identifiers ($M_{Comb}$) may remain. The composite list of identifiers ($M_{Comb}$) may include all non-repeated identifiers corresponding to all datasets ($X_A/X_B$) received by the managing computing device 406.

Figure 8:
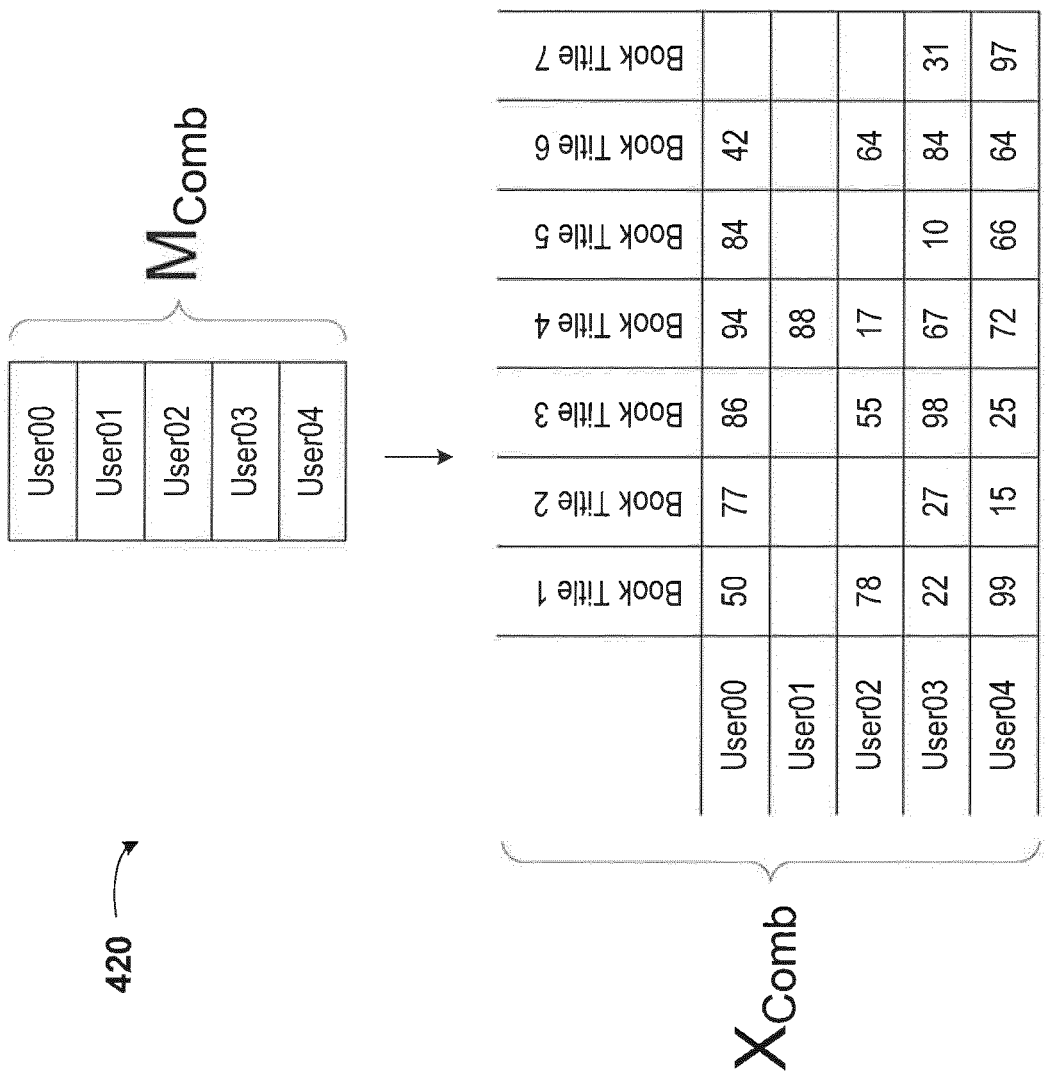
FIG. 8 illustrates a list of unique objects, according to example embodiments.

FIG. 8 illustrates operation 420 of the method 400 illustrated in FIGS. 4B-4E. As described with reference to FIG. 4B, at operation 420, the method 400 may include the managing computing device 406 determining a list of unique objects ($X_{Comb}$) from dataset A ($X_A$) and dataset B ($X_B$). As illustrated in FIG. 8, determining a list of unique objects ($X_{Comb}$) may include combining data from all datasets into a single list (e.g., a single tensor). The data may be combined based on the composite list of identifiers ($M_{Comb}$). For example, "User00" may have been an object in both dataset A ($X_A$) and dataset B ($X_B$). Hence, as illustrated in FIG. 8, the data from dataset A ($X_A$) and dataset B ($X_B$) is combined into data for a single object ("User00") in the list of unique objects ($X_{Comb}$). In some embodiments, if different scales were used (e.g., if dataset A ($X_A$) has ratings ranging from 0 to 10 and dataset B ($X_B$) has ratings scaling from 0 to 100), the values of the objects in each dataset may be normalized before inputting them into the list of unique objects ($X_{Comb}$).

In some embodiments, two or more datasets may include the same object (e.g., "Timmy" in FIG. 8 was in dataset A ($X_A$) and dataset B ($X_B$)), but have conflicting data for the same feature of the same object. For example, if "Timmy" had provided "Book Title 5" with a rating of "84" in dataset A ($X_A$), but with a rating of "60" in dataset B ($X_B$), this would give rise to a conflict. In some embodiments, such a conflict may be resolved by assigning identifiers in such a way that only those objects having the exact same data for the same features (e.g., the same data for all of the features of the object or the same data for those features of the object where a given object has data at all) will be assigned a common identifier. Using the example in this paragraph, the "Timmy" object in dataset A ($X_A$) and the "Timmy" object in dataset B ($X_B$) may could be assigned different identifiers if they do not share the same data for every feature (e.g., the "Timmy" object from dataset A ($X_A$) may be assigned identifier "User00" while the "Timmy" object from dataset B ($X_B$) may be assigned the identifier "User05"). Using such a technique, adverse effects on machine-learned models, as described herein, due to conflicts may be prevented.

In some embodiments, operation 420 may be performed before operation 418. For example, the objects from dataset A ($X_A$) and the objects from dataset B ($X_B$), and any other dataset in embodiments having greater than two datasets, may be combined prior to creating a composite list of identifiers ($M_{Com}$b). Once combined, repeated (i.e., "duplicate") objects in the combined set of objects may be removed, thereby forming the list of unique objects ($X_{Comb}$). The repeated objects may be removed based on an intersection of the lists of identifiers ($M_A/M_B$) for each of the plurality of datasets ($X_A/X_B$). Then, based on the list of unique objects, the composite list of identifiers ($M_{Comb}$) may be generated.

Figure 9:
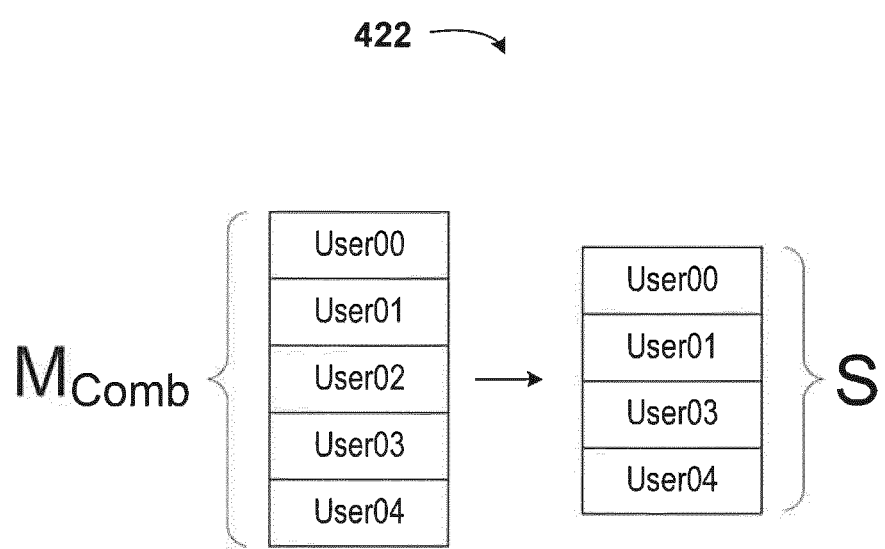
FIG. 9 illustrates a subset of identifiers, according to example embodiments.

FIG. 9 illustrates operation 422 of the method 400 illustrated in FIGS. 4B-4E. As described with reference to FIG. 4B, at operation 422, the method 400 may include the managing computing device 406 selecting a subset of identifiers (S) from the composite list of identifiers ($M_{Comb}$). The subset of identifiers (S) may be selected using various methods. For example, the subset of identifiers (S) may be selected randomly (e.g., using a random number generator, such as a hardware random number generator) or pseudo-randomly (e.g., using a pseudo-random number generator with a seed value). In some embodiments, the subset of identifiers (S) may be selected based on a Mersenne Twister pseudo-random number generator. Additionally or alternatively, each identifier in the subset of identifiers (S) may be selected according to an algorithm known only to the managing computing device 406. In other embodiments, each identifier in the subset of identifiers (S) may be selected according to a publicly available algorithm (e.g., an algorithm that is published by the managing computing device 406 and transmitted to one or more of the plurality of client computing devices 402/404).

Figure 10:
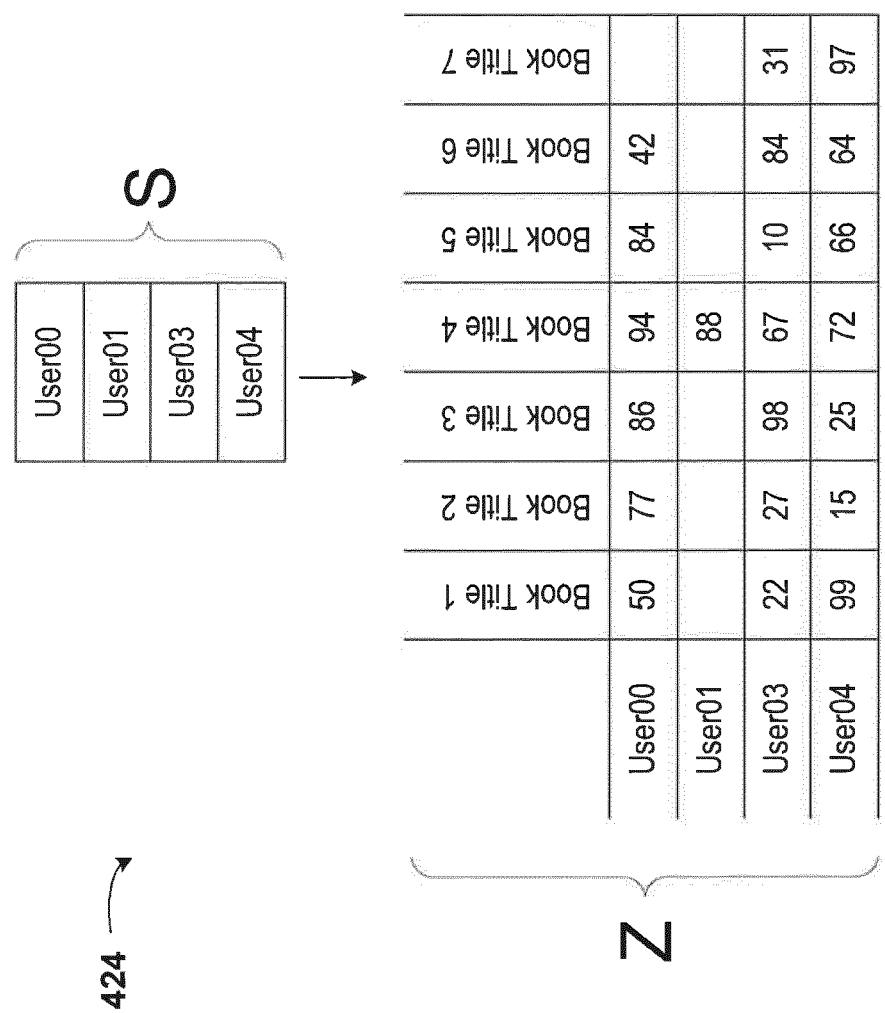
FIG. 10 illustrates a subset of the list of unique objects, according to example embodiments.

FIG. 10 illustrates operation 424 of the method 400 illustrated in FIGS. 4B-4E. As described with reference to FIG. 4B, at operation 424, the method 400 may include the managing computing device 406 determining a subset (Z) of the list of unique objects ($X_{Comb}$) corresponding to each identifier in the subset of identifiers (S). Determining the subset (Z) may include the managing computing device 406 retrieving the list of unique objects ($X_{Comb}$), and then creating a new list of objects based on the list of unique objects ($X_{Comb}$). The managing computing device 406 may then remove from the new list of objects the objects whose corresponding identifiers are not contained within the subset of identifiers (S), thereby creating the subset (Z) of the list of unique objects ($X_{Comb}$). Alternatively, determining the subset (Z) may include the managing computing device 406 retrieving the subset of identifiers (S). Then, based on the subset of identifiers (S), the managing computing device 406 may assemble a new list by adding an object from the list of unique objects ($X_{Comb}$) that corresponds to an identifier in the subset of identifiers (S) for each identifier in the subset of identifiers (S).

Figure 11:
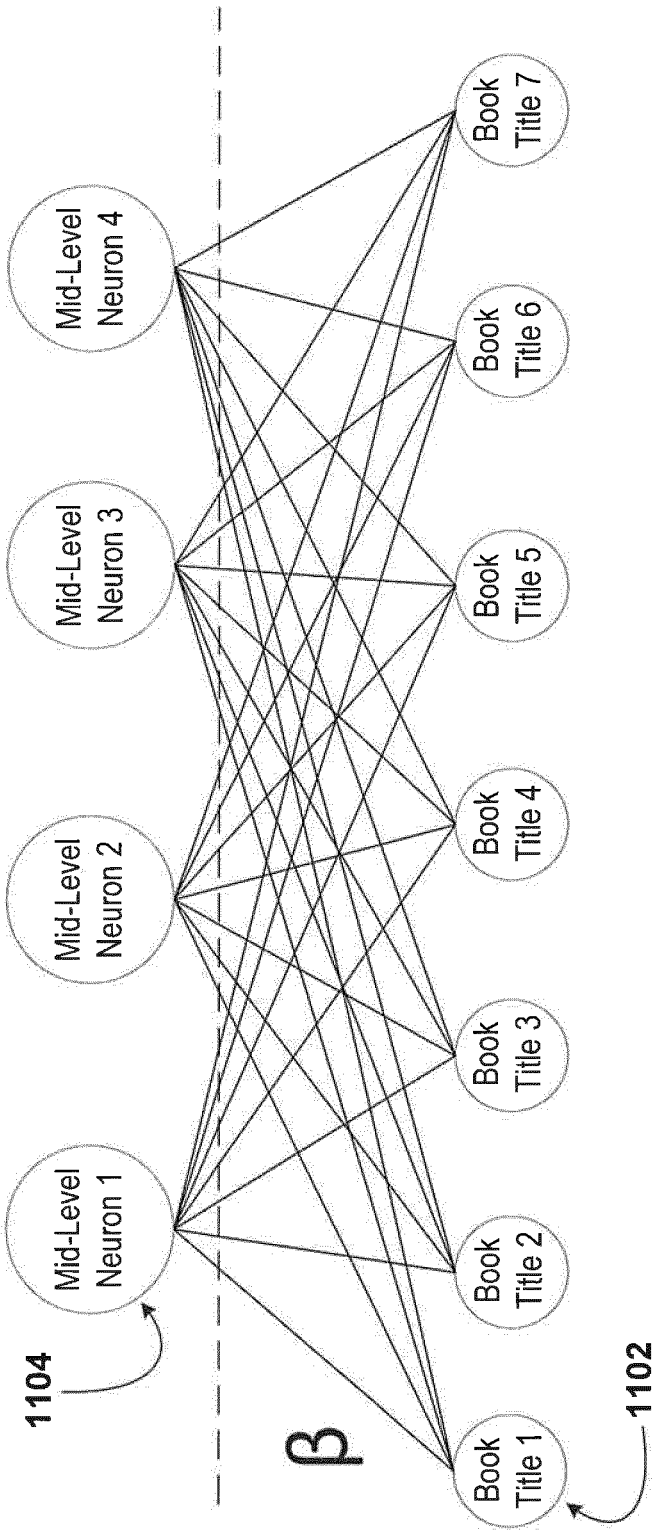
FIG. 11 illustrates a shared representation, according to example embodiments.

FIG. 11 illustrates operation 426 of the method 400 illustrated in FIGS. 4B-4E. As described with reference to FIG. 4C, at operation 426, the method 400 may include the managing computing device 406 computing a shared representation (U) of the datasets ($X_A/X_B$) based on the subset (Z) of the list of unique objects ($X_{Comb}$) and a shared function (f) having one or more shared parameters ($\beta$). In some embodiments (e.g., embodiments where the machine learning model is an artificial neural network), the one or more shared parameters ($\beta$) may correspond to a shared parameter tensor (e.g., shared parameter matrix), such as a weight tensor ($\overline{\beta}$).

FIGS. 11, 13A, 13B, 14A, and 14B (and consequently operations 426, 430, 436A, and 436B of the method 400) are illustrated using, as an example, an artificial neural network model of machine learning (e.g., the shared function (f) may include an artificial neural network having rectified linear unit (ReLU) non-linearity and dropout). It is understood that this model is provided by way of example only, and is not meant to preclude other machine learning models (or even non-machine learning models, e.g., based on statistical approaches) from the scope of the disclosure. Other machine learning models, including supervised learning models, unsupervised learning models, and semi-supervised learning models (e.g., discriminant analysis), may be used in conjunction with the method 400. For example, decision tree learning, association rule learning, deep learning, inductive logic programming, support vector machines, relevance vector machines, clustering, Bayesian networks, reinforcement learning, representation learning, similarity and metric learning, sparse dictionary learning, genetic algorithms, rule-based machine learning, learning classifier systems, deep belief networks, recurrent neural networks, or various combinations of the aforementioned techniques are all implicitly contemplated herein. An alternate type of machine learning for use with the method 400 that is based on matrix factorization is explicitly shown and described with reference to FIGS. 17A and 17B.

As illustrated in FIG. 11, in the example case of an artificial neural network, computing the shared representation (U) of the datasets ($X_A/X_B$) may include correlating each of the features of the objects in the list of unique objects ($X_{Comb}$) to a first-level neuron 1102. After correlating each of the features to a respective first-level neuron 1102, the first-level neurons 1102 may be connected to mid-level neurons 1104 (i.e., intermediate neurons). Only one first-level neuron 1102 and one mid-level neuron 1104 are labeled in FIG. 11 to prevent clutter of the figure. The dashed lines in FIG. 11 are meant to illustrate the possibility that additional neuron layers (e.g., hidden neuron layers) may be present between the first-level neuron 1102 layer and the mid-level neuron 1104 layer.

Connecting the first-level neurons 1102 to the mid-level neurons 1104 may include using the first-level neurons 1102 as inputs to the mid-level neurons 1104. Using the first-level neurons 1102 as inputs to the mid-level neurons 1104 may include multiplying a value of each first-level neuron 1102 by one or more shared parameters ($\beta$) (i.e., one or more "weights"). These one or more shared parameters (13) may be stored as a tensor (e.g., a "weight matrix" in two-dimensional examples). For example, in FIG. 11, Mid-Level Neuron 1 may have a value corresponding to the value of the "Book Title 1" first-level neuron multiplied by a first entry (e.g., "weight") in a weight tensor (e.g., a matrix representing the one or more shared parameters (13)), plus the value of the "Book Title 2" first-level neuron multiplied by a second entry in the weight tensor, plus the value of the "Book Title 3" first-level neuron multiplied by a third entry in the weight tensor, etc. This process may be repeated for each object in the subset (Z) of the list of unique objects ($X_{Comb}$) to arrive at the complete shared representation (U). Represented mathematically, this definition of the complete shared representation (U) may correspond to:

$$U := f(Z; \beta) \rightarrow \overline{FLN} \times \overline{\beta} = \overline{MLN}$$

where $\overline{FLN}$ is a tensor (e.g., matrix) representing the input values for each of the first-level neurons 1102 for each object in the subset (Z) of the list of unique objects ($X_{Comb}$), $\overline{\beta}$ is a weight tensor representing the one or more shared parameters ($\beta$) that define the shared function (f) (e.g., that define how values of the mid-level neurons 1104 depend upon values of the first-level neurons 1102), and $\overline{MLN}$ is a tensor (e.g., matrix) representing the output values for each of the mid-level neurons 1104. As shown above, the shared representation (U) may be defined by the shared function (f) and the objects in the subset (Z) (e.g., U:=f(Z;$\beta$). As illustrated, the shared function (f) may correspond to one or more first layers of an artificial neural network model.

In the example of FIG. 11, $\overline{FLN}$ may be a 4×7 matrix (7 values for each of 4 objects in the subset (Z)), $\overline{\beta}$ may be a 7×4 matrix (showing how the 4 mid-level neurons 1104 each depend on the 7 first-level neurons 1102), and $\overline{MLN}$ may be a 4×4 matrix (4 values for each of 4 objects in the subset (Z)). $\overline{FLN}$ may be a sparse matrix, as not every object ("user") has provided a value ("rating") for each feature ("book title") in the datasets ($X_A/X_B$) received by the managing computing device 406. In other words, because the datasets ($X_A/X_B$) provided by the client computing devices 402/404 may not be complete, $\overline{FLN}$ may also be incomplete (e.g., have entries with no values). Consequently, based on the matrix multiplication above, for example, $\overline{MLN}$ may also be a sparse matrix.

In some embodiments, prior to computing the shared representation (U), the shared function (f) and the one or more shared parameters ($\beta$) (e.g., stored within a "weight" tensor in artificial neural network embodiments) may be initialized by the managing computing device 406. For example, the shared function (f) and the one or more shared parameters ($\beta$) may be initialized based on a related shared function used to model a similar relationship (e.g., if the shared function (f) is being used to model a relationship between risk factors of a given insured individual and a given premium for providing life insurance to that individual, the shared function (f) and the one or more shared parameters ($\beta$) may be set based on a previous model developed to model a relationship between risk factors of a given insured individual and a given premium for providing health insurance to that individual). Initializing the shared function (f) and the one or more shared parameters ($\beta$) based on a related shared function may include setting the shared function (f) and the one or more shared parameters ($\beta$) equal to the related shared function and the one or more shared parameters for the related shared function. Alternatively, initializing the shared function (f) and the one or more shared parameters ($\beta$) based on a related shared function may include scaling and/or normalizing the related shared function and the one or more shared parameters for the related shared function, and then using the scaled and/or normalized values as initial values for the shared function (f) and the one or more shared parameters (β).

In alternate embodiments, the managing computing device 406 initializing the shared function (f) or the one or more shared parameters (β) may include the managing computing device 406 receiving initial values for the one or more shared parameters (β) from one of the client computing devices (e.g., computing device A 402 or computing device B 404). The managing computing device 406 may initialize the shared function (f) and the one or more shared parameters (β) based on the initial values received. The initial values for the one or more shared parameters (f) may be determined by the respective client computing device (e.g., client computing device A 402 or client computing device B 404) based upon one or more public models (e.g., publicly available machine-learned models).

In still other embodiments, the managing computing device 406 may initialize the shared function (f) and the one or more shared parameters (β) based on a random number generator or a pseudo-random number generator (e.g., a Mersenne Twister pseudo-random number generator). For example, the managing computing device 406 may select random values for each of the one or more shared parameters (f) within a corresponding weight tensor of an artificial neural network. In yet other embodiments, the managing computing device 406 may initialize the shared function (f) and the one or more shared parameters (β) such that the one or more shared parameters are each at the midpoint of all possible values for the one or more shared parameters (β). For example, if the one or more shared parameters (β) represent a weight tensor (and each parameter of the one or more shared parameters (β) represents a weight), all values of the one or more shared parameters (β) may be initialized to 0.5 (midpoint between 0.0 and 1.0) by the managing computing device 406.

Figure 12A:
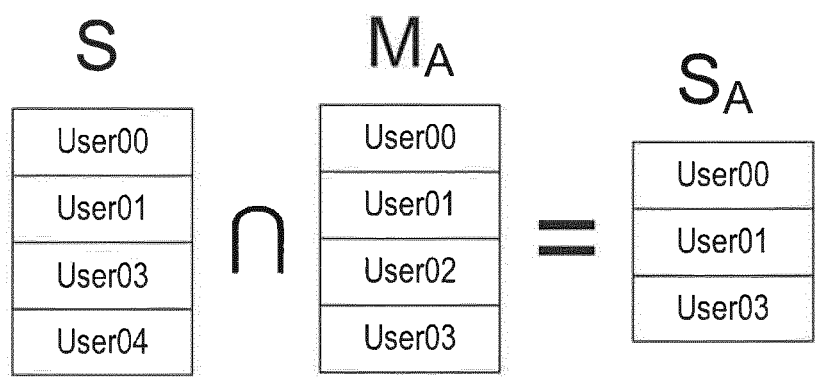
FIG. 12A illustrates a sublist of objects for a dataset, according to example embodiments.
Figure 12B:
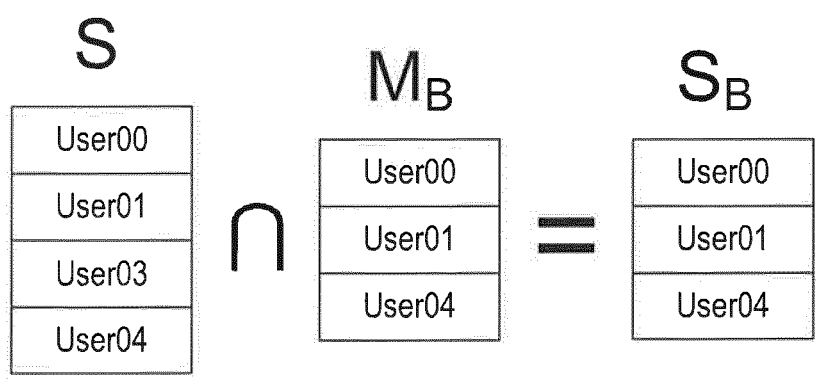
FIG. 12B illustrates a sublist of objects for a dataset, according to example embodiments.

FIGS. 12A and 12B are illustrations of operation 428 of method 400. As described with reference to FIG. 4C, at operation 428, the method 400 may include client computing device A 402 determining a sublist of objects ($S_A$) for dataset A ($X_A$). The sublist of objects ($S_A$) may be based on an intersection of the subset of identifiers (S) and the list of identifiers ($M_A$) for dataset A ($X_A$). Similarly, at operation 428, the method 400 may include client computing device B 404 determining a sublist of objects ($S_B$) for dataset B ($X_B$). The sublist of objects ($S_B$) may be based on an intersection of the subset of identifiers (S) and the list of identifiers ($M_B$) for dataset B ($X_B$).

Figure 13A:
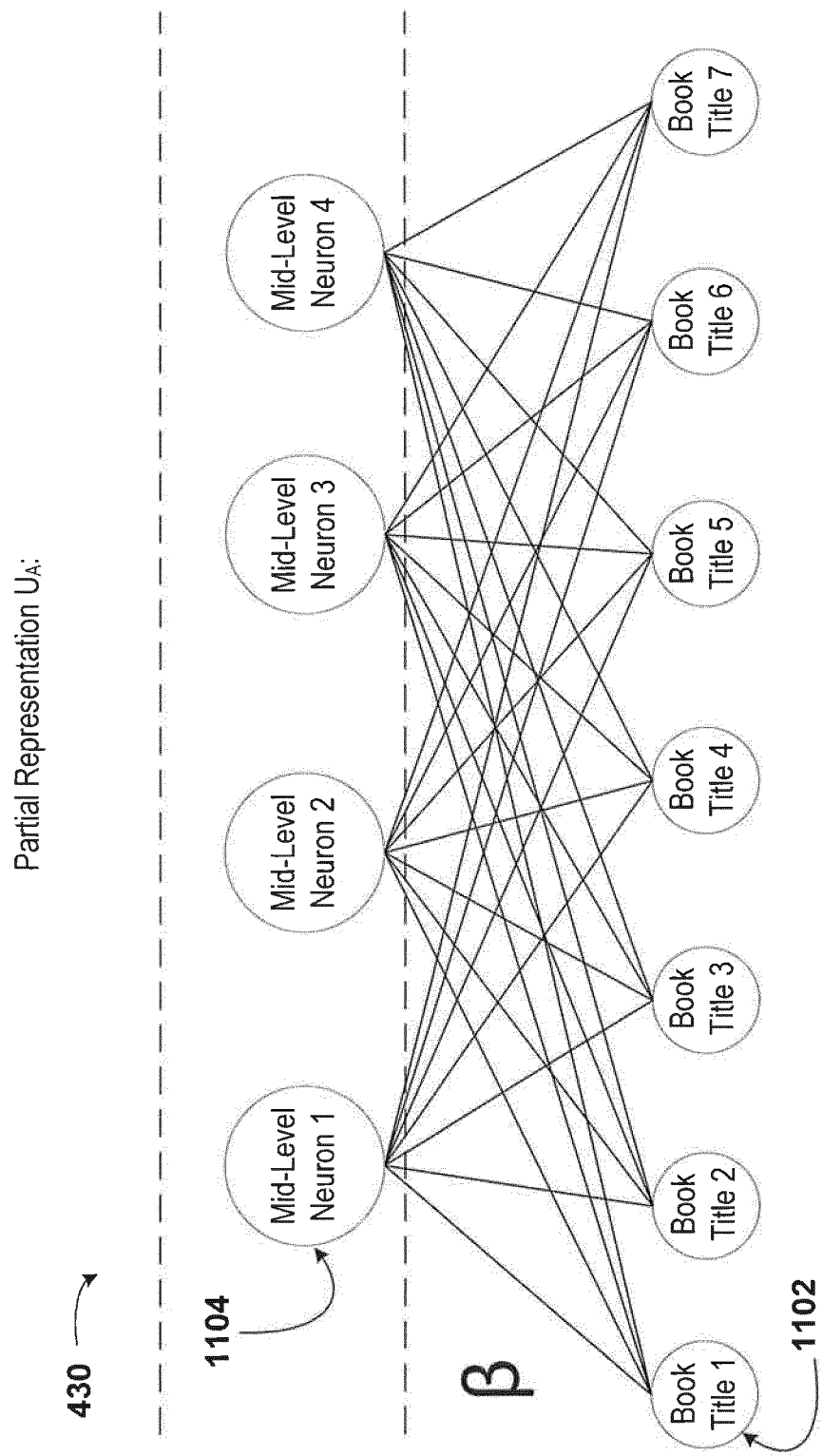
FIG. 13A illustrates a partial representation, according to example embodiments.
Figure 13B:
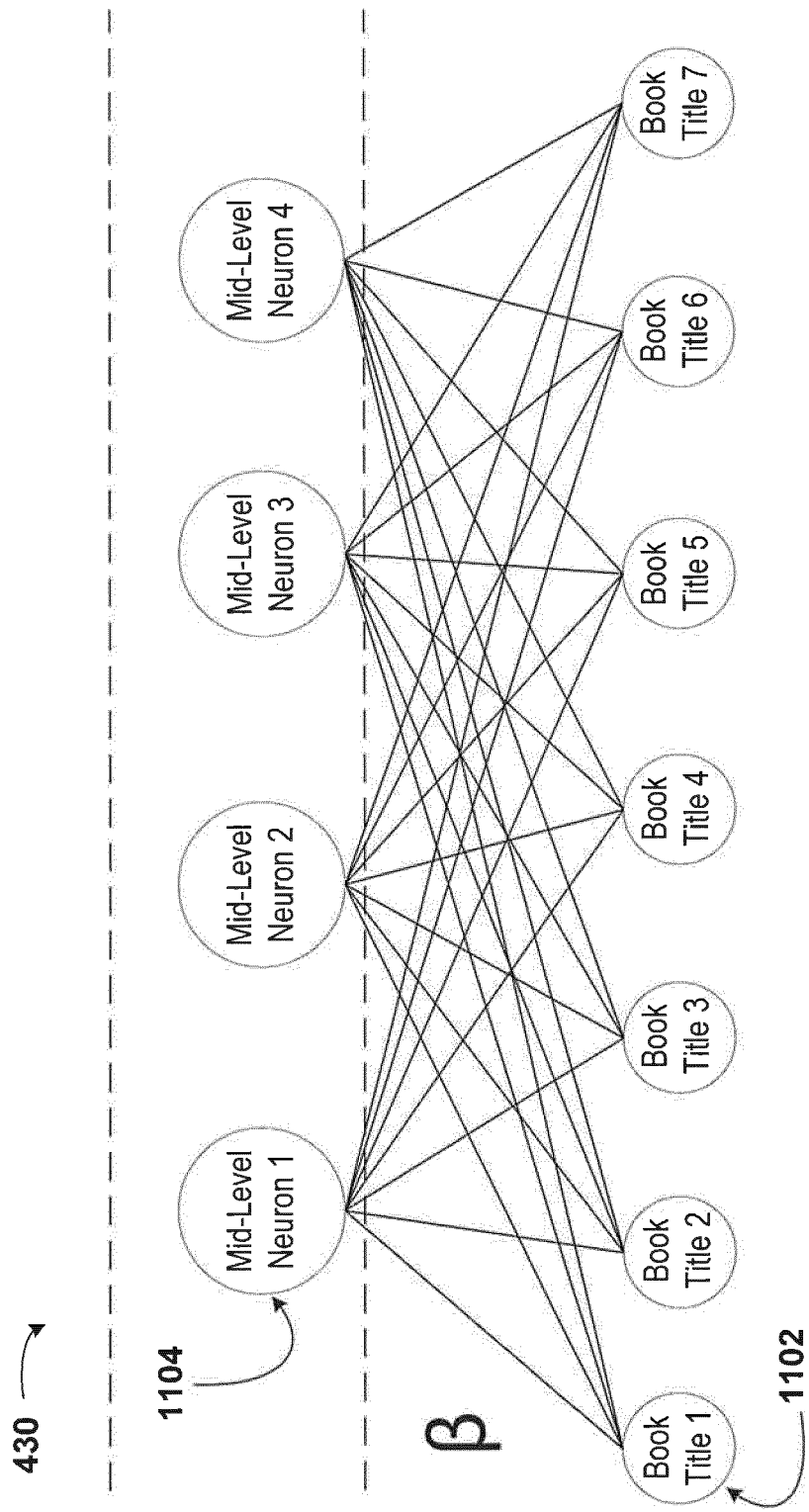
FIG. 13B illustrates a partial representation, according to example embodiments.

FIGS. 13A and 13B illustrate operation 430 of the method 400 illustrated in FIGS. 4B-4E, respectively. As described with reference to FIG. 4C, at operation 430, the method 400 may include the managing computing device 406 determining a partial representation ($U_A$) for dataset A ($X_A$). The partial representation ($U_A$) may be based on the sublist of objects ($S_A$) and the shared representation (U). Similarly as described with reference to FIG. 4C, at operation 430, the method 400 may include the managing computing device 406 determining a partial representation ($U_B$) for dataset B ($X_B$). The partial representation ($U_B$) may be based on the sublist of objects ($S_B$) and the shared representation (U). In FIGS. 13A and 13B, only one of the mid-level neurons 1104 and one of the first-level neurons 1102 are labeled, in order to avoid cluttering the figures.

In FIG. 13A, only those components of the shared representation (U) that correspond to the sublist of objects ($S_A$) may be included in the partial representation ($U_A$). For example, the partial representation ($U_A$) may not include data based on calculations done with respect to objects that are not included in the sublist of objects ($S_A$). Returning to the matrix above where $\overline{FLN} \times \beta = \overline{MLN}$, if the fourth row of $\overline{FLN}$ corresponds to "User04" (an object that is not present in the sublist of objects ($S_A$)), then the corresponding fourth row of $\overline{MLN}$ may not be present in the partial representation ($U_A$), because "User04" is not included in the sublist of objects ($S_A$). Hence, while the one or more shared parameters (β) may be applied to each of the objects within the subset (Z) of the list of unique objects ($X_{Comb}$), only the values of the partial representation ($U_A$) corresponding to those objects that are included in a respective sublist of objects ($S_A$) may be included in the respective partial representation ($U_A$). In some embodiments (e.g., artificial neural network embodiments), as described above, this may correspond to only certain rows of $\overline{MLN}$ being present in the partial representation ($U_A$).

Similarly in FIG. 13B, only those components of the shared representation (U) that correspond to the sublist of objects ($S_B$) may be included in the partial representation ($U_B$). For example, the partial representation ($U_B$) may not include data based on calculations done with respect to objects that are not included in the sublist of objects ($S_B$). Returning to the matrix above where $\overline{FLN} \times \beta = \overline{MLN}$, if the third row of $\overline{FLN}$ corresponds to "User03" (an object that is not present in the sublist of objects ($S_B$)), then the corresponding third row of $\overline{MLN}$ may not be present in the partial representation ($U_B$), because "User03" is not included in the sublist of objects ($S_B$). Hence, while the one or more shared parameters (β) may be applied to each of the objects within the subset (Z) of the list of unique objects ($X_{Comb}$), only the values of the partial representation ($U_B$) corresponding to those objects that are included in a respective sublist of objects ($S_B$) may be included in the respective partial representation ($U_B$). In some embodiments (e.g., artificial neural network embodiments), as described above, this may correspond to only certain rows of $\overline{MLN}$ being present in the partial representation ($U_B$).

In some embodiments, as described with reference to FIG. 4C, after determining the sublists of objects ($S_A$/$S_B$) and the partial representations ($U_A$/$U_B$) for the datasets ($X_A$/$X_B$), the managing computing device 406 (e.g., at operations 432 and 434 of method 400) may transmit the sublists of objects ($S_A$/$S_B$) and the partial representations ($U_A$/$U_B$) for the respective datasets ($X_A$/$X_B$) to the respective client computing devices (client computing device A 402/client computing device B 404).

Figure 14A:
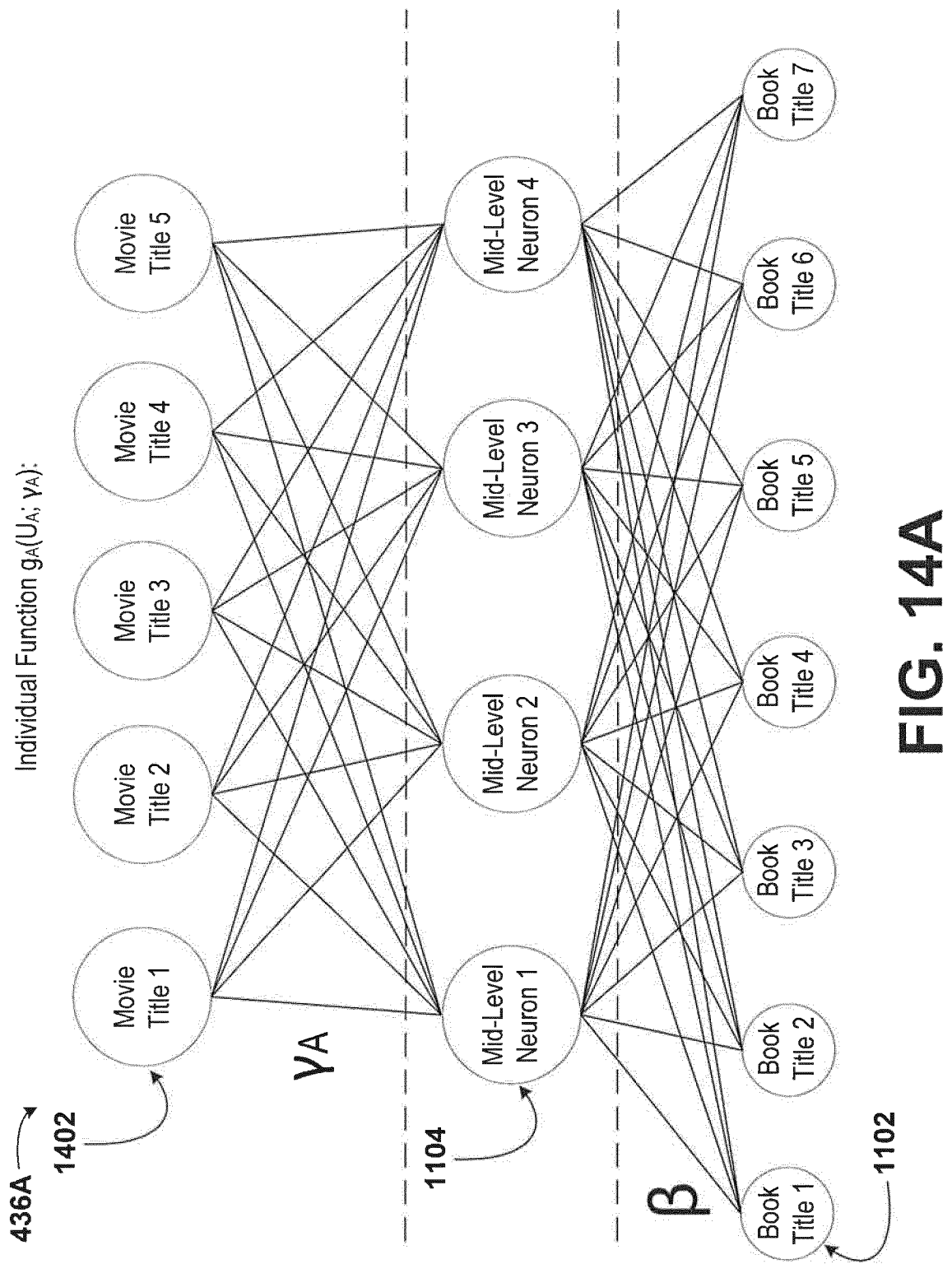
FIG. 14A illustrates an individual function, according to example embodiments.

FIGS. 14A and 14B illustrate portions of operations 436A and 436B of the method 400 illustrated in FIGS. 4B-4E, respectively. As described with reference to FIG. 4D, at operation 436A, the method 400 may include client computing device A 402 determining a set of predicted values ($\hat{Y}_A$) that corresponds to dataset A ($X_A$). The set of predicted values may be based on the partial representation ($U_A$) and an individual function ($g_A$) with one or more individual parameters ($\gamma_A$) corresponding to dataset A ($X_A$). Similarly as described with reference to FIG. 4D, at operation 436B, the method 400 may include client computing device B 404 determining a set of predicted values ($\overline{Y}_B$) that corresponds to dataset B ($X_B$). The set of predicted values may be based on the partial representation ($U_B$) and an individual function ($g_B$) with one or more individual parameters ($\gamma_B$) corresponding to dataset B ($X_B$).

In example embodiments employing an artificial neural network model, the sets of predicted values ($\overline{Y}_A/\hat{Y}_B$) may correspond to a set of output values for each upper-level neuron 1402 for each object in the respective sublist of objects ($S_A/S_B$), as illustrated in FIGS. 14A and 14B. Using the example datasets ($X_A/X_B$) and corresponding sets of recorded values ($Y_A/Y_B$) illustrated in FIGS. 5A and 5B, the sets of predicted values ($\hat{Y}_A/\hat{Y}_B$) may correspond to ratings of "Movie Title 1," "Movie Title 2," "Movie Title 3," "Movie Title 4," and "Movie Title 5." Also as illustrated, these sets of predicted values ($\hat{Y}_A/\hat{Y}_B$) may be determined based on the values of the mid-level neurons 1104 (which themselves are based on the first-level neurons 1102 multiplied by the one or more shared parameter) multiplied by the respective one or more individual parameters ($\gamma_A/\gamma_B$) corresponding to the dataset ($X_A/X_B$). These individual parameters may be stored in a weight tensor (e.g., weight matrix) ($A/f_B$), for example. In alternate embodiments, where a different machine learning model is used (e.g., other than an artificial neural network), the one or more individual parameters ($\gamma_A/\gamma_B$) may correspond to other parameters of the machine learning model (e.g., parameters other than a weight tensor). As in FIGS. 11, 13A, and 13B, the dashed lines illustrate that, in some embodiments, there may be additional hidden layers (e.g., one, two, three, four, five, six, seven, eight, nine, ten, fifteen, sixteen, twenty, thirty-two, or sixty-four hidden layers) between the layers of the artificial neural network illustrated.

In FIGS. 14A and 14B, only a portion of the respective figure represents the individual function ($g_A/g_B$). The portion representing the individual function ($g_A/g_B$) is the mid-level neurons 1104 connected to the upper-level neurons 1402. The connections between the mid-level neurons 1104 and the first-level neurons 1102, as well as the first-level neurons 1102 themselves, are illustrated only to provide context for the respective individual functions ($g_A/g_B$). For example, the respective individual functions ($g_A/g_B$) each only act on the partial representation ($U_A/U_B$) rather than the entire shared representation (U). As with above, only a single first-level neuron 1102, a single mid-level neuron 1104, and a single upper-level neuron 1402 are labeled to avoid cluttering the figures.

The variables, as described below, that use subscript 'i', are intended to reference the corresponding dataset. For example, the subscript 'i' may be replaced with an 'A' when referring to any variable corresponding to dataset A ($X_A$) and may be replaced with a 'B' when referring to any variable corresponding to dataset B ($X_B$). Hence, the individual function ($g_i$) corresponding to a given dataset may be replaced with variable names ($g_i \rightarrow g_A/g_B$), where appropriate. Similar replacement may be used for the partial representation for a given dataset ($U_i \rightarrow U_A/U_B$) and the individual parameter for a given dataset ($\gamma_i \rightarrow \gamma_A/\gamma_B$).

As described above, the shared representation (U) may be defined by the shared function (f) and the objects in the subset (Z) (e.g., $U:=f(Z;\beta)$). Further, the shared function (f) may correspond to one or more layers of an artificial neural network model, as illustrated in FIGS. 11, 13A, and 13B. Similar to the definition of the shared representation (U), an individual representation ($I_A/I_B$) may be generated for each dataset ($X_A/X_B$) by each client computing device (client computing device A 402/client computing device B), respectively. The individual representation ($I_A/I_B$) may be defined analogously to the shared representation (U). Represented mathematically, this definition of the individual representation ($I_i$), based on the individual function corresponding to a given dataset ($g_i$), the partial representation for a given dataset ($U_i$), and the one or more individual parameters for a given dataset ($\gamma_i$), may correspond to:

$$I_i:=g_i(U_i;\gamma_i) \rightarrow \overline{MLN} \times \gamma_i = \overline{ULN}$$

where $\overline{MLN}$ is a tensor (e.g., matrix) representing the input values for each of the mid-level neurons 1104 taken from the respective partial representation for a given dataset ($U_i$), $\overline{\gamma}_i$ is a weight tensor representing the one or more individual parameters for a given dataset ($\gamma_i$) that define the individual function for a given dataset ($g_i$) (e.g., that define how values of the upper-level neurons 1402 depend upon values of the mid-level neurons 1104), and $\overline{ULN}$ is a tensor (e.g., matrix) representing the output values for each of the upper-level neurons 1402. As shown above, the individual representations ($I_i$) may be defined by the individual functions for a given dataset ($g_i$) and the partial representation ($U_i$) (e.g., $I:=g_i(U_i;\gamma_i)$). As illustrated, each individual function ($g_i$) may correspond to at least a portion of one or more second layers of an artificial neural network model. At least one of the one or more first layers that correspond to the shared function (f) described above may be an input layer to at least one of the one or more second layers that correspond to the individual function ($g_i$).

In the example of FIG. 14A, $\overline{MLN}$ may be a 3×4 matrix (4 mid-level neuron 1104 values for each of 3 objects in the sublist of objects ($S_A$)), $Y_A$ may be a 4×5 matrix (showing how the 5 upper-level neurons 1402 each depend on the 4 mid-level neurons 1104), and $\overline{ULN}$ may be a 3×5 matrix (5 upper-level neuron 1402 values for each of 3 objects in the sublist of objects ($S_A$)). $\overline{ULN}$ may be a sparse matrix, as not every object ("user") has provided a value ("rating") for each feature ("book title") in the dataset ($X_A$) received by the managing computing device 406. In other words, because the dataset ($X_A$) provided by client computing device A 402 may not be complete, $\overline{FLN}$, as described above, may be incomplete/sparse (e.g., have entries with no values). Consequently, based on the two layers of matrix multiplication described above, for example, $\overline{ULN}$ may also be a sparse matrix.

In the example of FIG. 14B, $\overline{MLN}$ may also be a 3×4 matrix (4 mid-level neuron 1104 values for each of 3 objects in the sublist of objects ($S_B$)), $\overline{\gamma}_B$ may be a 4×9 matrix (showing how the 9 upper-level neurons 1402 each depend on the 4 mid-level neurons 1104), and $\overline{ULN}$ may be a 3×9 matrix (9 upper-level neuron 1402 values for each of 3 objects in the sublist of objects ($S_B$)). $\overline{ULN}$ may be a sparse matrix, as not every object ("user") has provided a value ("rating") for each feature ("book title") in the dataset ($X_B$) received by the managing computing device 406. In other words, because the dataset ($X_B$) provided by client computing device B 404 may not be complete, $\overline{FLN}$, as described above, may be incomplete/sparse (e.g., have entries with no values). Consequently, based on the two layers of matrix multiplication described above, for example, $\overline{ULN}$ may also be a sparse matrix.

In some embodiments, prior to computing an individual representation (I), the individual function ($g_i$) and the one or more individual parameters ($\gamma_i$) (e.g., stored within a "weight" tensor in artificial neural network embodiments) may be initialized by the respective client computing device. The respective client computing devices may initialize the individual function ($g_i$) and the one or more individual parameters ($\gamma_i$) corresponding to the respective dataset ($X_A/X_B$) based on a random number generator or a pseudorandom number generator (e.g., a Mersenne Twister pseudorandom number generator).

Figure 15A:
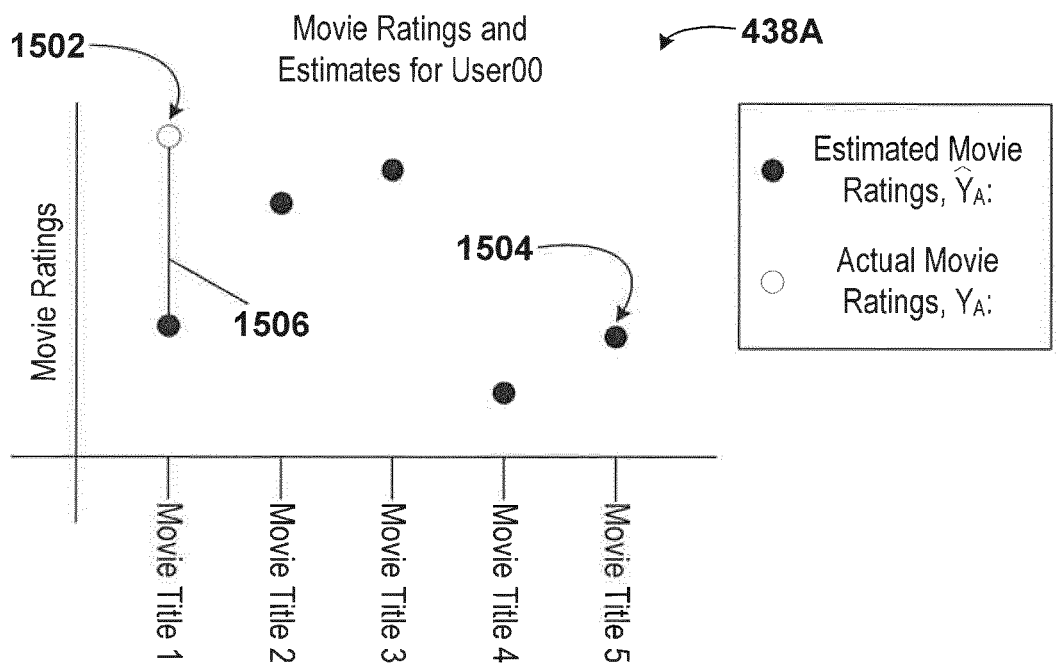
FIG. 15A illustrates a set of predicted values, according to example embodiments.
Figure 15B:
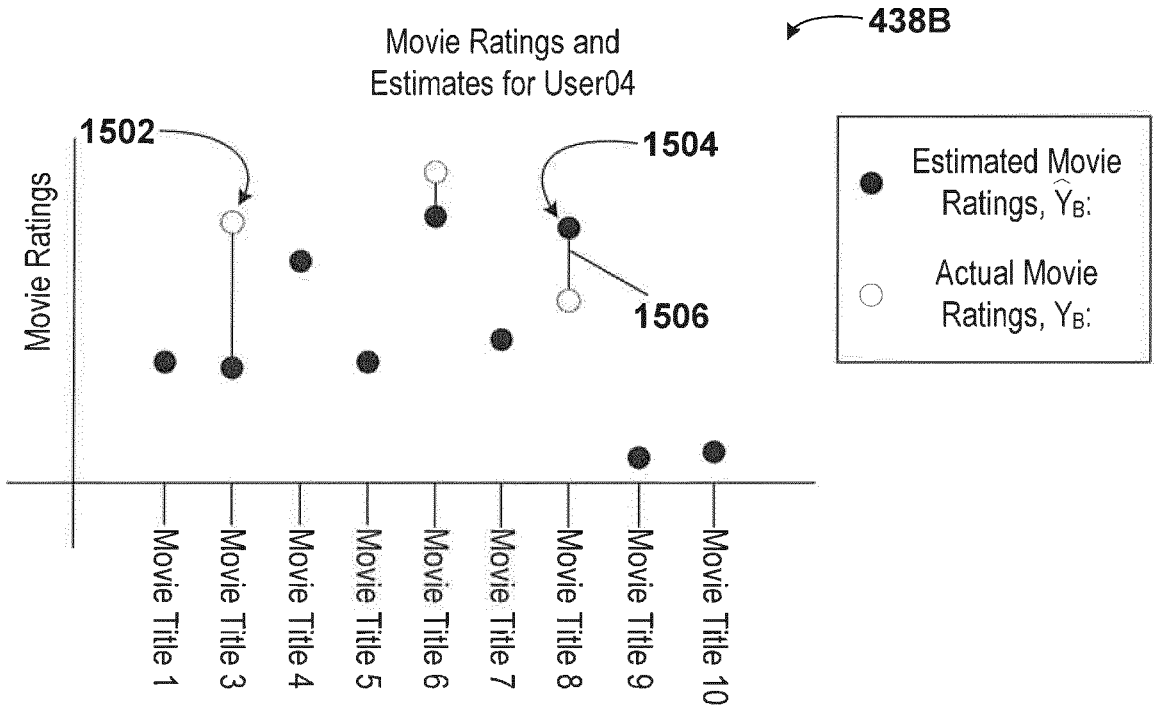
FIG. 15B illustrates a set of predicted values, according to example embodiments.

FIGS. 15A and 15B illustrate portions of operations 438A and 438B of the method 400 illustrated in FIGS. 4B-4E, respectively. As described with reference to FIG. 4D, at operation 438A, the method 400 may include client computing device A 402 determining an error ($E_A$) for dataset A ($X_A$). The error ($E_A$) may be based on an individual loss function ($L_A$) for dataset A ($X_A$), the set of predicted values ($\hat{Y}_A$) that corresponds to dataset A ($X_A$), the sublist of objects ($S_A$), and non-empty entries ($W_A$) in the set of recorded values ($Y_A$) corresponding to dataset A ($X_A$). Similarly as described with reference to FIG. 4D, at operation 438B, the method 400 may include client computing device B 402 determining an error ($E_B$) for dataset B ($X_B$). The error ($E_B$) may be based on an individual loss function ($L_B$) for dataset B ($X_B$), the set of predicted values ($\hat{Y}_B$) that corresponds to dataset B ($X_B$), the sublist of objects ($S_B$), and non-empty entries ($W_B$) in the set of recorded values ($Y_B$) corresponding to dataset B ($X_B$).

To generate the data represented in FIGS. 15A and 15B, the set of predicted values 1504 ($\hat{Y}_A/\hat{Y}_B$) are compared to the set of recorded values 1502 ($Y_A/Y_B$) corresponding to each dataset ($X_A/X_B$). Using the example datasets ($X_A/X_B$) and corresponding sets of recorded values 1502 ($Y_A/Y_B$) illustrated in FIGS. 5A and 5B, the sets of predicted values 1504 ($\hat{Y}_A/\hat{Y}_B$) correspond to estimated movie ratings, and the sets of recorded values 1502 ($Y_A/Y_B$) correspond to actual movie ratings. In FIG. 15A, the set of recorded values 1502 ($Y_A$) for "User00" (e.g., a first row of a matrix corresponding to the set of recorded values 1502 ($Y_A$)) is compared with the set of predicted values 1504 ($\hat{Y}_A$) for "User00" (e.g., a first row of a matrix corresponding to the set of predicted values 1504 ($\hat{Y}_A$)). In FIG. 15B, the set of recorded values 1502 ($Y_B$) for "User04" (e.g., a third row of a matrix corresponding to the set of recorded values 1502 ($Y_B$)) is compared with the set of predicted values 1504 ($\hat{Y}_B$) for "User04" (e.g., a third row of a matrix corresponding to the set of predicted values 1504 ($\hat{Y}_B$)).

For both datasets, the set of recorded values 1502 ($Y_A/Y_B$) and the set of predicted values 1504 ($\hat{Y}_A/\hat{Y}_B$) are illustrated in FIGS. 15A and 15B by way of example. Similar plots may be made for the sets of recorded values 1502 ($Y_A/Y_B$) and the sets of predicted values 1504 ($\hat{Y}_A/\hat{Y}_B$) for other objects in the respective sublists of objects ($S_A/S_B$). For example, "User01" and "User03" from the sublist of objects ($S_A$) corresponding to dataset A ($X_A$) could also be plotted. There are some features (e.g., "movie titles" using the example datasets ($X_A/X_B$) and the example sets of recorded values ($Y_A/Y_B$) from FIGS. 5A and 5B) for which there are no corresponding recorded values 1502 (e.g., "Movie Title 2" for "User00"). Hence, for these features, there is no corresponding recorded value 1502 (e.g., "Actual Movie Rating" ($Y_A/Y_B$)) illustrated in FIGS. 15A and 15B.

The sets of predicted values 1504 ($\hat{Y}_A/\hat{Y}_B$), similar to the sets of recorded values 1502 ($Y_A/Y_B$) may be stored as a tensor (e.g., a matrix). The sets of predicted values 1504 ($\hat{Y}_A/\hat{Y}_B$) may then be compared to the sets of recorded values 1502 ($Y_A/Y_B$) to compute an error for the respective dataset ($X_A/X_B$). The error ($E_A/E_B$) may be calculated according to an individual loss function ($L_A/L_B$). For example, the error ($E_A/E_B$) corresponding to each dataset ($X_A/X_B$) may be the sum of the individual loss function ($L_A/L_B$) evaluated at each non-zero entry ($W_A/W_B$) in a tensor representing the set of recorded values 1502 ($Y_A/Y_B$). As illustrated in FIG. 15A, the individual loss function ($L_A/L_B$) evaluated for a given entry may be based on the difference 1506 between the predicted value 1504 for that entry and the recorded value 1502 for that entry. Only one difference 1506 is labeled in each of FIGS. 15A and 15B to avoid cluttering the figures. Mathematically, the error ($E_A$) corresponding to dataset A ($X_A$) may be represented by:

$$E_A = \Sigma_{W_A}(\hat{Y}_{A,W_A}, Y_{A,W_A})$$

The above equation represents that the error ($E_A$) corresponding to dataset A ($X_A$) equals the sum of the individual loss function ($L_A$), evaluated between the entry in the set of predicted values ($\hat{Y}_A$) and the entry in the set of recorded values ($Y_A$), for each non-empty entry ($W_A$) of each object in the sublist of objects ($S_A$) corresponding to the set of recorded values ($Y_A$) for dataset A ($X_A$). The addend in the above sum may be referred to as a "partial error value." The mathematical representation for dataset B ($X_B$) is analogous with the mathematical representation for dataset A ($X_A$), mutatis mutandis.

In some embodiments, the individual loss functions ($L_A/L_B$) may include at least one of: a quadratic loss function, a logarithmic loss function, a hinge loss function, a quantile loss function, or a loss function associated with the Cox proportional hazard model. Further, in some embodiments, different client computing devices may use the same individual loss functions (e.g., the individual loss function used by each client computing device may be prescribed by the managing computing device 406), referred to as a "shared loss function." For example both client computing device A 402 and client computing device B 404 may use a quadratic loss function for respective individual loss functions ($L_A/L_B$) (e.g., $L_A(j,k)=(j-k)^2$). In alternate embodiments, the individual loss functions ($L_A/L_B$) corresponding to different datasets ($X_A/X_B$) may be different. However, in such embodiments, certain results generated (e.g., errors ($E_A/E_B$)) by a dataset's ($X_A/X_B$) respective client computing device may be normalized prior to or after transmission to the managing computing device 406, such that the results can be meaningfully compared against one another even though different individual loss functions ($L_A/L_B$) were used. In some such embodiments, information about the particular individual loss function ($L_A/L_B$) used by a client computing device and/or about a corresponding set of recorded values ($Y_A/Y_B$) may be transmitted to the managing computing device 406. The information about the particular individual loss function ($L_A/L_B$) used and/or about the corresponding set of recorded values ($Y_A/Y_B$) may be used by the managing computing device 406 to perform a normalization.

In some embodiments, as illustrated and described with reference to FIG. 4D, the method 400 may also include updating one or more individual parameters ($\gamma_A/\gamma_B$). For example, at operation 440A, the method 400 may include client computing device A 402 updating the one or more individual parameters ($\gamma_A$) for dataset A ($X_A$). Similarly, at operation 440B, the method 400 may include client computing device B 404 updating the one or more individual parameters ($\gamma_B$) for dataset B ($X_B$). Updating the one or more individual parameters ($\gamma_A/\gamma_B$) may include performing gradient descent with respect to the calculated respective error ($E_A/E_B$). Additionally or alternatively (e.g., when the machine learning model being employed is an artificial neural network), updating the one or more individual parameters ($\gamma_A/\gamma_B$) may include back-propagating the respective errors ($E_A/E_B$) based on weight tensors (e.g., weight matrix) ($\bar{\gamma}_A/\bar{\gamma}_B$). Based on the back-propagated errors ($E_A/E_B$), the respective one or more individual parameters ($\gamma_A/\gamma_B$) may be updated, which could result in an improvement to the respective sets of predicted values ($\hat{Y}_A/\hat{Y}_B$).

The amount by which the respective one or more individual parameters ($\gamma_A/\gamma_B$) are updated may correspond to a respective individual learning rate ($R_A/R_B$). The individual learning rates ($R_A/R_B$) may be determined by each of the client computing devices independently, in some embodiments. In other embodiments, the individual learning rates ($R_A/R_B$) may be determined by the managing computing device 406 and then transmitted to the client computing devices, individually. Alternatively, the individual learning rates ($R_A/R_B$) may be inherent in a gradient descent method used by each respective client computing device. In some embodiments, either or both of the individual learning rates ($R_A/R_B$) may include at least one of: an exponentially decayed learning rate, a harmonically decayed learning rate, a step-wise exponentially decayed learning rate, or an adaptive learning rate.

In some embodiments, as illustrated and described with reference to FIG. 4D, the method 400 may also include determining one or more feedback values ($C_A/C_B$). For example, at operation 442A, the method 400 may include client computing device A 402 determining one or more feedback values ($C_A$). The one or more feedback values ($C_A$) may be used to determine a change in the partial representation ($U_A$) that corresponds to an improvement in the set of predicted values ($\hat{Y}_A$). Similarly, at operation 442B, the method 400 may include client computing device B 404 determining one or more feedback values ($C_B$). The one or more feedback values ($C_B$) may be used to determine a change in the partial representation ($U_B$) that corresponds to an improvement in the set of predicted values ($\hat{Y}_B$). The one or more feedback values ($C_A/C_B$) may correspond to back-propagated errors ($E_A/E_B$) (e.g., based on weight tensors ($\overline{\gamma}_A/\overline{\gamma}_B$)).

In some embodiments, determining one or more feedback values ($C_A/C_B$) may correspond to performing, by the respective client computing device (client computing device A 402/client computing device B 404), a gradient descent method. Additionally or alternatively, when determining a change in the respective partial representation ($U_A/U_B$) that corresponds to an improvement in the respective sets of predicted values ($\hat{Y}_A/\hat{Y}_B$), the respective sets of predicted values may correspond to a threshold improvement value. The threshold improvement value may be based on a shared learning rate ($\eta$). In some embodiments, the shared learning rate ($\eta$) may be determined by the managing computing device 406 and transmitted by the managing computing device 406 to each of the client computing devices. Additionally or alternatively, in some embodiments, the shared learning rate ($\eta$) may be defined by the gradient descent method used by the client computing devices. For example, the client computing devices may each use the same gradient descent method (e.g., a shared gradient descent method prescribed by the managing computing device 406) that has an associated shared learning rate ($\eta$). Further, the shared learning rate ($\eta$) may include at least one of: an exponentially decayed learning rate, a harmonically decayed learning rate, or a step-wise exponentially decayed learning rate. In other embodiments, the shared learning rate ($\eta$) may include an adaptive learning rate.

In some embodiments, when determining a change in the respective partial representation ($U_A/U_B$) that corresponds to an improvement in the respective sets of predicted values ($\hat{Y}_A/\hat{Y}_B$), improvement in the set of predicted values ($\hat{Y}_A/\hat{Y}_B$) corresponds to a threshold improvement value defined by an individual learning rate ($R_A/R_B$) that is determined by each of the client computing devices independently. In some embodiments, the individual learning rate ($R_A/R_B$) may include at least one of: an exponentially decayed learning rate, a harmonically decayed learning rate, or a step-wise exponentially decayed learning rate.

In some embodiments, the one or more feedback values ($C_A/C_B$) may be organized into respective feedback tensors ($\overline{C}_A/\overline{C}_B$). Each feedback tensor ($\overline{C}_A/\overline{C}_B$) may have a dimensionality that is equal to a dimensionality of the respective partial representation ($U_A/U_B$). For example, using the example datasets ($X_A/X_B$) and sets of recorded values ($Y_A/Y_B$) illustrated in FIGS. 5A and 5B, corresponding feedback tensors ($\overline{C}_A/\overline{C}_B$) developed using the method 400 may be two-dimensional feedback tensors (i.e., feedback matrices).

In some embodiments, as illustrated and described with reference to FIG. 4D, the method 400 may also include (e.g., at operation 444) client computing device A 402 transmitting the one or more feedback values ($C_A$) to the managing computing device 406. Additionally or alternatively, the method 400 may include (e.g., at operation 446) client computing device B 404 transmitting the one or more feedback values ($C_B$) to the managing computing device 406. In some embodiments, client computing device B 406 may transmit the one or more feedback values ($C_B$) to the managing computing device 406 prior to or simultaneous with client computing device A 404 transmitting the one or more feedback values ($C_A$) to the managing computing device 406. Alternatively, in some embodiments, only one of the client computing devices (e.g., client computing device A 402), rather than both, may transmit one or more feedback values (e.g., $C_A$) to the managing computing device 406.

In some embodiments, as illustrated and described with reference to FIG. 4E, the method 400 may also include (e.g., at operation 448) the managing computing device 406 determining one or more aggregated feedback values ($C_{Comb}$). The one or more aggregated feedback values ($C_{Comb}$) may be based on the sublists of objects ($S_A/S_B$) corresponding to dataset A ($X_A$) and dataset B ($X_B$), respectively, and the one or more feedback values ($C_A/C_B$) from client computing device A 402 and client computing device B 404, respectively. In some embodiments, determining the one or more aggregated feedback values ($C_{Comb}$) may include the managing computing device 406 defining, based on the sublists of objects ($S_A/S_B$) and the one or more feedback values ($C_A/C_B$) from the client computing devices, a tensor ($C_{Comb}$) representing the one or more aggregated feedback values ($C_{Comb}$). Further, determining the one or more aggregated feedback values ($C_{Comb}$) may also include the managing computing device 406 summing, based on the sublists of objects ($S_A/S_B$), those feedback values of the one or more feedback values ($C_A/C_B$) from the client computing devices that correspond to objects in the sublists of objects ($S_A/S_B$) that have shared identifiers into a shared entry of the tensor ($\overline{C}_{Comb}$) representing the one or more aggregated feedback values ($C_{Comb}$).

In some embodiments, the one or more aggregated feedback values ($C_{Comb}$) may be organized into an aggregated feedback tensor ($\overline{C}_{Comb}$). The aggregated feedback tensor ($\overline{C}_{Comb}$) may have a dimensionality that is equal to a dimensionality of the shared representation (U). For example, using the example datasets ($X_A/X_B$) and sets of recorded values ($Y_A/Y_B$) illustrated in FIGS. 5A and 5B, corresponding aggregated feedback tensors ($C_{Comb}$) developed using the method 400 may be a two-dimensional aggregated feedback tensor (i.e., a feedback matrix).

In some embodiments, as illustrated and described with reference to FIG. 4E, the method 400 may also include (e.g., at operation 450) the managing computing device 406 updating the one or more shared parameters ($\beta$) based on the one or more aggregated feedback values ($C_{Comb}$). In some embodiments, updating the one or more shared parameters ($\beta$) based on the more aggregated feedback values ($C_{Comb}$) may include evaluating a sum of partial derivatives, where each of the partial derivatives are partial derivatives of the error ($E_A/E_B$) for a respective dataset ($X_A/X_B$) with respect to the one or more shared parameters (β). Such a sum may be represented mathematically as:

$$\sum_i \frac{\partial E_i}{\partial \beta} = C_{Comb}\left(\frac{\partial U}{\partial \beta}\right)$$

where 'i' in the above sum is an index corresponding to a respective dataset (e.g., dataset A ($X_A$)).

Additionally or alternatively, in some embodiments, updating the one or more shared parameters (β) based on the more aggregated feedback values ($C_{Comb}$) may include evaluating a sum of products of first partial derivatives and second partial derivatives, where each of the first partial derivatives are partial derivatives of the error ($E_A/E_B$) for a respective dataset ($X_A/X_B$) with respect to the respective partial representation ($U_A/U_B$), and where each of the second partial derivatives are partial derivatives of the respective partial representation ($U_A/U_B$) with respect to the one or more shared parameters (β). Such a sum may be represented mathematically as:

$$\sum_i \frac{\partial E_i}{\partial U_i}\left(\frac{\partial U_i}{\partial \beta}\right) = C_{Comb}\left(\frac{\partial U}{\partial \beta}\right)$$

where 'i' in the above sum is an index corresponding to a respective dataset (e.g., dataset A ($X_A$)).

FIGS. 16A-16C illustrate combinations of datasets and sets of recorded values, analogous to dataset A ($X_A$) and the set of recorded values ($Y_A$) illustrated in FIG. 5A and dataset B ($X_B$) and the set of recorded values ($Y_B$) illustrated in FIG. 5B. The combinations of datasets and sets of recorded values are provided as additional examples of datasets and sets of recorded values. The types of representation, data, features, dimensions, and values (e.g., for various entries in the datasets and/or the sets of recorded values) are provided as examples, and are not meant to be limiting. In various embodiments contemplated herein, various alternative data structures, types of data, amounts of data, and/or representations of data may be used for datasets and sets of recorded values.

Illustrated in FIG. 16A is a dataset 1602 ($X_{Binary}$) and a corresponding set of recorded values 1604 ($Y_{Binary}$). The dataset 1602 ($X_{Binary}$) includes binary values for each relationship between an object and a feature (e.g., corresponding to insurance data). In FIG. 16A, the black entries in dataset 1602 ($X_{Binary}$) may correspond to entries for which the object exhibits the given feature. For example, object "Jordan" may exhibit "fewer than 3 accidents," "a restricted license," and be "insured for accidents." The corresponding set of recorded values 1604 ($Y_{Binary}$) illustrated in FIG. 16A may include binary data, textual data (e.g., classification data), and numeric data corresponding to various features. For example, object "Jason" may exhibit an "age" value of "22" (numeric data), a "gender" of "M" (textual data), a "state of residence" of "KY" (textual data), an "income (in thousands)" of "42" (numeric data), a "number of children" of "2" (numeric data), and be "married" (binary data).

In some embodiments of both datasets and sets of recorded values, data for values of various entries may be purely binary data, purely textual data (e.g., classification data), or purely numeric data, for example. In alternate embodiments of both datasets and sets of recorded values, data for values of various entries may be a combination of binary data, textual data (e.g., classification data), and numeric data. In still other embodiments, data may be in the form of sound recordings (e.g., used to develop a machine learning model that can be used to perform voice recognition) or images (e.g., used to develop a machine learning model that can be used to perform object recognition).

In some embodiments (e.g., embodiments that are not illustrated), datasets and corresponding sets of recorded values may have greater than two dimensions. In such example embodiments, the datasets and the corresponding sets of recorded values may correspond to n-dimensional tensors (e.g., rather than two-dimensional tensors, i.e., matrices).

Illustrated in FIG. 16B is a dataset 1612 ($X_{Drug\ Discovery}$) and a corresponding set of recorded values 1614 ($Y_{Drug\ Discovery}$). The dataset 1612 ($X_{Drug\ Discovery}$) and the set of recorded values 1614 ($Y_{Drug\ Discovery}$) may correspond to data related to pharmaceutical discovery (e.g., arising from a clinical trial). For example, the data in the dataset 1612 ($X_{Drug\ Discovery}$) and the corresponding set of recorded values 1614 ($Y_{Drug\ Discovery}$) may have been generated by a pharmaceutical corporation during the course of testing a variety of candidate pharmaceutical compounds using a variety of assays. As illustrated, the dataset 1612 ($X_{Drug\ Discovery}$) may relate a series of compounds to a series of chemical fingerprints and/or additional descriptors. The values of the entries of the dataset 1612 ($X_{Drug\ Discovery}$) may be binary. For example, object "compound B" exhibits "chemistry fingerprint 2" as well as "additional descriptor 3." In alternate embodiments, the values of the entries of the dataset 1612 ($X_{Drug\ Discovery}$) could be any combination of binary data, textual data (e.g., classification data), and numeric data. Also as illustrated, the corresponding set of recorded values 1614 ($Y_{Drug\ Discovery}$) may relate a series of compounds to a series of assay activities and concentrations for half-maximum activity (half-max). Some of the values of the entries of the set of recorded values 1614 ($Y_{Drug\ Discovery}$) may be binary, while other values of the entries may be numeric data. For example, object "compound C" exhibits "activity in assay 1," "activity in assay 6," a "concentration for half-max assay 5" of 0.2 (e.g., 0.2 Molar), and a "concentration for half-max assay 9" of 0.8 (e.g., 0.8 Molar). In alternate embodiments, the values of the entries of the corresponding set of recorded values 1614 ($Y_{Drug\ Discovery}$) could be any combination of binary data, textual data (e.g., classification data), and numeric data.

Illustrated in FIG. 16C is a dataset 1622 ($X_{Treatment}$) and a corresponding set of recorded values 1624 ($Y_{Treatment}$). The dataset 1622 ($X_{Treatment}$) and the set of recorded values 1624 ($Y_{Treatment}$) may correspond to data related to patient diagnosis and care (e.g., arising from doctor's records). For example, the data in the dataset 1622 ($X_{Treatment}$) and the corresponding set of recorded values 1624 ($Y_{Treatment}$) may have been generated by a doctor during the course of diagnosing and treating a patient. As illustrated, the dataset 1622 ($X_{Treatment}$) may relate a series of patients to a series of patient descriptors. The values of the entries of the dataset 1622 ($X_{Treatment}$) may be a combination of binary data, textual data (e.g., classification data), and numeric data. For example, object "patient A" exhibits "generic marker 1" as well as "family history of disease 2," has a value for "gender" corresponding "F," and has a value for "age" corresponding to "22" and a value of weight corresponding to "107." In alternate embodiments, the values of the entries of the dataset 1622 ($X_{Treatment}$) could be any combination of binary data, textual data (e.g., classification data), and numeric data. Also as illustrated, the corresponding set of recorded values 1624 ($Y_{Treatment}$) may relate a series of patients to a series of clinical diagnoses. The values of the entries of the set of recorded values 1624 ($Y_{Treatment}$) may be binary. For example, object "patient C" exhibits "clinical diagnosis 3," "clinical diagnosis 4," and "clinical diagnosis 6." In alternate embodiments, the values of the entries of the corresponding set of recorded values 1624 ($Y_{Treatment}$) could be any combination of binary data, textual data (e.g., classification data), and numeric data.

In some embodiments, all objects within a given dimension of a dataset or a corresponding set of recorded values may be the same (e.g., all objects within a first dimension of a dataset may be of designated type "user"). As illustrated in FIGS. 5A and 5B, the datasets ($X_A/X_B$) and the corresponding sets of recorded values ($Y_A/Y_B$) may each contain objects of the same type in each of their dimensions. For example, in a first dimension of dataset A ($X_A$), the objects may be designated type "user," in a second dimension of dataset A ($X_A$), the objects may be designated type "book," in a first dimension of set of recorded values A ($Y_A$), the objects may be of type "user," and in a second dimension of set of recorded values A ($Y_A$), the objects may be of type "movie." This may be analogous to dataset B ($X_B$) and corresponding set of recorded values B ($Y_B$) (i.e., in a first dimension of dataset B ($X_B$), the objects may be designated type "user," in a second dimension of dataset B ($X_B$), the objects may be designated type "book," in a first dimension of set of recorded values B ($Y_B$), the objects may be of type "user," and in a second dimension of set of recorded values B ($Y_B$), the objects may be of type "movie"). In alternate embodiments, this may not be the case. For example, a first dataset may have a first dimension with object type "user" and a second dimension with object type "book," whereas a second dataset (e.g., from a different client computing device) may have a first dimension with object type "user" and a second dimension with object type "movie."

Dimensions from different datasets containing different object types may still be used by the managing computing device 406 to develop a shared representation and to update the one or more shared parameters ($\beta$). In some embodiments, using different object types to develop a shared representation may include normalizing (e.g., by the managing computing device 406 or a respective client computing device) values corresponding to the different object types, such that those values can be meaningfully compared with one another.

The method described above, and various embodiments both explicitly and implicitly contemplated herein, may be used in a wide variety of applications. One example application includes a pharmaceutical discovery method. For example, in one embodiment, a first dimension of each of the plurality of datasets ($X_A/X_B$) transmitted to a managing computing device may include a plurality of chemical compounds and a second dimension of each of the plurality of datasets ($X_A/X_B$) may include descriptors of the chemical compounds (e.g., chemistry-derived fingerprints or descriptors identified via transcriptomics or image screening). In such an embodiment, entries in each of the plurality of datasets ($X_A/X_B$) may correspond to a binary indication of whether a respective chemical compound exhibits a respective descriptor. Further, in such an embodiment, a first dimension of each of the sets of recorded values ($Y_A/Y_B$) respectively corresponding to the plurality of datasets ($X_A/X_B$) may include the plurality of chemical compounds and a second dimension of each of the sets of recorded values ($Y_A/Y_B$) may include activities of the chemical compounds in a plurality of biological assays (e.g., concentration of a given product of a chemical reaction produced per unit time, fluorescence level, cellular reproduction rate, coloration of solution, pH of solution, or cellular death rate). In such an embodiment, entries in each of the sets of recorded values ($Y_A/Y_B$) may correspond to a binary indication of whether a respective chemical compound exhibits a respective activity.

The pharmaceutical discovery method may include the managing computing device 406 calculating a final shared representation ($U_{Final}$) of the datasets ($X_A/X_B$) based on the list of unique objects ($X_{Comb}$), the shared function (f), and the one or more shared parameters ($\beta$). The pharmaceutical discovery method may also include the managing computing device 406 transmitting the final shared representation ($U_{Final}$) of the datasets ($X_A/X_B$) to each of the client computing devices. The final shared representation ($U_{Final}$) of the datasets ($X_A/X_B$) may be usable by each of the client computing devices to determine a final set of predicted values ($\hat{Y}_{A_{Final}}/\hat{Y}_{B_{Final}}$) corresponding to the respective dataset ($X_A/X_B$). Further, the final set of predicted values ($\hat{Y}_{A_{Final}}/\hat{Y}_{B_{Final}}$) may be used by at least one of the client computing devices to identify one or more effective treatment compounds among the plurality of chemical compounds.

An additional example application includes a pharmaceutical diagnostic method. For example, in one embodiment, a first dimension of each of the plurality of datasets ($X_A/X_B$) transmitted to a managing computing device may include a plurality of patients and a second dimension of each of the plurality of datasets ($X_A/X_B$) may include descriptors of the patients (e.g., genomic-based descriptors, patient demographics, patient age, patient height, patient weight, or patient gender). In such an embodiment, entries in each of the plurality of datasets ($X_A/X_B$) may correspond to a binary indication of whether a respective patient exhibits a respective descriptor. Further, in such an embodiment, a first dimension of each of the sets of recorded values ($Y_A/Y_B$) respectively corresponding to the plurality of datasets ($X_A/X_B$) may include the plurality of patients and a second dimension of each of the sets of recorded values ($Y_A/Y_B$) may include clinical diagnoses of the patients (e.g., cancer diagnosis, heart disease diagnosis, broken bone diagnosis, skin infection diagnosis, psychological diagnosis, genetic disorder diagnosis, or torn ligament diagnosis). In such an embodiment, entries in each of the sets of recorded values ($Y_A/Y_B$) may correspond to a binary indication of whether a respective patient exhibits a respective clinical diagnosis.

The pharmaceutical diagnostic method may include the managing computing device 406 calculating a final shared representation ($U_{Final}$) of the datasets ($X_A/X_B$) based on the list of unique objects ($X_{Comb}$), the shared function (f), and the one or more shared parameters ($\beta$). The pharmaceutical diagnostic method may also include the managing computing device 406 transmitting the final shared representation ($U_{Final}$) of the datasets ($X_A/X_B$) to each of the client computing devices. The final shared representation ($U_{Final}$) of the datasets ($X_A/X_B$) may be usable by each of the client computing devices to determine a final set of predicted values ($\hat{Y}_{A_{Final}}/\hat{Y}_{B_{Final}}$) corresponding to the respective dataset ($X_A/X_B$). Further, the final set of predicted values ($\hat{Y}_{A_{Final}}/\hat{Y}_{B_{Final}}$) may be used by at least one of the client computing devices to diagnose at least one of the plurality of patients.

A further example application includes a media (e.g., book, movie, music, etc.) recommendation method. For example, in one embodiment, a first dimension of each of the plurality of datasets ($X_A/X_B$) transmitted to a managing computing device may include a plurality of users and a second dimension of each of the plurality of datasets ($X_A/X_B$) may include a plurality of book titles. In such an embodiment, entries in each of the plurality of datasets ($X_A/X_B$) may correspond to a rating of a respective book title by a respective user. Further, in such an embodiment, a first dimension of each of the sets of recorded values ($Y_A/Y_B$) respectively corresponding to the plurality of datasets ($X_A/X_B$) may include the plurality of users and a second dimension of each of the sets of recorded values ($Y_A/Y_B$) may include a plurality of movie titles. In such an embodiment, entries in each of the sets of recorded values ($Y_A/Y_B$) may correspond to a rating of a respective movie title by a respective user.

The media recommendation method may include the managing computing device 406 calculating a final shared representation ($U_{Final}$) of the datasets ($X_A/X_B$) based on the list of unique objects ($X_{Comb}$), the shared function (f), and the one or more shared parameters ($\beta$). The media recommendation method may also include the managing computing device 406 transmitting the final shared representation ($U_{Final}$) of the datasets ($X_A/X_B$) to each of the client computing devices. The final shared representation ($U_{Final}$) of the datasets ($X_A/X_B$) may be usable by each of the client computing devices to determine a final set of predicted values ($\hat{Y}_{A_{Final}}/\hat{Y}_{B_{Final}}$) corresponding to the respective dataset ($X_A/X_B$). Further, the final set of predicted values ($\hat{Y}_{A_{Final}}/\hat{Y}_{B_{Final}}$) may be used by at least one of the client computing devices to recommend at least one of the plurality of movie titles to at least one of the plurality of users.

Another example application includes an insurance policy determination method. For example, in one embodiment, a first dimension of each of the plurality of datasets ($X_A/X_B$) transmitted to a managing computing device may include a plurality of insurance policies and a second dimension of each of the plurality of datasets ($X_A/X_B$) may include a plurality of deductible amounts. In such an embodiment, entries in each of the plurality of datasets ($X_A/X_B$) may correspond to a binary indication of whether a respective insurance policy has a respective deductible amount. Further, in such an embodiment, a first dimension of each of the sets of recorded values ($Y_A/Y_B$) respectively corresponding to the plurality of datasets ($X_A/X_B$) may include the plurality of insurance policies and a second dimension of each of the sets of recorded values ($Y_A/Y_B$) may include a plurality of insurance premiums. In such an embodiment, entries in each of the sets of recorded values ($Y_A/Y_B$) may correspond to a binary indication of whether a respective insurance policy has a respective insurance premium.

The insurance policy determination method may include the managing computing device 406 calculating a final shared representation ($U_{Final}$) of the datasets ($X_A/X_B$) based on the list of unique objects ($X_{Comb}$), the shared function (f), and the one or more shared parameters ($\beta$). The insurance policy determination method may also include the managing computing device 406 transmitting the final shared representation ($U_{Final}$) of the datasets ($X_A/X_B$) to each of the client computing devices. The final shared representation ($U_{Final}$) of the datasets ($X_A/X_B$) may be usable by each of the client computing devices to determine a final set of predicted values ($\hat{Y}_{A_{Final}}/\hat{Y}_{B_{Final}}$) corresponding to the respective dataset ($X_A/X_B$). Further, the final set of predicted values ($\hat{Y}_{A_{Final}}/\hat{Y}_{B_{Final}}$) may be used by at least one of the client computing devices to recommend an insurance premium based on a prospective deductible amount.

Yet another example application includes an automotive fuel-efficiency-prediction method. For example, in one embodiment, a first dimension of each of the plurality of datasets ($X_A/X_B$) transmitted to a managing computing device may include a plurality of automobiles (e.g., identified by vehicle identification number (VIN) or serial number) and a second dimension of each of the plurality of datasets ($X_A/X_B$) may include a plurality of automobile parts. In such an embodiment, entries in each of the plurality of datasets ($X_A/X_B$) may correspond to a binary indication of whether a respective automobile has a respective automobile part equipped. Further, in such an embodiment, a first dimension of each of the sets of recorded values ($Y_A/Y_B$) respectively corresponding to the plurality of datasets ($X_A/X_B$) may include the plurality of automobiles and a second dimension of each of the sets of recorded values ($Y_A/Y_B$) may include a plurality of average fuel efficiencies. In such an embodiment, entries in each of the sets of recorded values ($Y_A/Y_B$) may correspond to a binary indication of whether a respective automobile has a respective average fuel efficiency.

The automotive fuel-efficiency-prediction method may include the managing computing device 406 calculating a final shared representation ($U_{Final}$) of the datasets ($X_A/X_B$) based on the list of unique objects ($X_{Comb}$), the shared function (f), and the one or more shared parameters ($\beta$). The automotive fuel-efficiency-prediction method may also include the managing computing device 406 transmitting the final shared representation ($U_{Final}$) of the datasets ($X_A/X_B$) to each of the client computing devices. The final shared representation ($U_{Final}$) of the datasets ($X_A/X_B$) may be usable by each of the client computing devices to determine a final set of predicted values ($\hat{Y}_{A_{Final}}/\hat{Y}_{B_{Final}}$) corresponding to the respective dataset ($X_A/X_B$). Further, the final set of predicted values ($\hat{Y}_{A_{Final}}/\hat{Y}_{B_{Final}}$) may be used by at least one of the client computing devices to predict an average fuel efficiency of an automobile model based on a set of equipped automobile parts.

In addition to those embodiments enumerated above, several other applications will be apparent. For example, various sets of datasets ($X_A/X_B$) and corresponding sets of recorded values ($Y_A/Y_B$) may be used to generate various machine-learned models, which could be used to perform various tasks (e.g., make recommendations and/or predictions). In various embodiments, such machine-learned models may be used to: make an attorney recommendation for a potential client based on various factors (e.g., competency of the attorney, specialty of the attorney, nature of client issue, timeline, cost, location of the client, location of the attorney, etc.), make a physician recommendation for a patient based on various factors (e.g., competency of the physician, specialty of the physician, nature of patient issue, timeline, cost, insurance, location of the physician, location of the patient, etc.), make a route recommendation or selection for navigation (e.g., for an autonomous vehicle) based on various factors (e.g., traffic data, automobile type, real-time weather data, construction data, etc.), make an air travel reservation and/or recommendation based on various factors (e.g., historical airline price data, weather data, calendar data, passenger preferences, airplane specifications, airport location, etc.), make a recommendation of a vacation destination based on various factors (e.g., prior travel locations of a traveler, traveler preferences, price data, weather data, calendar information for multiple travelers, ratings from prior travelers for a given destination, etc.), provide translations of text or speech from one language to another based on various factors (e.g., input accent detected, rate of speech, punctuation used, context of text, etc.), perform object recognition on one or more images in an image database based on various factors (e.g., size of the image and/or object, shape of the image and/or object, color(s) of the image and/or object, texture(s) of the image and/or object, saturation of the image and/or object, hue of the image and/or object, location of the object within the image, etc.), recommend an insurance premium, deductible, and/or coverage amount for automotive insurance, home insurance, life insurance, health insurance, dental insurance, boat insurance, malpractice insurance, and/or long term disability insurance based on various factors (e.g., age of the insured, health of the insured, gender of the insured, marital status of the insured, insurance premium amount, insurance deductible amount, insurance coverage amount, credit history, other demographic information about the insured, etc.), recommend an interest rate for home, automotive, and/or boat loan based on various factors (e.g., age of the home/automobile/boat, credit score of the borrower, down payment amount, repayment term, resale value of the home/automobile/boat, reliability statistics about homes/automobiles/boats, etc.), recommend a lender for an home, automotive, and/or boat loan based on various factors (e.g., credit score of the borrower, amount of the loan, repayment term of the loan, down payment amount on the loan, etc.), calculate a credit score for a creditor based on various factors (e.g., creditor age, creditor gender, creditor repayment history, creditor credit card ownership data, creditor average interest rate, amount creditor is in debt, etc.), grant or deny biometric access for a requester based on various factors (e.g., object recognition in a set of biometric images, fingerprint data, retinal data, requester height, requester gender, requester age, requester eye color, requester hair color, requester race, etc.), recommend a restaurant to a patron based on various factors (e.g., prior restaurants visited by the patron, cuisine preference data, weather data, calendar data, real-time restaurant wait-time data, ratings from prior patrons of various restaurants, restaurant location data, patron location data, etc.), or predict the outcome of a sporting event based on various data (e.g., record of prior sports contests involving the participants, current betting statistics for the sporting event, betting statistics for prior sporting events, weather data, location of the sporting event data, etc.), recommending a menu-item selection for a restaurant patron based on various factors (e.g., patron preferences, ratings of previous patrons, cuisine type data, alternative options on the menu, price, spice-level data, preparation-time data, etc.), determine viability and success of one or more genetic modifications to an organism with regards to curing a disease and/or palliate symptoms based on various factors (e.g., locus of genetic modification, probability of occurrence of genetic modification, complexity of the genome of the organism, side-effects of the genetic modification, number of mutations/splices required to create genetic modification, gender of organism with genetic modification, symptoms of organism with genetic modification, age of organism with genetic modification, etc.), determine how to allocate funding in a smart city according to various factors (e.g., amount of funds, traffic data, ages of buildings/infrastructure, population density data, hospital data, power supply demand data, criminal statistics, etc.), recommend an investment strategy based on various factors (e.g., investor income data, investor risk aversion data, stock market data, etc.), and/or recommend preventative maintenance be performed (e.g., on an automobile, boat, industrial machine, factory equipment, airplane, infrastructure, etc.) based on various factors (e.g., age of the object, money invested into the object, statistical data regarding similar objects, year when the object was built, object use data, weather data, last preventative maintenance performed, cost of maintenance, etc.).

Any of the "various factors" provided as examples above could be components of datasets (e.g., one or more dimensions of a dataset). Similarly, corresponding "outcomes" (e.g., the recommended attorney or recommended physician) could be components of sets of predicted values ($\hat{Y}_A/\hat{Y}_B$) (e.g., one or more dimension of a set of predicted values) and/or sets of recorded values ($Y_A/Y_B$) (e.g., one or more dimension of a set of recorded values).

Figure 17B:
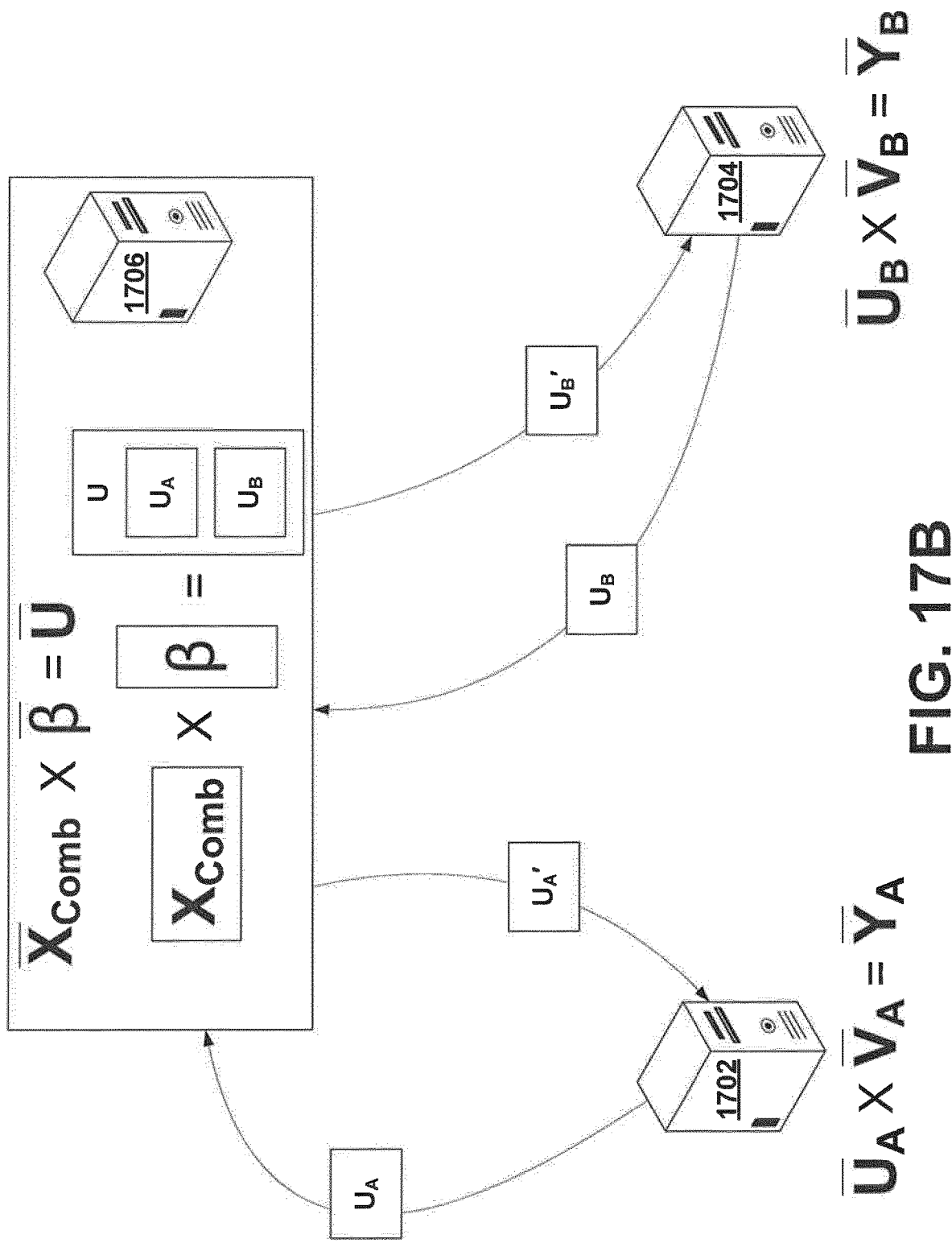
FIG. 17B illustrates a matrix factorization algorithm, according to example embodiments.
Figure 20:
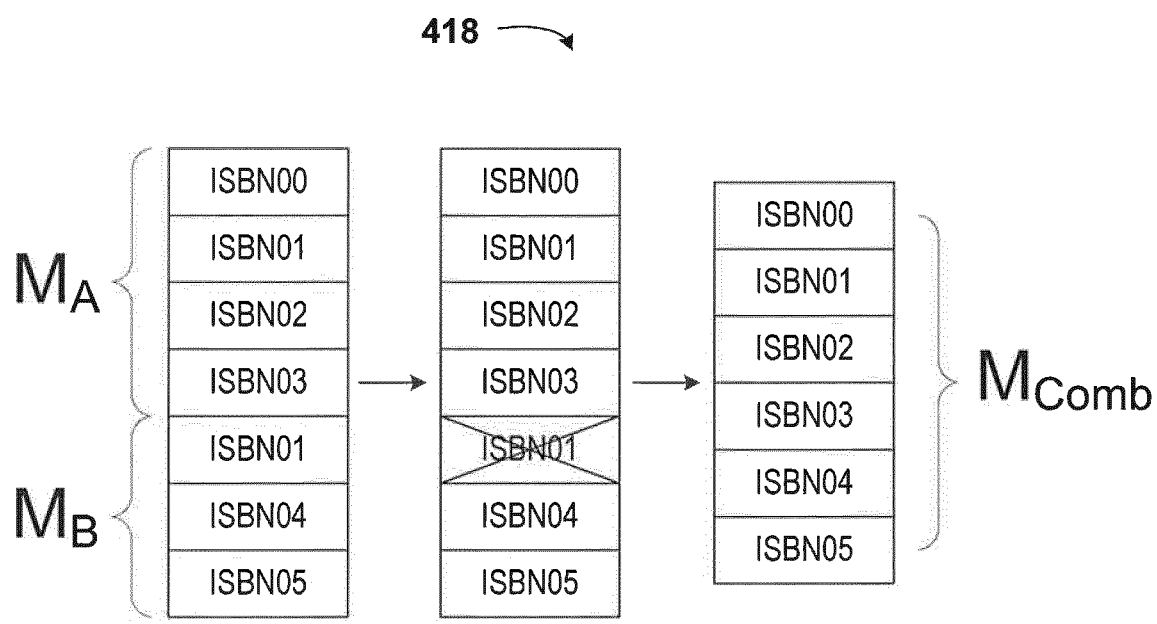
FIG. 20 illustrates a composite list of identifiers, according to example embodiments.
Figure 21:
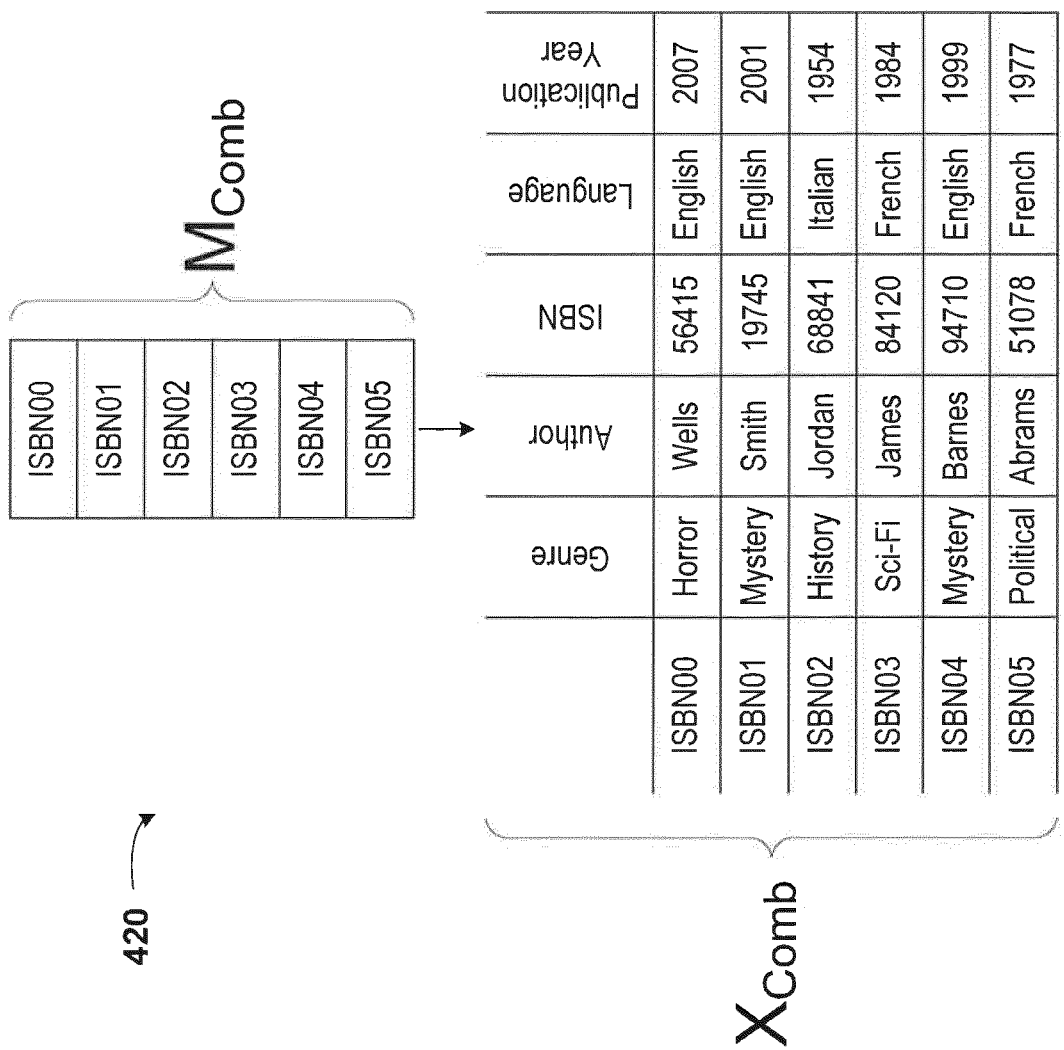
FIG. 21 illustrates a list of unique objects, according to example embodiments.
Figure 22:
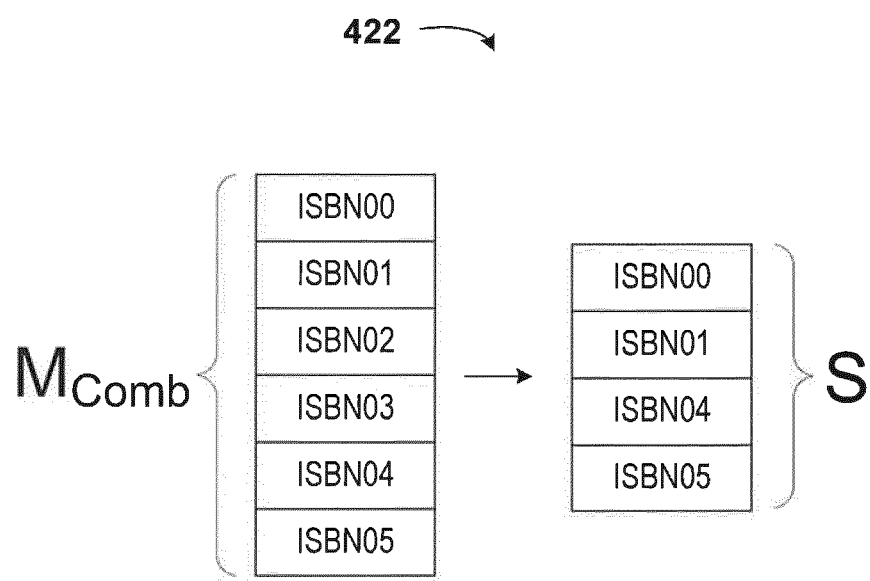
FIG. 22 illustrates a subset of identifiers, according to example embodiments.
Figure 23:
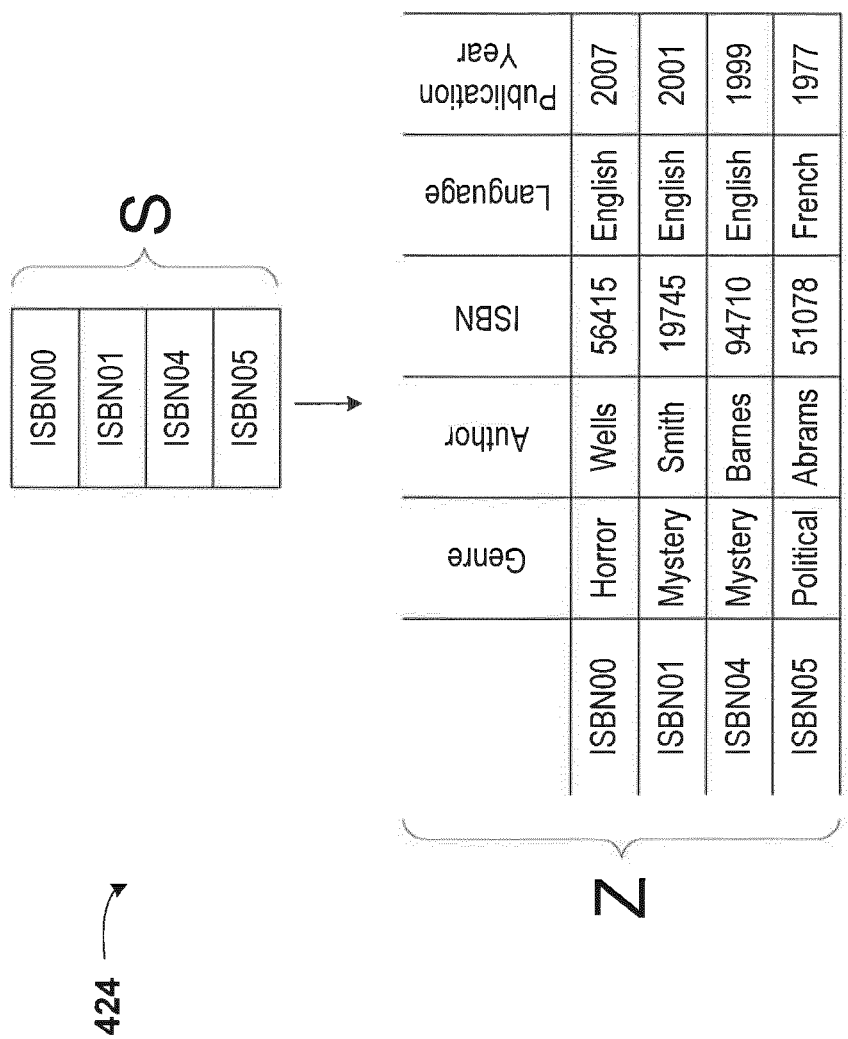
FIG. 23 illustrates a subset of the list of unique objects, according to example embodiments.
Figure 24:
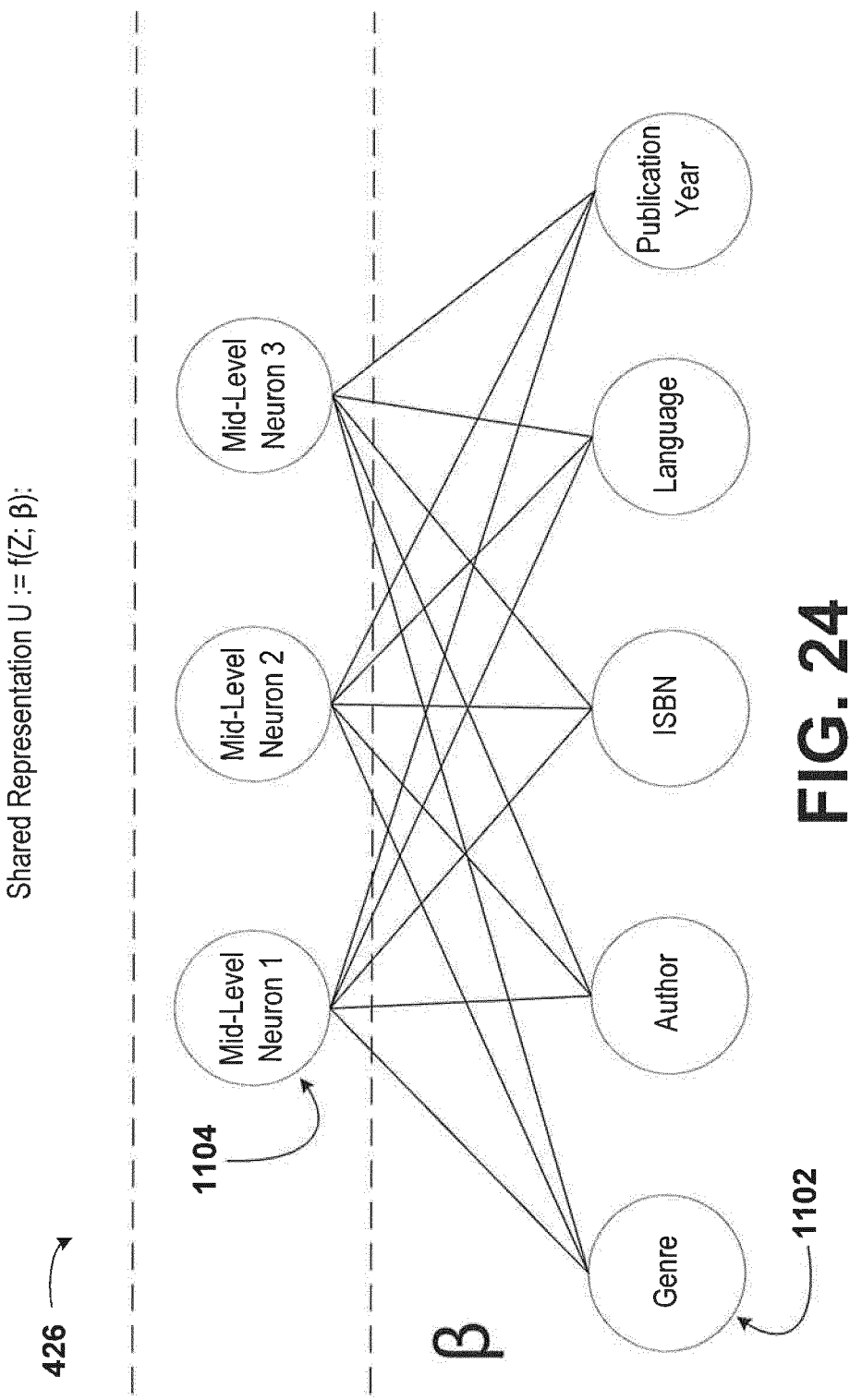
FIG. 24 illustrates a shared representation, according to example embodiments.
Figure 25A:
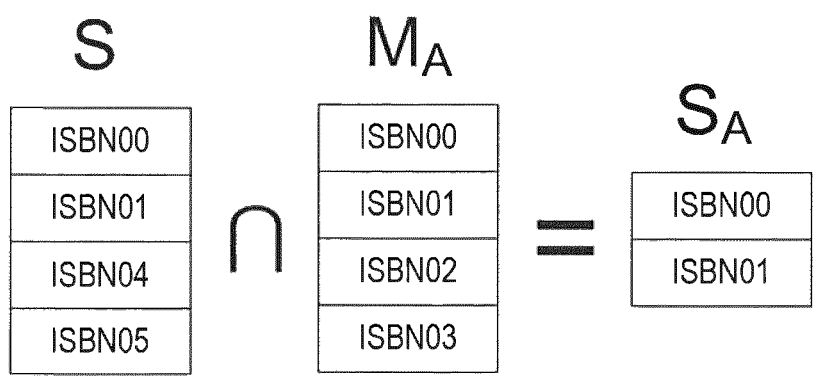
FIG. 25A illustrates a sublist of objects for a dataset, according to example embodiments.
Figure 25B:
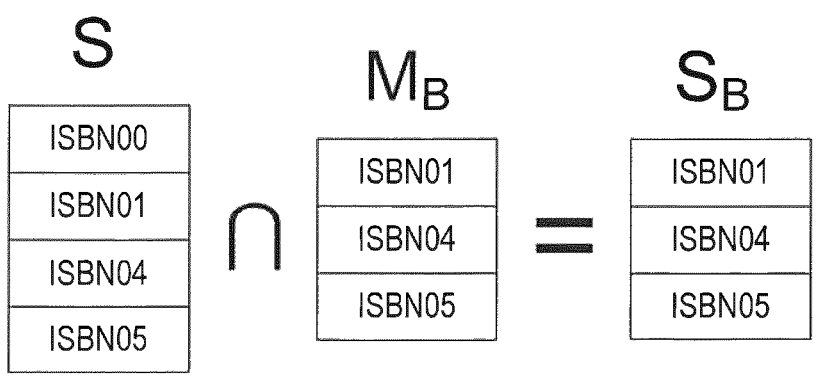
FIG. 25B illustrates a sublist of objects for a dataset, according to example embodiments.
Figure 26A:
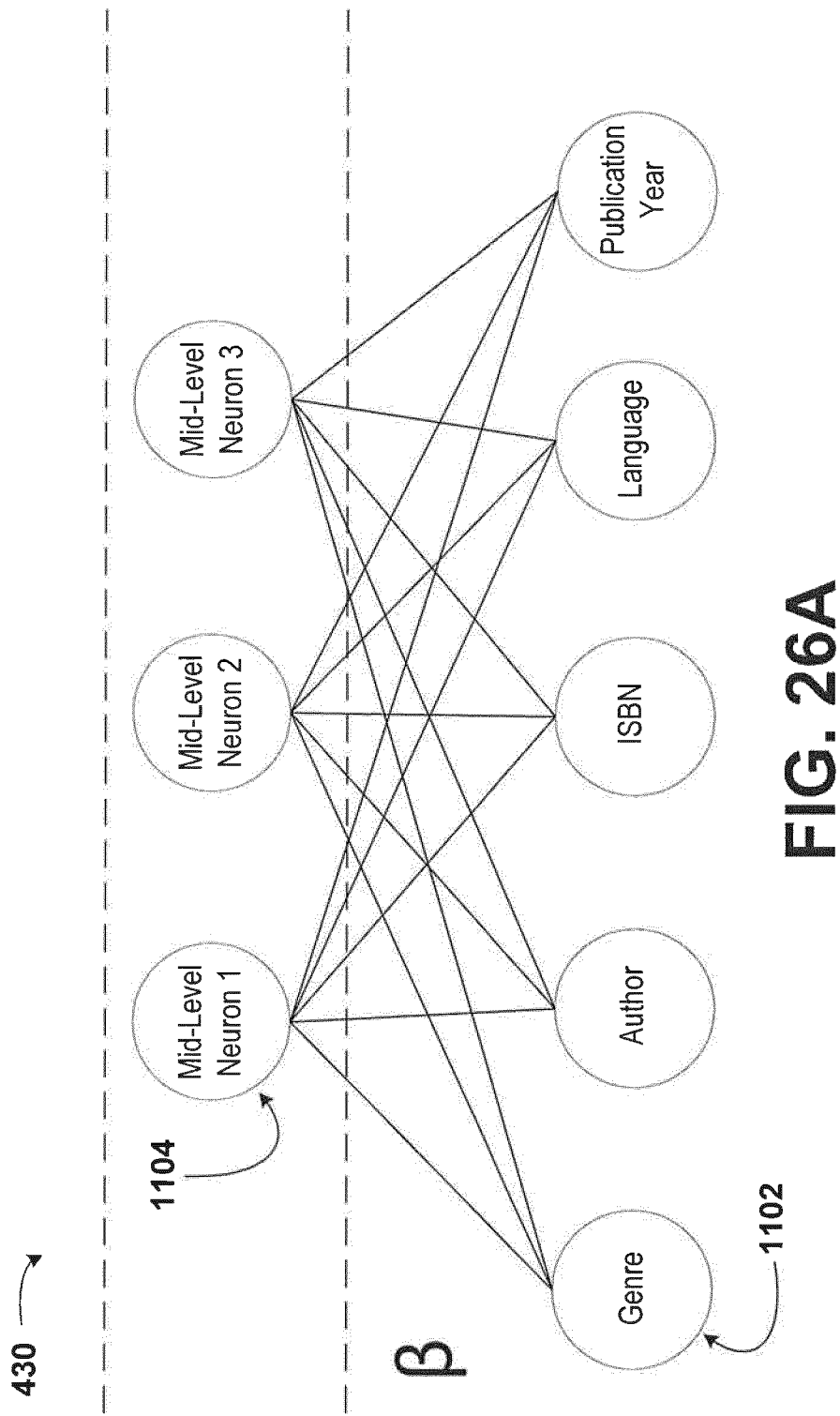
FIG. 26A illustrates a partial representation, according to example embodiments.
Figure 26B:
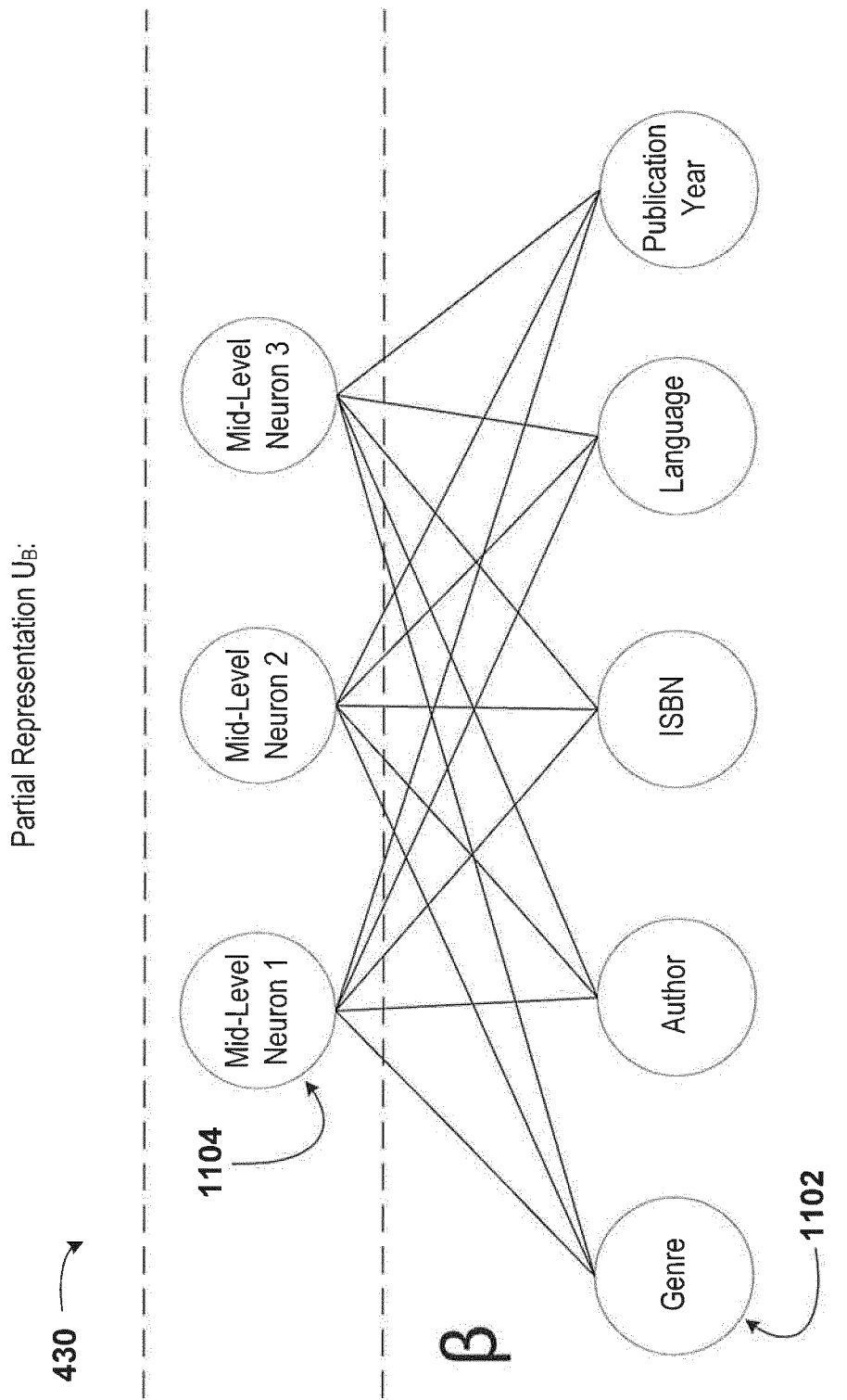
FIG. 26B illustrates a partial representation, according to example embodiments.

FIGS. 17A and 17B illustrate a matrix factorization algorithm (e.g., using a Macau factorization method), according to example embodiments. The matrix factorization method, similar to the methods described above, may be used to generate a machine-learned model while still preserving privacy of individual party's data. The matrix factorization algorithm may be performed using similar operations to those described with reference to FIGS. 4B-4E, for example. The matrix factorization algorithm illustrated is provided as an example of one embodiment of a myriad of embodiments contemplated herein that do not necessarily incorporate an artificial neural network model. In alternate embodiments, however, performing the matrix factorization illustrated in FIGS. 17A and 17B may include developing an artificial neural network model, in tandem with factoring the matrices. Similarly, in still other embodiments, other machine learning models/methods may be used in conjunction with the illustrated matrix factorization.

As illustrated in FIG. 17A, the recorded value tensor $\overline{Y}$ may be factored into matrices $\overline{U}$ and $\overline{V}$. In other words, Y may be equal to $\overline{U} \times \overline{V}$. The recorded value tensor $\overline{Y}$ may contain the set of recorded values corresponding to a respective dataset. For example, the recorded value tensor $\overline{Y}_A$ may correspond to dataset A ($X_A$). In such embodiments, a tensor ($\overline{X}_A$) representing dataset A ($X_A$) may be multiplied by a shared parameter tensor ($\overline{\beta}$) (e.g., a one-dimensional shared parameter tensor, called a shared parameter vector) corresponding to one or more shared parameters ($\beta$) in order to form one of the factored matrices ($\overline{U}_A$) relating to dataset A ($X_A$). In other words, $\overline{U}_A$ may be equal to $\overline{X}_A \times \overline{\beta}$. In this way, the shared parameter tensor ($\overline{\beta}$) can be used to encode side information about objects in dataset A ($X_A$). For example, in embodiments where dataset A ($X_A$) represents ratings for a plurality of movies, the shared parameter tensor ($\overline{\beta}$) may represent information describing genres (e.g., horror, comedy, romance, etc.) of the plurality of movies. Such side information can improve the machine learning model generated (e.g., by assuming a viewer who gives a first movie in the "horror" genre a high rating may be more likely to give a second movie in the "horror" genre a high rating than a user who gave the first movie in the "horror" genre a low rating). In some embodiments (e.g., embodiments where the recorded value tensor $\overline{Y}_A$ has three or more dimensions), there may be multiple corresponding tensors (e.g., a number of matrices corresponding to the rank of the recorded value tensor $\overline{Y}_A$) multiplied together to result in the recorded value tensor $\overline{Y}_A$.

Similar to the embodiments described above (with reference to FIGS. 4B-15B), the tensor ($\overline{U}_A$) may correspond to a partial representation ($U_A$) that is part of a shared representation (U). The shared representation (U) may be based on all of the datasets transmitted and received by a managing computing device 1706, as illustrated in FIG. 17B. For example, the managing computing device 1706 may originally receive dataset A ($X_A$) from client computing device A 1702 and dataset B ($X_B$) from client computing B 1704. Upon receiving dataset A ($X_A$) and dataset B ($X_B$) the managing computing device 1706 may then create a list of unique objects ($X_{Comb}$) (e.g., using a process similar to that described above with respect to FIGS. 4B-4E).

Upon creating the list of unique objects ($X_{Comb}$), the managing computing device may determine a shared representation (U) based on one or more shared parameters (β). In some embodiments, the one or more shared parameters may be randomly instantiated, prior to updating. This may happen according to the equation $\overline{X}_{Comb} \times \overline{\beta} = \overline{U}$, as illustrated in FIG. 17B. The shared representation (U) may then be transmitted to each of the client computing devices 1702/1704 by the managing computing device 1706. Then, each client computing device may determine which portion of the shared representation (U) corresponds to the dataset corresponding to the respective client computing device (e.g., based on a subset of identifiers (S) and a list of identifiers ($M_A/M_B$) for a respective dataset corresponding to the respective client computing device). This determined portion may represent the respective partial representation ($U_A/U_B$).

In some embodiments, a method may then be employed to update/refine the one or more shared parameters (β). The method may include client computing device A 1702 using the determined partial representation ($U_A$) to calculate a set of predicted values ($\widetilde{Y}_A$). The set of predicted values may be calculated by $\overline{U}_A^\circ = \overline{V}_A^\circ = \widetilde{Y}_A^\circ$ (where 'o' denotes that this is the initial iteration). In some embodiments, the original value for the other factored tensor ($\overline{V}_A^\circ$) may be instantiated randomly. Upon calculating a set of predicted values ($\widetilde{Y}_A^\circ$) (e.g., referred to as a predicted value tensor), the partial representation tensor ($\overline{U}_A^\circ$) and the other factored tensor ($\overline{V}_A^\circ$) may be updated (e.g., to a second iteration, indicated by '1' rather than 'o') by factoring the set of predicted values ($\widetilde{Y}_A^\circ$). Using the updated partial representation tensor ($\overline{U}_A^1$), the shared parameter tensor ($\overline{\beta}$) may then be updated by solving $\overline{X}_A \times \overline{\beta} = \overline{U}_A^1$ for $\overline{\beta}$ (or, in some embodiments, at least solving for the regions of the shared parameter tensor $\overline{\beta}$ that correspond to non-zero entries in the tensor ($\overline{X}_A$) representing dataset A ($X_A$)). After updating the shared parameter tensor ($\overline{\beta}$), the partial representation tensor ($\overline{U}_A^1$) may then be transmitted to the managing computing device 1706. The above-described operations of updating the partial representation tensor and the shared parameter tensor, and the transmission of the partial representation tensor to the managing computing device 1706, may be performed by multiple client computing devices (e.g., both client computing device A 1702 and client computing device B 1704) for their respective datasets (e.g., dataset A ($X_A$) and dataset B ($X_B$)).

Upon receiving the updated partial representation matrices ($\overline{U}_A^1/\overline{U}_B^1$), the managing computing device may recombine them into a shared representation tensor ($\overline{U}^1$). Using the shared representation tensor, a shared parameter tensor ($\overline{\beta}$) may be updated using the list of unique objects ($X_{Comb}$) by solving the following equation: $\overline{X}_{Comb} \times \overline{\beta} = \overline{U}^1$, as illustrated in FIG. 17B.

Thereafter, the updated shared representation tensor ($\overline{U}^1$) may then be transmitted to each of the client computing devices 1702/1704 by the managing computing device 1706. Then, each client computing device may determine which portion of the updated shared representation tensor ($\overline{U}^1$) corresponds to the dataset corresponding to the respective client computing device (e.g., based on a subset of identifiers (S) and a list of identifiers ($M_A/M_B$) for a respective dataset corresponding to the respective client computing device). This determined portion may represent the respective partial representation ($U_A/U_B$). Based on this partial representation ($U_A/U_B$), an second iteration of a set of predicted values ($\widetilde{Y}_A^1$) may be calculated, a second partial representation tensor ($\overline{U}_A^1$) and the other factored tensor ($\overline{V}_A^1$) may be updated (e.g., to a third iteration) by factoring the second iteration of the set of predicted values ($\widetilde{Y}_A^1$) (e.g., using Macau factorization), and the shared parameter tensor ($\overline{\beta}$) may be updated by solving $X_A \times \overline{\beta} = \overline{U}_A^2$ for $\overline{\beta}$. The steps of the previous paragraphs may be repeated until the shared parameter tensor ($\overline{\beta}$) stop improving after an iteration or stop improving at least a threshold amount per iteration.

FIGS. 18A-27B illustrate an alternative embodiment of the method 400 illustrated in FIGS. 4B-4F. For example, FIGS. 18A-27B may be respectively analogous to FIGS. 5A-14B. However, as illustrated in FIGS. 18A and 18B, dataset A ($X_A$), the set of recorded values ($Y_A$) corresponding to dataset A ($X_A$), dataset B ($X_B$), and the set of recorded values ($Y_B$) corresponding to dataset B ($X_B$) may include different data than is included in the example embodiments of FIGS. 5A-14B.

As illustrated in FIG. 18A, dataset A ($X_A$) may include four objects in a first dimension (e.g., "Book Title 1," "Book Title 2," "Book Title 3," and "Book Title 4"). These objects may correspond to books that are stocked and/or sold from a bookseller (e.g., an online bookseller or a bookstore). Such a bookseller may correspond to client computing device A 402, for example. In a second dimension of dataset A ($X_A$), there may be five features corresponding to each of the four objects (e.g., "Genre," "Author," "ISBN," "Language," and "Publication Year"). The entries corresponding to each pair of (object, feature) may correspond to a value of a given feature for a given object. For example, object "Book Title 1" may have a value for feature "ISBN" of "56415." While values corresponding to "ISBN" are illustrated using 5 digits, other numbers of digits may be used in example embodiments (e.g., 10 digits, 13 digits, 20 digits, etc.). Further, in some embodiments, ISBN may be a binary number or a hexadecimal number (e.g., rather than a decimal number).

Further, as illustrated in FIG. 18A, the corresponding set of recorded values ($Y_A$) includes the same four objects in a first dimension (e.g., "Book Title 1," "Book Title 2," "Book Title 3," and "Book Title 4") as the four objects in dataset A ($X_A$). The set of recorded values ($Y_A$) may also correspond to the bookseller that corresponds to dataset A ($X_A$). In a second dimension of the corresponding set of recorded values ($Y_A$), there may be five features corresponding to each of the four objects (e.g., "Timmy," "Johnny," "Sally," "Sue," and "Mark"). The entries corresponding to each pair of (object, feature) in the corresponding set of recorded values ($Y_A$) may correspond to a rating value (e.g., ranging from 0-100). For example, feature "Johnny" may have rated object "Book Title 2" with a value of "18."

Similarly, as illustrated in FIG. 18B, dataset B ($X_B$) may include three objects in a first dimension (e.g., "Book Title 2," "Book Title 5," and "Book Title 6"). These objects may correspond to books that are stocked and/or sold from a bookseller (e.g., an online bookseller or a bookstore that is different from the online bookseller or bookstore corresponding to dataset A ($X_A$)). Such a bookseller may correspond to client computing device B 404, for example. In a second dimension of dataset B ($X_B$), there may be five features corresponding to each of the three objects (e.g., "Genre," "Author," "ISBN," "Language," and "Publication Year"). As illustrated, the features of dataset B ($X_B$) may be the same as the features of dataset A ($X_A$). The entries corresponding to each pair of (object, feature) may correspond to a value of a given feature for a given object. For example, object "Book Title 5," may have a value for feature "Language" of "English."

Further, as illustrated in FIG. 18B, the corresponding set of recorded values ($Y_B$) includes the same three objects in a first dimension (e.g., "Book Title 2," "Book Title 5," and "Book Title 6") as the three objects in dataset B ($X_B$). The set of recorded values ($Y_B$) may also correspond to the bookseller that corresponds to dataset B ($X_B$). In a second dimension of the corresponding set of recorded values ($Y_B$), there may be three features corresponding to each of the three objects (e.g., "Bob," "Margarette," and "Bram"). The entries corresponding to each pair of (object, feature) in the corresponding set of recorded values ($Y_B$) may correspond to a rating value (e.g., ranging from 0-100). For example, feature "Bram" may have rated object "Book Title 6" with a value of "74."

As illustrated in FIGS. 19A-23, ISBNs may be used by the managing computing device 406 as identifiers for each of the objects in dataset A ($X_A$) and dataset B ($X_B$).

Figure 27A:
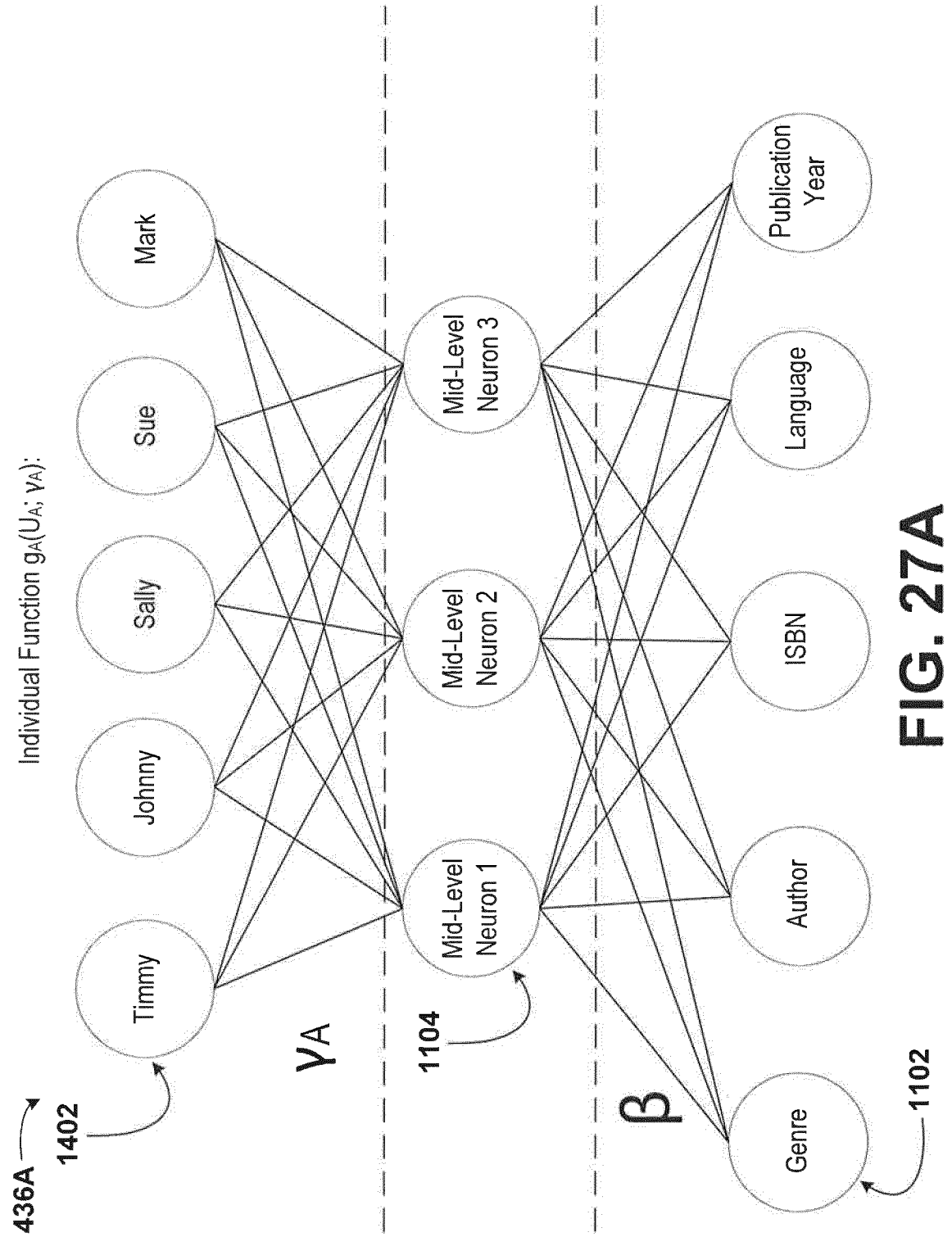
FIG. 27A illustrates an individual function, according to example embodiments.
Figure 27B:
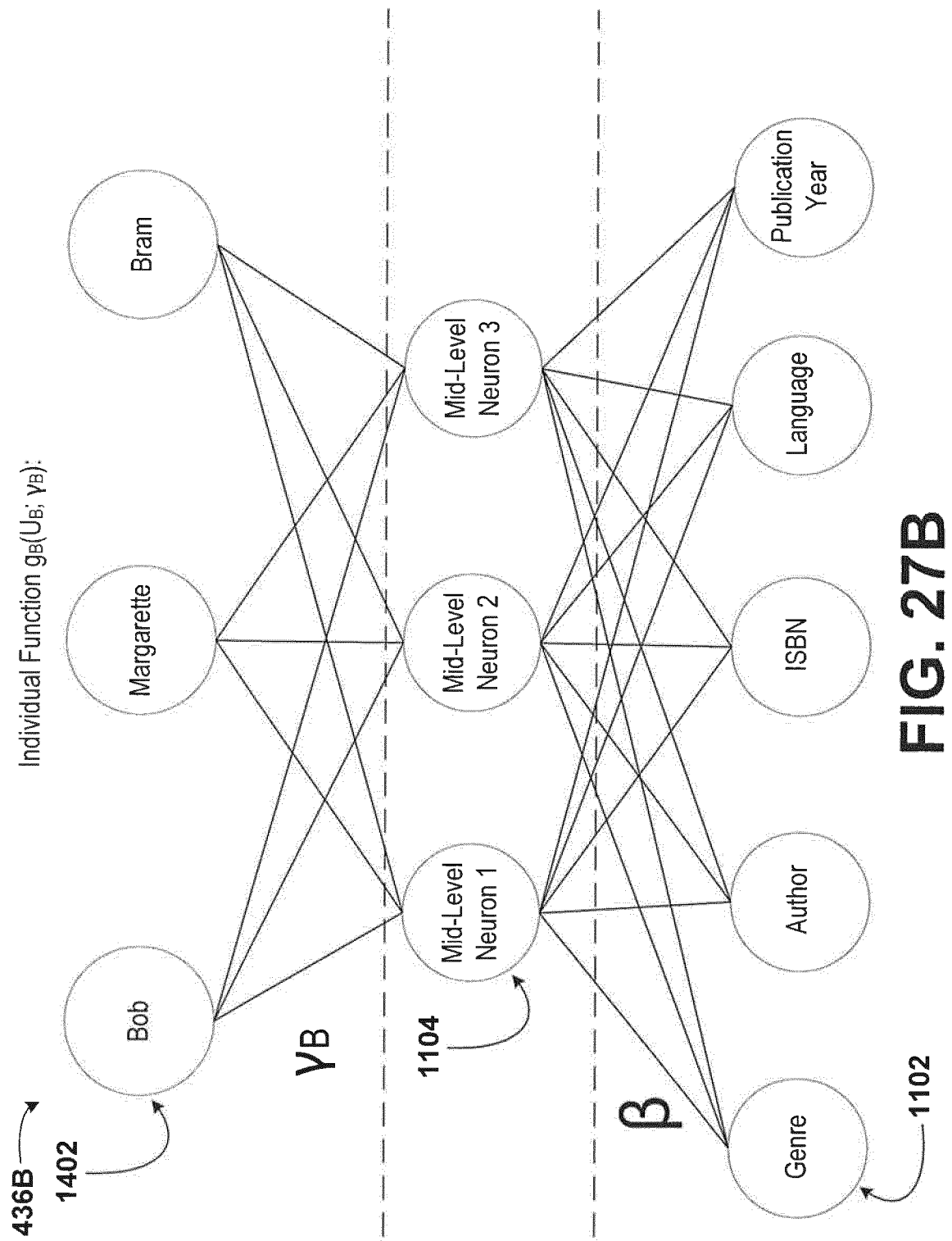
FIG. 27B illustrates an individual function, according to example embodiments.

Propagating through the operations of the method 400 illustrated in FIGS. 4B-4E (e.g., as illustrated in FIGS. 19A-27B), sets of predicted values ($\hat{Y}_A/\hat{Y}_B$) can be determined for a respective partial representation ($U_A/U_B$) by each client computing device, as illustrated in FIGS. 27A and 27B. Using the sets of predicted values ($\hat{Y}_A/\hat{Y}_B$) and the corresponding sets of recorded values ($Y_A/Y_B$), the client computing devices may determine errors ($E_A/E_B$) (e.g., based on individual loss functions ($L_A/L_B$)). Based on these errors, the client computing devices may determine and transmit respective feedback values ($C_A/C_B$) to the managing computing device 406. Using the respective feedback values ($C_A/C_B$), the managing computing device 406 may update the shared representation (U).

If the shared representation (U) and/or the one or more shared parameters (β) are distributed to the client computing devices, the client computing devices may use the shared representation (U) and/or the one or more shared parameters (β) to make future predictions. For example, if a bookseller corresponding to client computing device A 402 and dataset A ($X_A$) offers a new book for sale, that bookseller may predict the ratings that pre-existing customers will give to the new book (e.g., based on the new book's values corresponding to the features of "Genre," "Author," "ISBN," "Language," and/or "Publication Year").

In another example embodiment, the objects within the datasets ($X_A/X_B$) may be chemical compounds (e.g., in FIGS. 18A and 18B, "Book Title 1," "Book Title 2," etc. may be replaced with "Chemical Compound 1," "Chemical Compound 2," etc.). In such embodiments, the identifiers used for the chemical compounds may be a chemical fingerprint (e.g., analogously to ISBNs as illustrated in FIGS. 19A-23). Further, in such embodiments, features of the corresponding sets of recorded values ($Y_A/Y_B$) may correspond to cellular targets (e.g., cancer cells, gametes, etc.), rather than users (e.g., "Timmy," "Johnny," etc. may be replaced with "Cancer Cells," "Gametes," etc.). Still further in such embodiments, features of the datasets ($X_A/X_B$) such as "Genre" and "Author" may be replaced with features regarding chemical side information (e.g., such as certain functional groups that may be comprise a portion of a chemical compound, such as a hydroxyl group).

IV. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, operation, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step, block, or operation that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer-readable medium such as a storage device including RAM, a disk drive, a solid state drive, or another storage medium.

The computer-readable medium can also include non-transitory computer-readable media such as computer-readable media that store data for short periods of time like register memory and processor cache. The computer-readable media can further include non-transitory computer-readable media that store program code and/or data for longer periods of time. Thus, the computer-readable media may include secondary or persistent long term storage, like ROM, optical or magnetic disks, solid state drives, compact-disc read only memory (CD-ROM), for example. The computer-readable media can also be any other volatile or non-volatile storage systems. A computer-readable medium can be considered a computer-readable storage medium, for example, or a tangible storage device.

Moreover, a step, block, or operation that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

Embodiments of the present disclosure may thus relate to one of the enumerated example embodiments (EEEs) listed below.

EEE 1 is a method, comprising:
receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers; computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
the sublist of objects for the respective dataset; and
the partial representation for the respective dataset;
receiving, by the managing computing device, one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;
determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
updating, by the respective client computing device, the one or more individual parameters for the respective dataset; and
determining, by the respective client computing device, the one or more feedback values, wherein the one or more feedback values are used to determine a change in the partial representation that corresponds to an improvement in the set of predicted values;
determining, by the managing computing device, based on the sublists of objects and the one or more feedback values from the client computing devices, one or more aggregated feedback values; and
updating, by the managing computing device, the one or more shared parameters based on the one or more aggregated feedback values.

EEE 2 is the method of EEE 1, further comprising transmitting, by the managing computing device, the shared function and the one or more shared parameters to each of the client computing devices.

EEE 3 is the method of EEEs 1 or 2, wherein each identifier of the subset of identifiers is selected randomly or pseudo-randomly.

EEE 4 is the method of EEE 3, wherein each identifier of the subset of identifiers is selected based on a Mersenne Twister pseudo-random number generator.

EEE 5 is the method of EEEs 1 or 2, wherein each identifier of the subset of identifiers is selected according to an algorithm known only to the managing computing device.

EEE 6 is the method of EEEs 1 or 2, wherein each identifier of the subset of identifiers is selected according to a publicly available algorithm.

EEE 7 is the method of any of EEEs 1-6, wherein determining, by the managing computing device, the list of unique objects from among the plurality of datasets comprises:
creating, by the managing computing device, a composite list of objects that is a combination of the objects from each dataset; and
removing, by the managing computing device, duplicate objects from the composite list of objects based on an intersection of the lists of identifiers for each of the plurality of datasets.

EEE 8 is the method of any of EEEs 1-7, wherein the individual loss function comprises at least one of: a quadratic loss function, a logarithmic loss function, a hinge loss function, or a quantile loss function.

EEE 9 is the method of any of EEEs 1-8, wherein determining the error for the respective dataset comprises:
identifying, by the respective client computing device, which of the non-empty entries in the set of recorded values corresponding to the respective dataset corresponds to an object in the sublist of objects;
determining, by the respective client computing device, a partial error value for each of the identified non-empty entries in the set of recorded values corresponding to the respective dataset by applying the individual loss function between each identified non-empty entry and its corresponding predicted value in the set of predicted values corresponding to the respective dataset; and
combining, by the respective client computing device, the partial error values.

EEE 10 is the method of any of EEEs 1-9, further comprising:
  calculating, by the managing computing device, a final shared representation of the datasets based on the list of unique objects, the shared function, and the one or more shared parameters; and
  transmitting, by the managing computing device, the final shared representation of the datasets to each of the client computing devices.

EEE 11 is the method of EEE 10, wherein the final shared representation of the datasets is usable by each of the client computing devices to determine a final set of predicted values corresponding to the respective dataset.

EEE 12 is the method of EEE 11, wherein determining the final set of predicted values corresponding to the respective dataset comprises:
  receiving, by the respective client computing device, the sublist of objects for the respective dataset;
  determining, by the respective client computing device, a final partial representation for the respective dataset based on the sublist of objects and the final shared representation; and
  determining, by the respective client computing device, the final set of predicted values corresponding to the respective dataset based on the final partial representation, the individual function, and the one or more individual parameters corresponding to the respective dataset.

EEE 13 is the method of EEEs 11 or 12, wherein the final set of predicted values is:
  displayed by at least one of the client computing devices; or
  used by at least one of the client computing devices to provide one or more predictions about objects in the dataset corresponding to the respective client computing device.

EEE 14 is the method of any of EEEs 1-13, wherein the one or more feedback values from each of the client computing devices are based on back-propagated errors.

EEE 15 is the method of any of EEEs 1-14,
  wherein the shared function corresponds to one or more first layers of an artificial neural network model,
  wherein each individual function corresponds to at least a portion of one or more second layers of the artificial neural network model, and
  wherein at least one of the one or more first layers is an input layer to at least one of the one or more second layers.

EEE 16 is the method of EEE 15, wherein the one or more shared parameters each corresponds to one or more weights in a weight tensor of the shared representation.

EEE 17 is the method of EEEs 15 or 16, wherein the one or more individual parameters each corresponds to one or more weights in a weight tensor of the individual function for the respective dataset.

EEE 18 is the method of any of EEEs 1-17, wherein each of the plurality of datasets comprises an equal number of dimensions.

EEE 19 is the method of EEE 18, wherein the number of dimensions is two, three, four, five, six, seven, eight, nine, ten, sixteen, thirty-two, sixty-four, one-hundred and twenty-eight, two-hundred and fifty-six, five-hundred and twelve, or one-thousand and twenty-four.

EEE 20 is the method of any of EEEs 1-19,
  wherein each of the plurality of datasets is represented by a tensor, and
  wherein at least one of the plurality of datasets is represented by a sparse tensor.

EEE 21 is the method of any of EEEs 1-20, wherein the shared function comprises an artificial neural network having rectified linear unit (ReLU) non-linearity and dropout.

EEE 22 is the method of any of EEEs 1-21, wherein determining, by the respective client computing device, the one or more feedback values corresponds to performing, by the respective client computing device, a gradient descent method.

EEE 23 is the method of any of EEEs 1-22, wherein the improvement in the set of predicted values corresponds to a threshold improvement value based on a shared learning rate.

EEE 24 is the method of EEE 23, further comprising:
  determining, by the managing computing device, the shared learning rate for the client computing devices; and
  transmitting, by the managing computing device, the shared learning rate to each of the client computing devices.

EEE 25 is the method of EEE 23,
  wherein determining, by the respective client computing device, the one or more feedback values corresponds to performing, by the respective client computing device, a gradient descent method, and
  wherein the shared learning rate is defined by the gradient descent method.

EEE 26 is the method of any of EEEs 23-25, wherein the shared learning rate comprises at least one of: an exponentially decayed learning rate, a harmonically decayed learning rate, or a step-wise exponentially decayed learning rate.

EEE 27 is the method of any of EEEs 1-22, wherein improvement in the set of predicted values corresponds to a threshold improvement value defined by an individual learning rate that is determined by each of the client computing devices independently.

EEE 28 is the method of EEE 27, wherein the individual learning rate comprises at least one of: an exponentially decayed learning rate, a harmonically decayed learning rate, or a step-wise exponentially decayed learning rate.

EEE 29 is the method of any of EEEs 1-28, further comprising:
  selecting, by the managing computing device, an additional subset of identifiers from the composite list of identifiers;
  determining, by the managing computing device, an additional subset of the list of unique objects corresponding to each identifier in the additional subset of identifiers;
  computing, by the managing computing device, a revised shared representation of the datasets based on the additional subset of the list of unique objects and the shared function having the one or more shared parameters;
  determining, by the managing computing device, additional sublists of objects for the respective dataset of each client computing device based on an intersection of the additional subset of identifiers with the list of identifiers for the respective dataset;
  determining, by the managing computing device, a revised partial respective for the respective dataset of each client computing device based on the additional sublist of objects for the respective dataset and the revised shared representation;

transmitting, by the managing computing device, to each of the client computing devices:
  the additional sublist of objects for the respective dataset; and
  the revised partial representation for the respective dataset;
receiving, by the managing computing device, one or more revised feedback values from at least one of the client computing devices, wherein the one or more revised feedback values are determined by the client computing devices by:
  determining, by the respective client computing device, a revised set of predicted values corresponding to the respective dataset, wherein the revised set of predicted values is based on the revised partial representation and the individual function with the one or more individual parameters corresponding to the respective dataset;
  determining, by the respective client computing device, a revised error for the respective dataset based on the individual loss function for the respective dataset, the revised set of predicted values corresponding to the respective dataset, the additional sublist of objects, and the non-empty entries in the set of recorded values corresponding to the respective dataset;
  updating, by the respective client computing device, the one or more individual parameters for the respective dataset; and
  determining, by the respective client computing device, the one or more revised feedback values, wherein the one or more revised feedback values are used to determine a change in the revised partial representation that corresponds to an improvement in the set of predicted values;
determining, by the managing computing device, based on the additional sublists of objects and the one or more revised feedback values, one or more revised aggregated feedback values;
updating, by the managing computing device, the one or more shared parameters based on the one or more revised aggregated feedback values; and
determining, by the managing computing device based on the one or more revised aggregated feedback values, that an aggregated error corresponding to the revised errors for all respective datasets has been minimized.

EEE 30 is the method of any of EEEs 1-29,
  wherein the one or more feedback values from the client computing devices are organized into feedback tensors, and
  wherein each respective feedback tensor has a dimensionality that is equal to a dimensionality of the respective partial representation.

EEE 31 is the method of any of EEEs 1-30,
  wherein the one or more aggregated feedback values are organized into an aggregated feedback tensor, and
  wherein the aggregated feedback tensor has a dimensionality that is equal to a dimensionality of the shared representation.

EEE 32 is the method of any of EEEs 1-31, further comprising initializing, by the managing computing device, the shared function and the one or more shared parameters based on a related shared function used to model a similar relationship.

EEE 33 is the method of any of EEEs 1-31, further comprising:
  receiving, by the managing computing device, initial values for the one or more shared parameters from a first client computing device of the plurality of client computing devices; and
  initializing, by the managing computing device, the shared function and the one or more shared parameters based on the initial values for the one or more shared parameters.

EEE 34 is the method of EEE 33, wherein the initial values for the one or more shared parameters are determined by the first client computing device based upon one or more public models.

EEE 35 is the method of any of EEEs 1-31, further comprising initializing, by the managing computing device, the shared function and the one or more shared parameters based on at least one of: a random number generator or a pseudo-random number generator.

EEE 36 is the method of any of EEEs 1-35, wherein determining the one or more feedback values by the client computing devices further comprises initializing, by the respective client computing device, the individual function and the one or more individual parameters corresponding to the respective data set based on a random number generator or a pseudo-random number generator.

EEE 37 is the method of any of EEEs 1-36, wherein determining, based on the sublists of objects and the one or more feedback values from the client computing devices, the one or more aggregated feedback values comprises:
  defining, by the managing computing device, based on the sublists of objects and the one or more feedback values from the client computing devices, a tensor representing the one or more aggregated feedback values; and
  summing, by the managing computing device based on the sublists of objects, those feedback values of the one or more feedback values from the client computing devices that correspond to objects in the sublists of objects that have shared identifiers into a shared entry of the tensor representing the one or more aggregated feedback values.

EEE 38 is the method of any of EEEs 1-37,
  wherein updating the one or more shared parameters based on the one or more aggregated feedback values comprises evaluating a sum of partial derivatives, and
  wherein each of the partial derivatives are partial derivatives of the error for a respective dataset with respect to the one or more shared parameters.

EEE 39 is the method of any of EEEs 1-37,
  wherein updating the one or more shared parameters based on the one or more aggregated feedback values comprises evaluating a sum of products of first partial derivatives and second partial derivatives,
  wherein the first partial derivatives are partial derivatives of the error for a respective dataset with respect to the respective partial representation, and
  wherein the second partial derivatives are partial derivatives of the respective partial representation with respect to the one or more shared parameters.

EEE 40 is the method of any of EEEs 1-39, further comprising removing, by the managing computing device, the list of unique objects, the shared representation, the lists of identifiers of each dataset of the plurality of datasets, and the composite list of identifiers from a memory of the managing computing device.

EEE 41 is the method of any of EEEs 1-40,
wherein each of the plurality of datasets comprises at least two dimensions,
wherein a first dimension of each of the plurality of datasets comprises a plurality of chemical compounds,
wherein a second dimension of each of the plurality of datasets comprises descriptors of the chemical compounds,
wherein entries in each of the plurality of datasets correspond to a binary indication of whether a respective chemical compound exhibits a respective descriptor,
wherein each of the sets of recorded values corresponding to each of the plurality of datasets comprises at least two dimensions,
wherein a first dimension of each of the sets of recorded values comprises the plurality of chemical compounds,
wherein a second dimension of each of the sets of recorded values comprises activities of the chemical compounds in a plurality of biological assays, and
wherein entries in each of the sets of recorded values correspond to a binary indication of whether a respective chemical compound exhibits a respective activity.

EEE 42 is the method of EEE 41, further comprising:
calculating, by the managing computing device, a final shared representation of the datasets based on the list of unique objects, the shared function, and the one or more shared parameters; and
transmitting, by the managing computing device, the final shared representation of the datasets to each of the client computing devices,
wherein the final shared representation of the datasets is usable by each of the client computing devices to determine a final set of predicted values corresponding to the respective dataset, and
wherein the final set of predicted values is used by at least one of the client computing devices to identify one or more effective treatment compounds among the plurality of chemical compounds.

EEE 43 is the method of any of EEEs 1-40,
wherein each of the plurality of datasets comprises at least two dimensions,
wherein a first dimension of each of the plurality of datasets comprises a plurality of patients,
wherein a second dimension of each of the plurality of datasets comprises descriptors of the patients,
wherein entries in each of the plurality of datasets correspond to a binary indication of whether a respective patient exhibits a respective descriptor,
wherein each of the sets of recorded values corresponding to each of the plurality of datasets comprises at least two dimensions,
wherein a first dimension of each of the sets of recorded values comprises the plurality of patients,
wherein a second dimension of each of the sets of recorded values comprises clinical diagnoses of the patients, and
wherein entries in each of the sets of recorded values correspond to a binary indication of whether a respective patient exhibits a respective clinical diagnosis.

EEE 44 is the method of EEE 43, further comprising:
calculating, by the managing computing device, a final shared representation of the datasets based on the list of unique objects, the shared function, and the one or more shared parameters; and
transmitting, by the managing computing device, the final shared representation of the datasets to each of the client computing devices,
wherein the final shared representation of the datasets is usable by each of the client computing devices to determine a final set of predicted values corresponding to the respective dataset, and
wherein the final set of predicted values is used by at least one of the client computing devices to diagnose at least one of the plurality of patients.

EEE 45 is the method of any of EEEs 1-40,
wherein each of the plurality of datasets comprises at least two dimensions,
wherein a first dimension of each of the plurality of datasets comprises a plurality of users,
wherein a second dimension of each of the plurality of datasets comprises a plurality of book titles,
wherein entries in each of the plurality of datasets correspond to a rating of a respective book title by a respective user,
wherein each of the sets of recorded values corresponding to each of the plurality of datasets comprises at least two dimensions,
wherein a first dimension of each of the sets of recorded values comprises the plurality of users,
wherein a second dimension of each of the sets of recorded values comprises a plurality of movie titles, and
wherein entries in each of the sets of recorded values correspond to a rating of a respective movie title by a respective user.

EEE 46 is the method of EEE 45, further comprising:
calculating, by the managing computing device, a final shared representation of the datasets based on the list of unique objects, the shared function, and the one or more shared parameters; and
transmitting, by the managing computing device, the final shared representation of the datasets to each of the client computing devices,
wherein the final shared representation of the datasets is usable by each of the client computing devices to determine a final set of predicted values corresponding to the respective dataset, and
wherein the final set of predicted values is used by at least one of the client computing devices to recommend at least one of the plurality of movie titles to at least one of the plurality of users.

EEE 47 is the method of any of EEEs 1-40,
wherein each of the plurality of datasets comprises at least two dimensions,
wherein a first dimension of each of the plurality of datasets comprises a plurality of insurance policies,
wherein a second dimension of each of the plurality of datasets comprises a plurality of deductible amounts,
wherein entries in each of the plurality of datasets correspond to a binary indication of whether a respective insurance policy has a respective deductible amount,
wherein each of the sets of recorded values corresponding to each of the plurality of datasets comprises at least two dimensions,
wherein a first dimension of each of the sets of recorded values comprises the plurality of insurance policies,
wherein a second dimension of each of the sets of recorded values comprises a plurality of insurance premiums, and
wherein entries in each of the sets of recorded values correspond to a binary indication of whether a respective insurance policy has a respective insurance premium.

EEE 48 is the method of EEE 47, further comprising:
calculating, by the managing computing device, a final shared representation of the datasets based on the list of unique objects, the shared function, and the one or more shared parameters; and
transmitting, by the managing computing device, the final shared representation of the datasets to each of the client computing devices,
wherein the final shared representation of the datasets is usable by each of the client computing devices to determine a final set of predicted values corresponding to the respective dataset, and
wherein the final set of predicted values is used by at least one of the client computing devices to recommend an insurance premium based on a prospective deductible amount.

EEE 49 is the method of any of EEEs 1-40,
wherein each of the plurality of datasets comprises at least two dimensions,
wherein a first dimension of each of the plurality of datasets comprises a plurality of automobiles,
wherein a second dimension of each of the plurality of datasets comprises a plurality of automobile parts,
wherein entries in each of the plurality of datasets correspond to a binary indication of whether a respective automobile has a respective automobile part equipped,
wherein each of the sets of recorded values corresponding to each of the plurality of datasets comprises at least two dimensions,
wherein a first dimension of each of the sets of recorded values comprises the plurality of automobiles,
wherein a second dimension of each of the sets of recorded values comprises a plurality of average fuel efficiencies, and
wherein entries in each of the sets of recorded values correspond to a binary indication of whether a respective automobile has a respective average fuel efficiency.

EEE 50 is the method of EEE 49, further comprising:
calculating, by the managing computing device, a final shared representation of the datasets based on the list of unique objects, the shared function, and the one or more shared parameters; and
transmitting, by the managing computing device, the final shared representation of the datasets to each of the client computing devices,
wherein the final shared representation of the datasets is usable by each of the client computing devices to determine a final set of predicted values corresponding to the respective dataset, and
wherein the final set of predicted values is used by at least one of the client computing devices to predict an average fuel efficiency of an automobile model based on a set of equipped automobile parts.

EEE 51 is the method of any of EEEs 1-50,
wherein the respective dataset of a respective client computing device is stored in a primary memory storage, and
wherein the set of recorded values corresponding to the respective dataset are stored in a secondary memory storage.

EEE 52 is the method of any of EEEs 1-14, 18-20, or 22-51,
wherein each of the sets of predicted values corresponding to one of the plurality of datasets corresponds to a predicted value tensor,
wherein the predicted value tensor is factored into a first tensor multiplied by a second tensor, and
wherein the first tensor corresponds to the respective dataset multiplied by the one or more shared parameters.

EEE 53 is the method of EEE 52, wherein the respective dataset encodes side information about the objects of the dataset.

EEE 54 is the method of EEEs 52 or 53, wherein the predicted value tensor is factored using a Macau factorization method.

EEE 55 is the method of any of EEEs 1-54, wherein the individual loss function of each respective client computing device comprises a shared loss function.

EEE 56 is the method of any of EEEs 1-54, wherein a first individual loss function of the individual loss functions is different from a second individual loss function of the individual loss functions.

EEE 57 is a method, comprising:
receiving, by a managing computing device, a plurality of datasets, wherein each dataset of the plurality of datasets is received from a respective client computing device of a plurality of client computing devices, wherein each dataset corresponds to a set of recorded values, wherein each dataset relates a plurality of chemical compounds to a plurality of descriptors of the chemical compounds, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
the sublist of objects for the respective dataset; and
the partial representation for the respective dataset;
receiving, by the managing computing device, one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;

determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset relates the plurality of chemical compounds to activities of the chemical compounds in a plurality of biological assays;

updating, by the respective client computing device, the one or more individual parameters for the respective dataset; and determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values; and updating, by the managing computing device, the one or more shared parameters based on the one or more aggregated feedback values, wherein the shared representation, the shared function, or the one or more shared parameters are usable by at least one of the plurality of client computing devices to identify one or more effective treatment compounds among the plurality of chemical compounds.

EEE 58 is the method of EEE 57, wherein the plurality of descriptors comprises chemistry-derived fingerprints or descriptors identified via transcriptomics or image screening.

EEE 59 is a method, comprising:

receiving, by a managing computing device, a plurality of datasets, wherein each dataset of the plurality of datasets is received from a respective client computing device of a plurality of client computing devices, wherein each dataset corresponds to a set of recorded values, wherein each dataset relates a plurality of patients to a plurality of descriptors of the patients, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting, by the managing computing device, to each of the client computing devices:
the sublist of objects for the respective dataset; and
the partial representation for the respective dataset;

receiving, by the managing computing device, one or more feedback values from at least one of the client computing devices, wherein the one or more feedback values are determined by the client computing devices by:

determining, by the respective client computing device, a set of predicted values corresponding to the respective dataset, wherein the set of predicted values is based on the partial representation and an individual function with one or more individual parameters corresponding to the respective dataset;

determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset relates the plurality of patients to clinical diagnoses of patients;

updating, by the respective client computing device, the one or more individual parameters for the respective dataset; and determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values; and updating, by the managing computing device, the one or more shared parameters based on the one or more aggregated feedback values, wherein the shared representation, the shared function, or the one or more shared parameters are usable by at least one of the plurality of client computing devices to diagnose one or more of the plurality of patients.

EEE 60 is the method of EEE 59, wherein the plurality of descriptors of the patients comprises genomic-based descriptors, patient demographics, patient age, patient height, patient weight, or patient gender.

EEE 61 is a method, comprising:

receiving, by a managing computing device, a plurality of datasets, wherein each dataset of the plurality of datasets is received from a respective client computing device of a plurality of client computing devices, wherein each dataset corresponds to a set of recorded values, wherein each dataset provides a set of book ratings for a plurality of book titles by a plurality of users, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting, by the managing computing device, to each of the client computing devices:
the sublist of objects for the respective dataset; and
the partial representation for the respective dataset;

receiving, by the managing computing device, one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;
determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset provides a set of movie ratings for a plurality of movie titles by the plurality of users;
updating, by the respective client computing device, the one or more individual parameters for the respective dataset; and
determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values; and updating, by the managing computing device, the one or more shared parameters based on the one or more aggregated feedback values, wherein the shared representation, the shared function, or the one or more shared parameters are usable by at least one of the plurality of client computing devices to recommend a movie to one or more of the plurality of users.

EEE 62 is the method of EEE 61, wherein the book ratings comprise at least one of: binary ratings, classification ratings, or numerical ratings.

EEE 63 is the method of EEEs 61 or 62, wherein the movie ratings comprise at least one of: binary ratings, classification ratings, or numerical ratings.

EEE 64 is a method, comprising:
transmitting, by a first client computing device to a managing computing device, a first dataset corresponding to the first client computing device,
wherein the first dataset is one of a plurality of datasets transmitted to the managing computing device by a plurality of client computing devices,
wherein each dataset corresponds to a set of recorded values, and
wherein each dataset comprises objects;

receiving, by the first client computing device, a first sublist of objects for the first dataset and a first partial representation for the first dataset,
wherein the first sublist of objects for the first dataset and the first partial representation for the first dataset are determined by the managing computing device by:
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the plurality of datasets based on the subset of the list of unique objects and a shared function having one or more shared parameters;
determining, by the managing computing device, the first sublist of objects for the first dataset based on an intersection of the subset of identifiers with the list of identifiers for the first dataset; and
determining, by the managing computing device, the first partial representation for the first dataset based on the first sublist of objects and the shared representation;

determining, by the first client computing device, a first set of predicted values corresponding to the first dataset, wherein the first set of predicted values is based on the first partial representation and a first individual function with one or more first individual parameters corresponding to the first dataset;

determining, by the first client computing device, a first error for the first dataset based on a first individual loss function for the first dataset, the first set of predicted values corresponding to the first dataset, the first sublist of objects, and non-empty entries in the set of recorded values corresponding to the first dataset;

updating, by the first client computing device, the one or more first individual parameters for the first dataset;

determining, by the first client computing device, one or more feedback values, wherein the one or more feedback values are used to determine a change in the first partial representation that corresponds to an improvement in the first set of predicted values; and transmitting, by the first client computing device to the managing computing device, the one or more feedback values, wherein the one or more feedback values are usable by the managing computing device along with sublists of objects from the plurality of client computing devices to determine one or more aggregated feedback values, and wherein the one or more aggregated feedback values are usable by the managing computing device to update the one or more shared parameters.

EEE 65 is a non-transitory, computer-readable medium with instructions stored thereon, wherein the instructions are executable by a processor to perform a method, comprising:

receiving a plurality of datasets, wherein each dataset of the plurality of datasets is received from a respective client computing device of a plurality of client computing devices, wherein each dataset corresponds to a set of recorded values, and wherein each dataset comprises objects;

determining a respective list of identifiers for each dataset and a composite list of identifiers comprising a combination of the lists of identifiers of each dataset of the plurality of datasets;

determining a list of unique objects from among the plurality of datasets;

selecting a subset of identifiers from the composite list of identifiers;

determining a subset of the list of unique objects corresponding to each identifier in the subset of identifiers;

computing a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting to each of the client computing devices:
the sublist of objects for the respective dataset; and
the partial representation for the respective dataset;

receiving one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;
determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
updating, by the respective client computing device, the one or more individual parameters for the respective dataset; and
determining, by the respective client computing device, the one or more feedback values, wherein the one or more feedback values are used to determine a change in the partial representation that corresponds to an improvement in the set of predicted values;

determining based on the sublists of objects and the one or more feedback values from the client computing devices, one or more aggregated feedback values; and
updating the one or more shared parameters based on the one or more aggregated feedback values.

EEE 66 is a memory with a model stored thereon, wherein the model is generated according to a method, comprising:

receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers; computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting, by the managing computing device, to each of the client computing devices:
the sublist of objects for the respective dataset; and
the partial representation for the respective dataset;

receiving, by the managing computing device, one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;
determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
updating, by the respective client computing device, the one or more individual parameters for the respective dataset; and
determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values;

updating, by the managing computing device, the one or more shared parameters based on the one or more aggregated feedback values; and storing, by the managing computing device, the shared representation, the shared function, and the one or more shared parameters on the memory.

EEE 67 is a method, comprising:

receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting, by the managing computing device, to each of the client computing devices:
 the sublist of objects for the respective dataset; and
 the partial representation for the respective dataset;

receiving, by the managing computing device, one or more feedback values from at least one of the client computing devices, wherein the one or more feedback values are determined by the client computing devices by:
 determining, by the respective client computing device, a set of predicted values corresponding to the respective dataset, wherein the set of predicted values is based on the partial representation and an individual function with one or more individual parameters corresponding to the respective dataset;
 determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
 updating, by the respective client computing device, the one or more individual parameters for the respective dataset; and
 determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values;

updating, by the managing computing device, the one or more shared parameters based on the one or more aggregated feedback values; and using, by a computing device, the shared representation, the shared function, or the one or more shared parameters to determine an additional set of predicted values corresponding to a dataset.

EEE 68 is a server device, wherein the server device has instructions stored thereon that, when executed by a processor, perform a method, the method comprising:

receiving a plurality of datasets, wherein each dataset of the plurality of datasets is received from a respective client computing device of a plurality of client computing devices, wherein each dataset corresponds to a set of recorded values, and wherein each dataset comprises objects;

determining a respective list of identifiers for each dataset and a composite list of identifiers comprising a combination of the lists of identifiers of each dataset of the plurality of datasets;

determining a list of unique objects from among the plurality of datasets;

selecting a subset of identifiers from the composite list of identifiers;

determining a subset of the list of unique objects corresponding to each identifier in the subset of identifiers;

computing a shared representation of the datasets based on the subset of the list of unique objects and a shared function having one or more shared parameters;

determining a sublist of objects for the respective dataset of each client computing device based on an intersection of the subset of identifiers with the list of identifiers for the respective dataset;

determining a partial representation for the respective dataset of each client computing device based on the sublist of objects for the respective dataset and the shared representation;

transmitting to each of the client computing devices:
 the sublist of objects for the respective dataset; and
 the partial representation for the respective dataset;

receiving one or more feedback values from at least one of the client computing devices, wherein the one or more feedback values are determined by the client computing devices by:
 determining, by the respective client computing device, a set of predicted values corresponding to the respective dataset, wherein the set of predicted values is based on the partial representation and an individual function with one or more individual parameters corresponding to the respective dataset;
 determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;

updating, by the respective client computing device, the one or more individual parameters for the respective dataset; and determining, by the respective client computing device, the one or more feedback values, wherein the one or more feedback values are used to determine a change in the partial representation that corresponds to an improvement in the set of predicted values;

determining based on the sublists of objects and the one or more feedback values from the client computing devices, one or more aggregated feedback values; and updating the one or more shared parameters based on the one or more aggregated feedback values.

EEE 69 is a server device, wherein the server device has instructions stored thereon that, when executed by a processor, perform a method, the method comprising:

transmitting, to a managing computing device, a first dataset corresponding to the server device, wherein the first dataset is one of a plurality of datasets transmitted to the managing computing device by a plurality of server devices, wherein each dataset corresponds to a set of recorded values, and wherein each dataset comprises objects;

receiving a first sublist of objects for the first dataset and a first partial representation for the first dataset, wherein the first sublist of objects for the first dataset and the first partial representation for the first dataset are determined by the managing computing device by:

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the plurality of datasets based on the subset of the list of unique objects and a shared function having one or more shared parameters;

determining, by the managing computing device, the first sublist of objects for the first dataset based on an intersection of the subset of identifiers with the list of identifiers for the first dataset; and determining, by the managing computing device, the first partial representation for the first dataset based on the first sublist of objects and the shared representation;

determining a first set of predicted values corresponding to the first dataset, wherein the first set of predicted values is based on the first partial representation and a first individual function with one or more first individual parameters corresponding to the first dataset;

determining a first error for the first dataset based on a first individual loss function for the first dataset, the first set of predicted values corresponding to the first dataset, the first sublist of objects, and non-empty entries in the set of recorded values corresponding to the first dataset;

updating the one or more first individual parameters for the first dataset;

determining one or more feedback values, wherein the one or more feedback values are used to determine a change in the first partial representation that corresponds to an improvement in the first set of predicted values; and transmitting, to the managing computing device, the one or more feedback values, wherein the one or more feedback values are usable by the managing computing device along with sublists of objects from the plurality of server devices to determine one or more aggregated feedback values, and wherein the one or more aggregated feedback values are usable by the managing computing device to update the one or more shared parameters.

EEE 70 is a system, comprising:

a server device; and a plurality of client devices each communicatively coupled to the server device, wherein the server device has instructions stored thereon that, when executed by a processor, perform a first method, the first method comprising:

receiving a plurality of datasets, wherein each dataset of the plurality of datasets is received from a respective client device of the plurality of client devices, wherein each dataset corresponds to a set of recorded values, and wherein each dataset comprises objects;

determining a respective list of identifiers for each dataset and a composite list of identifiers comprising a combination of the lists of identifiers of each dataset of the plurality of datasets;

determining a list of unique objects from among the plurality of datasets;

selecting a subset of identifiers from the composite list of identifiers;

determining a subset of the list of unique objects corresponding to each identifier in the subset of identifiers;

computing a shared representation of the datasets based on the subset of the list of unique objects and a shared function having one or more shared parameters;

determining a sublist of objects for the respective dataset of each client device based on an intersection of the subset of identifiers with the list of identifiers for the respective dataset;

determining a partial representation for the respective dataset of each client device based on the sublist of objects for the respective dataset and the shared representation;

transmitting to each of the client devices:
the sublist of objects for the respective dataset; and
the partial representation for the respective dataset, wherein each client device has instructions stored thereon that, when executed by a processor, perform a second method, the second method comprising:

determining a set of predicted values corresponding to the respective dataset, wherein the set of predicted values is based on the partial representation and an individual function with one or more individual parameters corresponding to the respective dataset;

determining an error for the respective dataset based on an individual loss function for the respective dataset, the set of predicted values corresponding to the respective dataset, the sublist of objects, and non-empty entries in the set of recorded values corresponding to the respective dataset;
updating the one or more individual parameters for the respective dataset;
determining one or more feedback values, wherein the one or more feedback values are used to determine a change in the partial representation that corresponds to an improvement in the set of predicted values; and
transmitting, to the server device, the one or more feedback values, and wherein the first method further comprises:
determining based on the sublists of objects and the one or more feedback values from the client devices, one or more aggregated feedback values; and
updating the one or more shared parameters based on the one or more aggregated feedback values.

EEE 71 is an optimized model, wherein the model is optimized according to a method, the method comprising:
receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
the sublist of objects for the respective dataset; and
the partial representation for the respective dataset;
receiving, by the managing computing device, one or more feedback values from at least one of the client computing devices, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;
determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
updating, by the respective client computing device, the one or more individual parameters for the respective dataset; and
determining, by the respective client computing device, the one or more feedback values, wherein the one or more feedback values are used to determine a change in the partial representation that corresponds to an improvement in the set of predicted values;
determining, by the managing computing device, based on the sublists of objects and the one or more feedback values from the client computing devices, one or more aggregated feedback values;
updating, by the managing computing device, the one or more shared parameters based on the one or more aggregated feedback values; and
computing, by the managing computing device, an updated shared representation of the datasets based on the shared function and the one or more updated shared parameters,
wherein the updated shared representation corresponds to the optimized model.

EEE 72 is a computer-implemented method, comprising:
receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
the sublist of objects for the respective dataset; and
the partial representation for the respective dataset;
receiving, by the managing computing device, one or more feedback values from at least one of the client computing devices, wherein the one or more feedback values are determined by the client computing devices by:

determining, by the respective client computing device, a set of predicted values corresponding to the respective dataset, wherein the set of predicted values is based on the partial representation and an individual function with one or more individual parameters corresponding to the respective dataset;

determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;

updating, by the respective client computing device, the one or more individual parameters for the respective dataset; and determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values; and updating, by the managing computing device, the one or more shared parameters based on the one or more aggregated feedback values.

EEE 73 is a computer-implemented method, comprising:

receiving, by a managing computing device, a plurality of datasets, wherein each dataset of the plurality of datasets is received from a respective client computing device of a plurality of client computing devices, wherein each dataset corresponds to a set of recorded values, wherein each dataset relates a plurality of chemical compounds to a plurality of descriptors of the chemical compounds, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;

determining, by the managing computing device, a partial representation for the respective dataset of each client computing device based on the sublist of objects for the respective dataset and the shared representation;

transmitting, by the managing computing device, to each of the client computing devices:
  the sublist of objects for the respective dataset; and
  the partial representation for the respective dataset;

receiving, by the managing computing device, one or more feedback values from at least one of the client computing devices, wherein the one or more feedback values are determined by the client computing devices by:
  determining, by the respective client computing device, a set of predicted values corresponding to the respective dataset, wherein the set of predicted values is based on the partial representation and an individual function with one or more individual parameters corresponding to the respective dataset;
  determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset relates the plurality of chemical compounds to activities of the chemical compounds in a plurality of biological assays;
  updating, by the respective client computing device, the one or more individual parameters for the respective dataset; and
  determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values; and updating, by the managing computing device, the one or more shared parameters based on the one or more aggregated feedback values, wherein the shared representation, the shared function, or the one or more shared parameters are usable by at least one of the plurality of client computing devices to identify one or more effective treatment compounds among the plurality of chemical compounds.

EEE 74 is a computer-implemented method, comprising:

receiving, by a managing computing device, a plurality of datasets, wherein each dataset of the plurality of datasets is received from a respective client computing device of a plurality of client computing devices, wherein each dataset corresponds to a set of recorded values, wherein each dataset relates a plurality of patients to a plurality of descriptors of the patients, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a list of unique objects from among the plurality of datasets;

selecting, by the managing computing device, a subset of identifiers from the composite list of identifiers;

determining, by the managing computing device, a subset of the list of unique objects corresponding to each identifier in the subset of identifiers;

computing, by the managing computing device, a shared representation of the datasets based on the subset of the list of unique objects and a shared function having one or more shared parameters;

determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
 the sublist of objects for the respective dataset; and
 the partial representation for the respective dataset;
receiving, by the managing computing device, one or more feedback values from at least one of the client computing devices, wherein the one or more feedback values are determined by the client computing devices by:
 determining, by the respective client computing device, a set of predicted values corresponding to the respective dataset, wherein the set of predicted values is based on the partial representation and an individual function with one or more individual parameters corresponding to the respective dataset;
 determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset relates the plurality of patients to clinical diagnoses of patients;
 updating, by the respective client computing device, the one or more individual parameters for the respective dataset; and
 determining, by the respective client computing device, the one or more feedback values, wherein the one or more feedback values are used to determine a change in the partial representation that corresponds to an improvement in the set of predicted values;
determining, by the managing computing device, based on the sublists of objects and the one or more feedback values from the client computing devices, one or more aggregated feedback values; and
updating, by the managing computing device, the one or more shared parameters based on the one or more aggregated feedback values,
wherein the shared representation, the shared function, or the one or more shared parameters are usable by at least one of the plurality of client computing devices to diagnose one or more of the plurality of patients.

EEE 75 is a computer-implemented method, comprising:
receiving, by a managing computing device, a plurality of datasets, wherein each dataset of the plurality of datasets is received from a respective client computing device of a plurality of client computing devices, wherein each dataset corresponds to a set of recorded values, wherein each dataset provides a set of book ratings for a plurality of book titles by a plurality of users, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
 the sublist of objects for the respective dataset; and
 the partial representation for the respective dataset;
receiving, by the managing computing device, one or more feedback values from at least one of the client computing devices, wherein the one or more feedback values are determined by the client computing devices by:
 determining, by the respective client computing device, a set of predicted values corresponding to the respective dataset, wherein the set of predicted values is based on the partial representation and an individual function with one or more individual parameters corresponding to the respective dataset;
 determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset, wherein the set of recorded values corresponding to the respective dataset provides a set of movie ratings for a plurality of movie titles by the plurality of users;
 updating, by the respective client computing device, the one or more individual parameters for the respective dataset; and
 determining, by the respective client computing device, the one or more feedback values, wherein the one or more feedback values are used to determine a change in the partial representation that corresponds to an improvement in the set of predicted values;
determining, by the managing computing device, based on the sublists of objects and the one or more feedback values from the client computing devices, one or more aggregated feedback values; and
updating, by the managing computing device, the one or more shared parameters based on the one or more aggregated feedback values,
wherein the shared representation, the shared function, or the one or more shared parameters are usable by at least one of the plurality of client computing devices to recommend a movie to one or more of the plurality of users.

EEE 76 is a computer-implemented method, comprising:
transmitting, by a first client computing device to a managing computing device, a first dataset corresponding to the first client computing device,
wherein the first dataset is one of a plurality of datasets transmitted to the managing computing device by a plurality of client computing devices,
wherein each dataset corresponds to a set of recorded values, and
wherein each dataset comprises objects;
receiving, by the first client computing device, a first sublist of objects for the first dataset and a first partial representation for the first dataset,
wherein the first sublist of objects for the first dataset and the first partial representation for the first dataset are determined by the managing computing device by:
    determining, by the managing computing device, a respective list of identifiers for each dataset and a composite list of identifiers comprising a combination of the lists of identifiers of each dataset of the plurality of datasets;
    determining, by the managing computing device, a list of unique objects from among the plurality of datasets;
    selecting, by the managing computing device, a subset of identifiers from the composite list of identifiers;
    determining, by the managing computing device, a subset of the list of unique objects corresponding to each identifier in the subset of identifiers;
    computing, by the managing computing device, a shared representation of the plurality of datasets based on the subset of the list of unique objects and a shared function having one or more shared parameters;
    determining, by the managing computing device, the first sublist of objects for the first dataset based on an intersection of the subset of identifiers with the list of identifiers for the first dataset; and
    determining, by the managing computing device, the first partial representation for the first dataset based on the first sublist of objects and the shared representation;
determining, by the first client computing device, a first set of predicted values corresponding to the first dataset, wherein the first set of predicted values is based on the first partial representation and a first individual function with one or more first individual parameters corresponding to the first dataset;
determining, by the first client computing device, a first error for the first dataset based on a first individual loss function for the first dataset, the first set of predicted values corresponding to the first dataset, the first sublist of objects, and non-empty entries in the set of recorded values corresponding to the first dataset;
updating, by the first client computing device, the one or more first individual parameters for the first dataset;
determining, by the first client computing device, one or more feedback values, wherein the one or more feedback values are used to determine a change in the first partial representation that corresponds to an improvement in the first set of predicted values; and
transmitting, by the first client computing device to the managing computing device, the one or more feedback values,
wherein the one or more feedback values are usable by the managing computing device along with sublists of objects from the plurality of client computing devices to determine one or more aggregated feedback values, and
wherein the one or more aggregated feedback values are usable by the managing computing device to update the one or more shared parameters.

EEE 77 is a computer-implemented method, comprising:
receiving, by a managing computing device, a plurality of datasets, wherein each dataset of the plurality of datasets is received from a respective client computing device of a plurality of client computing devices, wherein each dataset corresponds to a set of recorded values, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a list of unique objects from among the plurality of datasets;
selecting, by the managing computing device, a subset of identifiers from the composite list of identifiers;
determining, by the managing computing device, a subset of the list of unique objects corresponding to each identifier in the subset of identifiers;
computing, by the managing computing device, a shared representation of the datasets based on the subset of the list of unique objects and a shared function having one or more shared parameters;
determining, by the managing computing device, a sublist of objects for the respective dataset of each client computing device based on an intersection of the subset of identifiers with the list of identifiers for the respective dataset;
determining, by the managing computing device, a partial representation for the respective dataset of each client computing device based on the sublist of objects for the respective dataset and the shared representation;
transmitting, by the managing computing device, to each of the client computing devices:
    the sublist of objects for the respective dataset; and
    the partial representation for the respective dataset;
receiving, by the managing computing device, one or more feedback values from at least one of the client computing devices, wherein the one or more feedback values are determined by the client computing devices by:
    determining, by the respective client computing device, a set of predicted values corresponding to the respective dataset, wherein the set of predicted values is based on the partial representation and an individual function with one or more individual parameters corresponding to the respective dataset;
    determining, by the respective client computing device, an error for the respective dataset based on an individual loss function for the respective dataset, the set of predicted values corresponding to the respective dataset, the sublist of objects, and non-empty entries in the set of recorded values corresponding to the respective dataset;
    updating, by the respective client computing device, the one or more individual parameters for the respective dataset; and
    determining, by the respective client computing device, the one or more feedback values, wherein the one or more feedback values are used to determine a change in the partial representation that corresponds to an improvement in the set of predicted values;

determining, by the managing computing device, based on the sublists of objects and the one or more feedback values from the client computing devices, one or more aggregated feedback values;

updating, by the managing computing device, the one or more shared parameters based on the one or more aggregated feedback values; and using, by a computing device, the shared representation, the shared function, or the one or more shared parameters to determine an additional set of predicted values corresponding to a dataset.

The invention claimed is:

1. A method for machine learning, comprising:
receiving, by a managing computing device, a plurality of datasets, wherein each dataset of the plurality of datasets is a respective dataset received from a respective client computing device of a plurality of client computing devices, wherein each dataset corresponds to a set of recorded values, and wherein each dataset comprises objects;

determining, by the managing computing device, a respective list of identifiers for each dataset and a composite list of identifiers comprising a combination of the lists of identifiers of each dataset of the plurality of datasets;

determining, by the managing computing device, a set of unique objects from among the plurality of datasets;

selecting, by the managing computing device, a subset of identifiers from the composite list of identifiers;

determining, by the managing computing device, a subset of the set of unique objects corresponding to each identifier in the subset of identifiers;

computing, by the managing computing device, a shared representation of the plurality of datasets based on the subset of the set of unique objects and a shared function having one or more shared parameters;

determining, by the managing computing device, a subset of objects for the respective dataset received from each respective client computing device based on an intersection of the subset of identifiers with the list of identifiers for the respective dataset;

determining, by the managing computing device, a partial representation for the respective dataset received from each respective client computing device based on the subset of objects for the respective dataset and the shared representation;

acquiring, by the managing computing device, one or more feedback values, wherein each of the one or more feedback values is determined as a change in the partial representation that corresponds to an improvement in a set of predicted values as compared to the set of recorded values corresponding to the respective dataset;

determining, by the managing computing device, based on the subsets of objects and the one or more feedback values from the client computing devices, one or more aggregated feedback values; and updating, by the managing computing device, the one or more shared parameters based on the one or more aggregated feedback values.

2. The method of claim 1, wherein each dataset comprises objects in a plurality of dimensions, and wherein the objects in at least one of the plurality of dimensions for each dataset is of a same type.

3. The method of claim 1 wherein the respective list of identifiers for each dataset corresponds to a set of objects for each dataset, wherein the identifiers for the plurality of datasets are defined according to a common syntax.

4. The method of claim 1, further comprising transmitting, by the managing computing device, to each of the client computing devices: the subset of objects for the respective dataset; and the partial representation for the respective dataset; and wherein said acquiring comprises receiving, by the managing computing device, one or more feedback values from at least one of the client computing devices.

5. The method of claim 4, wherein the one or more feedback values are determined by the client computing devices by:
determining, by the respective client computing device, a set of predicted values corresponding to the respective dataset, wherein the set of predicted values is based on the partial representation and an individual function with one or more individual parameters corresponding to the respective dataset;

determining, by the respective client computing device, an error for the respective dataset based on an individual loss function for the respective dataset, the set of predicted values corresponding to the respective dataset, the subset of objects, and non-empty entries in the set of recorded values corresponding to the respective dataset;

updating, by the respective client computing device, the one or more individual parameters for the respective dataset; and determining, by the respective client computing device, the one or more feedback values, wherein the one or more feedback values are used to determine a change in the partial representation that corresponds to an improvement in the set of predicted values.

6. The method of claim 4 further comprising transmitting, by the managing computing device, the shared function and the one or more shared parameters to each of the client computing devices.

7. The method of claim 1, wherein determining, by the managing computing device, the set of unique objects from among the plurality of datasets comprises:
creating, by the managing computing device, a composite set of objects that is a combination of the objects from each dataset; and removing, by the managing computing device, duplicate objects from the composite set of objects based on an intersection of the lists of identifiers for each of the plurality of datasets.

8. The method of claim 5, wherein determining the error for the respective dataset comprises:
identifying, by the respective client computing device, which of the non-empty entries in the set of recorded values corresponding to the respective dataset corresponds to an object in the subset of objects;

determining, by the respective client computing device, a partial error value for each of the identified non-empty entries in the set of recorded values corresponding to the respective dataset by applying the individual loss function between each identified non-empty entry and its corresponding predicted value in the set of predicted values corresponding to the respective dataset; and combining, by the respective client computing device, the partial error values.

9. The method of claim 5, further comprising:
calculating, by the managing computing device, a final shared representation of the plurality of datasets based on the set of unique objects, the shared function, and the one or more shared parameters; and transmitting, by the managing computing device, the final shared representation of the plurality of datasets to each of the client computing devices.

10. The method of claim 9, wherein the final shared representation of the plurality of datasets is usable by each of the client computing devices to determine a final set of predicted values corresponding to the respective dataset.

11. The method of claim 10, wherein determining the final set of predicted values corresponding to the respective dataset comprises:

receiving, by the respective client computing device, the subset of objects for the respective dataset;

determining, by the respective client computing device, a final partial representation for the respective dataset based on the subset of objects and the final shared representation; and determining, by the respective client computing device, the final set of predicted values corresponding to the respective dataset based on the final partial representation, the individual function, and the one or more individual parameters corresponding to the respective dataset.

12. The method of claim 5, wherein the one or more feedback values from each of the client computing devices are based on back-propagated errors.

13. The method of claim 1, wherein each of the plurality of datasets comprises an equal number of dimensions.

14. The method of claim 1, wherein each of the plurality of datasets is represented by a tensor, and wherein at least one of the plurality of datasets is represented by a sparse tensor.

15. The method of claim 5, further comprising:

selecting, by the managing computing device, an additional subset of identifiers from the composite list of identifiers;

determining, by the managing computing device, an additional subset of the set of unique objects corresponding to each identifier in the additional subset of identifiers;

computing, by the managing computing device, a revised shared representation of the plurality of datasets based on the additional subset of the set of unique objects and the shared function having the one or more shared parameters;

determining, by the managing computing device, additional subsets of objects for the respective dataset of each client computing device based on an intersection of the additional subset of identifiers with the list of identifiers for the respective dataset;

determining, by the managing computing device, a revised partial representation for the respective dataset of each client computing device based on the additional subset of objects for the respective dataset and the revised shared representation;

transmitting, by the managing computing device, to each of the client computing devices:

the additional subset of objects for the respective dataset; and the revised partial representation for the respective dataset;

receiving, by the managing computing device, one or more revised feedback values from at least one of the client computing devices, wherein the one or more revised feedback values are determined by the client computing devices by:

determining, by the respective client computing device, a revised set of predicted values corresponding to the respective dataset, wherein the revised set of predicted values is based on the revised partial representation and the individual function with the one or more individual parameters corresponding to the respective dataset;

determining, by the respective client computing device, a revised error for the respective dataset based on the individual loss function for the respective dataset, the revised set of predicted values corresponding to the respective dataset, the additional subset of objects, and the non-empty entries in the set of recorded values corresponding to the respective dataset;

updating, by the respective client computing device, the one or more individual parameters for the respective dataset; and determining, by the respective client computing device, the one or more revised feedback values, wherein the one or more revised feedback values are used to determine a change in the revised partial representation that corresponds to an improvement in the set of predicted values;

determining, by the managing computing device, based on the additional subsets of objects and the one or more revised feedback values, one or more revised aggregated feedback values;

updating, by the managing computing device, the one or more shared parameters based on the one or more revised aggregated feedback values; and determining, by the managing computing device based on the one or more revised aggregated feedback values, that an aggregated error corresponding to the revised errors for all respective datasets has been minimized.

16. The method of claim 1, further comprising initializing, by the managing computing device, the shared function and the one or more shared parameters based on a related shared function used to model a similar relationship.

17. The method of claim 5, wherein determining the one or more feedback values by the client computing devices further comprises initializing, by the respective client computing device, the individual function and the one or more individual parameters corresponding to the respective dataset based on a random number generator or a pseudo-random number generator.

18. The method of claim 1, wherein each of the plurality of datasets comprises at least two dimensions, wherein a first dimension of each of the plurality of datasets comprises a plurality of chemical compounds, wherein a second dimension of each of the plurality of datasets comprises descriptors of the chemical compounds, wherein entries in each of the plurality of datasets correspond to a binary indication of whether a respective chemical compound exhibits a respective descriptor, wherein each of the sets of recorded values corresponding to each of the plurality of datasets comprises at least two dimensions, wherein a first dimension of each of the sets of recorded values comprises the plurality of chemical compounds, wherein a second dimension of each of the sets of recorded values comprises activities of the chemical compounds in a plurality of biological assays, and wherein entries in each of the sets of recorded values correspond to a binary indication of whether a respective chemical compound exhibits a respective activity.

19. The method of claim 18, further comprising:
calculating, by the managing computing device, a final shared representation of the plurality of datasets based on the set of unique objects, the shared function, and the one or more shared parameters; and
transmitting, by the managing computing device, the final shared representation of the plurality of datasets to each of the client computing devices,
wherein the final shared representation of the plurality of datasets is usable by each of the client computing devices to determine a final set of predicted values corresponding to the respective dataset, and
wherein the final set of predicted values is used by at least one of the client computing devices to identify one or more effective treatment compounds among the plurality of chemical compounds.

20. The method of claim 1,
wherein each of the plurality of datasets comprises at least two dimensions,
wherein a first dimension of each of the plurality of datasets comprises a plurality of patients,
wherein a second dimension of each of the plurality of datasets comprises descriptors of the patients,
wherein entries in each of the plurality of datasets correspond to a binary indication of whether a respective patient exhibits a respective descriptor,
wherein each of the sets of recorded values corresponding to each of the plurality of datasets comprises at least two dimensions,
wherein a first dimension of each of the sets of recorded values comprises the plurality of patients,
wherein a second dimension of each of the sets of recorded values comprises clinical diagnoses of the patients, and
wherein entries in each of the sets of recorded values correspond to a binary indication of whether a respective patient exhibits a respective clinical diagnosis.

21. The method of claim 20, further comprising:
calculating, by the managing computing device, a final shared representation of the plurality of datasets based on the set of unique objects, the shared function, and the one or more shared parameters; and
transmitting, by the managing computing device, the final shared representation of the plurality of datasets to each of the client computing devices,
wherein the final shared representation of the plurality of datasets is usable by each of the client computing devices to determine a final set of predicted values corresponding to the respective dataset, and
wherein the final set of predicted values is used by at least one of the client computing devices to diagnose at least one of the plurality of patients.

22. The method of claim 5,
wherein each of the sets of predicted values corresponding to one of the plurality of datasets corresponds to a predicted value tensor,
wherein the predicted value tensor is factored into a first tensor multiplied by a second tensor, and
wherein the first tensor corresponds to the respective dataset multiplied by the one or more shared parameters.

23. The method of claim 22, wherein the respective dataset encodes side information about the objects of the dataset.

24. The method of claim 22, wherein the predicted value tensor is factored using a Macau factorization method.

25. A non-transitory, computer-readable medium with instructions stored thereon, wherein the instructions are executable by a processor to perform a method, comprising:
receiving a plurality of datasets, wherein each dataset of the plurality of datasets is a respective dataset received from a respective client computing device of a plurality of client computing devices, wherein each dataset corresponds to a set of recorded values, and wherein each dataset comprises objects;
determining a respective list of identifiers for each dataset and a composite list of identifiers comprising a combination of the lists of identifiers of each dataset of the plurality of datasets;
determining a set of unique objects from among the plurality of datasets;
selecting a subset of identifiers from the composite list of identifiers;
determining a subset of the set of unique objects corresponding to each identifier in the subset of identifiers;
computing a shared representation of the plurality of datasets based on the subset of the set of unique objects and a shared function having one or more shared parameters;
determining a subset of objects for the respective dataset received from each respective client computing device based on an intersection of the subset of identifiers with the list of identifiers for the respective dataset;
determining a partial representation for the respective dataset received from each respective client computing device based on the subset of objects for the respective dataset and the shared representation;
acquiring one or more feedback values, wherein each of the one or more feedback values is determined based on a relation of predictions of the partial representation to the set of recorded values for the respective dataset;
determining based on the subsets of objects and the one or more feedback values from the client computing devices, one or more aggregated feedback values; and
updating the one or more shared parameters based on the one or more aggregated feedback values.

26. A memory with a model stored thereon, wherein the model is generated according to a method, comprising:
receiving, by a managing computing device, a plurality of datasets, wherein each dataset of the plurality of datasets is a respective dataset received from a respective client computing device of a plurality of client computing devices, wherein each dataset corresponds to a set of recorded values, and wherein each dataset comprises objects;
determining, by the managing computing device, a respective list of identifiers for each dataset and a composite list of identifiers comprising a combination of the lists of identifiers of each dataset of the plurality of datasets;
determining, by the managing computing device, a set of unique objects from among the plurality of datasets;
selecting, by the managing computing device, a subset of identifiers from the composite list of identifiers;
determining, by the managing computing device, a subset of the set of unique objects corresponding to each identifier in the subset of identifiers;
computing, by the managing computing device, a shared representation of the plurality of datasets based on the subset of the set of unique objects and a shared function having one or more shared parameters;

determining, by the managing computing device, a subset of objects for the respective dataset received from each respective client computing device based on an intersection of the subset of identifiers with the list of identifiers for the respective dataset;

determining, by the managing computing device, a partial representation for the respective dataset received from each respective client computing device based on the subset of objects for the respective dataset and the shared representation;

acquiring, by the managing computing device, one or more feedback values, wherein each of the one or more feedback values is determined based on a relation of predictions of the partial representation to the set of recorded values for each dataset;

determining, by the managing computing device, based on the subsets of objects and the one or more feedback values from the client computing devices, one or more aggregated feedback values;

updating, by the managing computing device, the one or more shared parameters based on the one or more aggregated feedback values; and storing, by the managing computing device, the shared representation, the shared function, and the one or more shared parameters on the memory.

27. A method for machine learning, comprising:

transmitting, by a first client computing device to a managing computing device, a first dataset corresponding to the first client computing device, wherein the first dataset is one of a plurality of datasets transmitted to the managing computing device by a plurality of client computing devices, wherein each dataset corresponds to a set of recorded values, and wherein each dataset comprises objects;

receiving, by the first client computing device, a first subset of objects for the first dataset and a first partial representation for the first dataset, wherein the first subset of objects is a subset of the objects of the first dataset being part of forming a shared representation of the plurality of datasets, the shared representation being defined by a shared function having one or more shared parameters, and the first partial representation for the first dataset is based on the first subset of objects and the shared representation;

determining, by the first client computing device, a first set of predicted values corresponding to the first dataset, wherein the first set of predicted values is based on the first partial representation and a first individual function with one or more first individual parameters corresponding to the first dataset;

determining, by the first client computing device, a first error for the first dataset based on a first individual loss function for the first dataset, the first set of predicted values corresponding to the first dataset, the first subset of objects, and non-empty entries in the set of recorded values corresponding to the first dataset;

updating, by the first client computing device, the one or more first individual parameters for the first dataset;

determining, by the first client computing device, one or more feedback values, wherein the one or more feedback values are used to determine a change in the first partial representation that corresponds to an improvement in the first set of predicted values; and transmitting, by the first client computing device to the managing computing device, the one or more feedback values, wherein the one or more feedback values are usable by the managing computing device along with subsets of objects from the plurality of client computing devices to determine one or more aggregated feedback values, and wherein the one or more aggregated feedback values are usable by the managing computing device to update the one or more shared parameters.

\* \* \* \* \*